US011344562B2

(12) United States Patent
Daugherty

(10) Patent No.: US 11,344,562 B2
(45) Date of Patent: May 31, 2022

(54) AQUEOUS NEBULIZATION COMPOSITION

(71) Applicant: Nephron Pharmaceuticals Corporation, West Columbia, SC (US)

(72) Inventor: Ashley Daugherty, West Columbia, SC (US)

(73) Assignee: Nephron Pharmaceuticals Corporation, West Columbia, SC (US)

( * ) Notice: Subject to any disclaimer, the term of this patent is extended or adjusted under 35 U.S.C. 154(b) by 0 days.

(21) Appl. No.: 16/103,630

(22) Filed: Aug. 14, 2018

(65) Prior Publication Data
US 2019/0054095 A1 Feb. 21, 2019

Related U.S. Application Data

(60) Provisional application No. 62/545,725, filed on Aug. 15, 2017.

(51) Int. Cl.

| | |
|---|---|
| *A61K 31/58* | (2006.01) |
| *A61K 9/10* | (2006.01) |
| *A61P 11/08* | (2006.01) |
| *A61K 47/26* | (2006.01) |
| *A61K 47/32* | (2006.01) |
| *A61K 9/00* | (2006.01) |
| *A61K 47/34* | (2017.01) |
| *A61K 9/08* | (2006.01) |

(52) U.S. Cl.
CPC ............ *A61K 31/58* (2013.01); *A61K 9/0078* (2013.01); *A61K 9/08* (2013.01); *A61K 9/10* (2013.01); *A61K 47/26* (2013.01); *A61K 47/32* (2013.01); *A61K 47/34* (2013.01); *A61P 11/08* (2018.01)

(58) Field of Classification Search
CPC ........ A61K 31/58; A61K 9/0078; A61K 9/08; A61K 47/26; A61K 47/32; A61K 47/34; A61K 9/10; A61P 11/08
See application file for complete search history.

(56) References Cited

U.S. PATENT DOCUMENTS

| | | | |
|---|---|---|---|
| 5,800,807 | A | 9/1998 | Hu et al. |
| 5,914,122 | A | 6/1999 | Otterbeck et al. |
| 6,027,714 | A | 2/2000 | Trofast |
| 6,123,924 | A | 9/2000 | Mistry et al. |
| 6,142,145 | A | 11/2000 | Dagsland et al. |
| 6,287,540 | B1 | 9/2001 | Trofast |
| 6,598,603 | B1 | 7/2003 | Andersson et al. |
| 6,899,099 | B2 | 5/2005 | Andersson et al. |
| 7,143,764 | B1 | 12/2006 | Dagsland et al. |
| 7,367,333 | B2 | 5/2008 | Hodson et al. |
| 7,410,651 | B2 | 8/2008 | Villa et al. |
| 7,431,943 | B1 | 10/2008 | Villa et al. |
| 7,524,834 | B2 | 4/2009 | Karlsson et al. |
| 7,587,988 | B2 | 9/2009 | Bowman et al. |
| 7,759,328 | B2 | 7/2010 | Govind et al. |
| 7,967,011 | B2 | 6/2011 | Hodson et al. |
| 8,143,239 | B2 | 3/2012 | Govind et al. |
| 8,158,686 | B2 | 4/2012 | Bouillo et al. |
| 8,293,273 | B2 | 10/2012 | Villa et al. |
| RE43,799 | E | 11/2012 | Villa et al. |
| 8,387,615 | B2 | 3/2013 | Bunce |
| 8,455,002 | B2 | 6/2013 | Shaw et al. |
| 8,466,134 | B1 * | 6/2013 | Saidi .................... A61K 9/1075 514/170 |
| 8,528,545 | B2 | 9/2013 | Hodson et al. |
| 8,575,137 | B2 | 11/2013 | Govind et al. |
| 8,616,196 | B2 | 12/2013 | Hodson et al. |
| 8,765,725 | B2 | 7/2014 | Cavanagh et al. |
| 8,784,888 | B2 | 7/2014 | Villa et al. |
| 8,790,703 | B2 | 7/2014 | Meyer-Bohm et al. |
| 8,875,699 | B2 | 11/2014 | Bunce |
| 8,895,064 | B2 | 11/2014 | Villa et al. |
| 9,132,093 | B2 | 9/2015 | Villa et al. |
| 9,192,581 | B2 | 11/2015 | Villa et al. |
| 9,320,716 | B2 | 4/2016 | Villa et al. |
| 9,555,002 | B2 | 1/2017 | Kolter et al. |
| 2008/0226736 | A1 | 9/2008 | Caponetti et al. |
| 2009/0036550 | A1 | 2/2009 | Bouillo et al. |
| 2011/0287066 | A1 | 11/2011 | Sandler et al. |
| 2012/0202894 | A1 | 8/2012 | Kolter et al. |
| 2012/0219695 | A1 | 8/2012 | Kolter et al. |
| 2012/0244197 | A1 | 9/2012 | Djuric et al. |
| 2013/0146050 | A1 * | 6/2013 | Arnfeldt Moller ....... A61F 5/56 128/200.14 |
| 2013/0157963 | A1 | 6/2013 | Gore |
| 2013/0236505 | A1 | 9/2013 | Kolter et al. |
| 2013/0274297 | A1 | 10/2013 | Gatti et al. |
| 2014/0328884 | A1 | 11/2014 | Reyes et al. |
| 2014/0348936 | A1 | 11/2014 | Reyes et al. |

(Continued)

FOREIGN PATENT DOCUMENTS

| | | |
|---|---|---|
| EP | 1302200 | 4/2003 |
| WO | WO2001087203 | 11/2001 |

(Continued)

OTHER PUBLICATIONS

Choi et al (Year: 2017).*
Notice from International Search Authority dated Oct. 16, 2018 for PCT/US2018/046732.
Rao et al., "Preparation and Characterization of Solid Dispersions for Solubility Enhancement of BCS Class II Drug," *World J Pharmacy and Pharmaceutical Sciences* 6:7 (2017) 1852-1869.
BASF Soluplus Technical Information 03_090801e-04 (Jul. 2010).
BASF Soluplus Toxicology Summary (Jan. 2014).
Fernanda Raquel da Silva Andrade, PhD Thesis: "Self-Assembled Polymeric Micelles as Powders for Pulmonary Administration of Insulin," Faculdade de Farmacia, Universidade do Porto, Portugal (2015).

(Continued)

*Primary Examiner* — Jeffrey S Lundgren
*Assistant Examiner* — Ibrahim D Bori
(74) *Attorney, Agent, or Firm* — Nexsen Pruet, PLLC; E. Eric Mills; John P. Zimmer

(57) ABSTRACT

Compositions and methods for making and using stable, homogeneous budesonide compositions are disclosed.

18 Claims, No Drawings

(56) References Cited

U.S. PATENT DOCUMENTS

| | | |
|---|---|---|
| 2015/0126483 A1 | 5/2015 | Cavanagh et al. |
| 2015/0140093 A1 | 5/2015 | Berkland et al. |
| 2015/0335753 A1 | 11/2015 | Desai et al. |
| 2015/0337006 A1 | 11/2015 | Barman et al. |
| 2016/0206627 A1 | 7/2016 | Gosselin et al. |
| 2016/0213609 A1 | 7/2016 | Shawer et al. |
| 2016/0235677 A1 | 8/2016 | Hoerr et al. |
| 2016/0354315 A1 | 12/2016 | Li |

FOREIGN PATENT DOCUMENTS

| | | | |
|---|---|---|---|
| WO | WO2011144731 | 11/2011 | |
| WO | WO2013037396 | 3/2013 | |
| WO | WO2013090891 | 6/2013 | |
| WO | WO2013090893 | 6/2013 | |
| WO | WO2013129644 | 9/2013 | |
| WO | WO2013169647 | 11/2013 | |
| WO | WO2014100403 | 6/2014 | |
| WO | WO2014107231 | 7/2014 | |
| WO | WO2015035114 | 3/2015 | |
| WO | WO-2015110993 A1 * | 7/2015 | ........... A61K 9/0048 |
| WO | WO2016086193 | 6/2016 | |
| WO | WO2016154240 | 9/2016 | |
| WO | WO2016192680 | 12/2016 | |

OTHER PUBLICATIONS

Linn et al., "Soluplus as an effective absorption enhancer of poorly soluble drugs in vitro and in vivo" *European J Pharmaceutical Sciences* 45 (2012) 336-343.

Pozzoli et al., "Development of a Soluplus budesonide freeze-dried powder for nasal drug delivery," *Drug Development and Industrial Pharmacy* (May 22, 2017) 9 pages, available at https://doi.org/10.1080/03639045.2017.1321659.

Patel et al., "Nanosuspension: An approach to enhance solubility of drugs," *J Advanced Pharmaceutical Technology & Research* 2:2 (2011) 81-87.

Tuomela et al., "Stabilizing Agents for Drug Nanocrystals: Effect on Bioavailability," *Pharmaceutics* 8:2 (May 20, 2016), available at doi: 10.3390/pharmaceutics8020016.

AstraZeneca, "Pulmicort Respules™ (budesonide inhalation suspension) 0.25 mg and 0.5 mg" (2000). Available at https://www.accessdata.fda.gov/drugsatfda_docs/label/2000/20929lbl.pdf.

PARI Respiratory Equipment, Inc. "Vios Pro Aerosol Delivery System," (2016). Available at https://www.pari.com/fileadmin/user_upload/PARI.com_Amerika/Brochures/312D0002-Vios-Pro-Detail-Sheet.pdf.

World Journal of Pharmacy and Pharcameutical Sciences, "2017 vol. 6, July Issue 7". Available at http://www.wjpps.com/wjpps_controller/archive_show/2017NOLUME%206,%20JULY%201SSUE%207.

International Search Report in PCT/US2018/046732 dated Dec. 7, 2018.

Written Opinion of International Search Authority in PCT/US2018/046732 dated Dec. 7, 2018.

"Pulmicort Respules (TM) (budesonide inhalation suspension)" Aug. 4, 2000, pp. 1-17.

Pozzoli Michele et al. 2017. "Development of a Soluplus budesonide freeze-dried powder for nasal drug delivery." Journal Drug Development and Industrial Pharmacy, vol. 43, No. 9, pp. 1510-1518.

\* cited by examiner

AQUEOUS NEBULIZATION COMPOSITION

CROSS-REFERENCE TO RELATED APPLICATIONS

This application claims the benefit of U.S. Provisional Application No. 62/545,725, filed Aug. 15, 2017 which is hereby by incorporated, in its entirety, by reference.

FIELD OF THE INVENTION

The present disclosure relates to pharmaceutical compositions comprising budesonide, or a pharmaceutically acceptable salt thereof, and processes for their preparation and use.

BACKGROUND OF THE INVENTION

Budesonide (CAS Registry No. 51333-22-3; designated chemically as (RS)-11-beta, 16-alpha, 17,21-tetrahydroxy-pregna-I,4-diene-3,20-dione cyclic 16,17-acetal with butyraldehyde) is a topically active corticosteroid having a broad spectrum of clinically significant local anti-inflammatory effects, and is a preferred active ingredient in inhalation treatments in patients with inflammatory lung diseases. As shown, budesonide is a mixture of two epimers (22R and 22S):

and

Budesonide is practically insoluble in water and in heptanes. While budesonide is at least sparingly soluble in many alcohols (particularly polyhydric alcohols and organic, and water-soluble glycols), in certain cases budesonide may rapidly decompose in solution, complicating efforts to develop an inhalable solution that can be stored prior to use (for example in sealed vials). Previous efforts to provide stable, inhalable budesonide solutions, including use of cyclodextrins or use of a modified budesonide, have not been proven pharmaceutically acceptable.

Current budesonide inhalation compositions comprise suspensions of micronized budesonide rather than solutions or nanodispersions. The Reference Listed Drug (RLD) for budesonide inhalation suspension is Pulmicort RESPULES® (budesonide) Inhalation Suspension (0.25 mg/2 mL or 0.5 mg/2 mL), marketed by AstraZeneca under the approved New Drug Application No. 020929, which is hereby incorporated by reference in its entirety. The product label for Pulmicort RESPULES® (budesonide) Inhalation Suspension is hereby incorporated by reference in its entirety.

It is believed that a budesonide solution (or nanodisperson) would be more efficiently nebulized and deliver more consistent dosing than a suspension. Accordingly, there is a need for stable, inhalable pharmaceutical solutions that can be administered to patients in need thereof using available nebulizers (for example a vibrating mesh nebulizer or an air-driven jet nebulizer) or inhalers (for example the propellant-free, hand-held inhaler manufactured by Boehringer Ingelheim sold under the trademarks RESPIMAT SOFT MIST).

BRIEF SUMMARY OF THE INVENTION

Certain embodiments may provide, for example, a stable, homogenous, nebulizable budesonide composition (for example a solution or nanodispersion) comprising budesonide (or pharmaceutically acceptable salt thereof) and a polyvinyl caprolactam-polyvinyl acetate-polyethylene glycol graft copolymer, the copolymer present at a weight ratio of less than (or no more than) 5:1 (for example less than (or no more than) 4:1 or less than (or no more than) 2:1) relative to the weight of budesonide in the composition, and at least 90 wt. % water. In certain embodiments, for example, the stable, homogenous, nebulizable budesonide composition may further comprise a second drug (for example formoterol or pharmaceutically acceptable salt and/or hydrate thereof). In certain embodiments, for example, the stable, homogenous, nebulizable budesonide composition may be a stable, homogenous, nebulizable budesonide composition which introduces no additional side effects when inhaled compared to a nebulizable suspension of budesonide at the same active ingredient composition (for example introduces no additional side effects when inhaled into the stomach compared to a nebulizable suspension of budesonide at the same active ingredient composition).

Certain embodiments may provide, for example, a stable, benzalkonium chloride-free aqueous composition comprising a polyvinyl caprolactam-polyvinyl acetate-polyethylene glycol graft copolymer and 0.00625-0.3 wt. % budesonide. In certain embodiments, for example, the stable, benzalkonium chloride-free aqueous composition may provide a unit dose of a therapeutic quantity of the budesonide using a vibrating mesh nebulizer (for example a battery-powered, hand-held nebulizer). In certain embodiments, for example, the stable, benzalkonium chloride-free aqueous composition may provide a unit dose of a therapeutic quantity of the budesonide using a Pari™ LC Jet Plus Nebulizer (with a face mask or mouthpiece) connected to a Pari™ Master compressor.

Certain embodiments may provide, for example, a stable, homogeneous budesonide composition. In certain embodiments, for example, the composition may comprise in the range of 25-3000 mcg budesonide per 2 mL (12.5-1500 mcg/mL) of the homogenous budesonide composition (for example in the range of 150-350 mcg budesonide per 2 mL of the homogenous budesonide composition, in the range of 200-300 mcg budesonide per 2 mL of the homogenous budesonide composition, in the range of 225-275 mcg budesonide per 2 mL of the homogenous budesonide composition, in the range of 175-300 mcg budesonide per 2 mL of the homogenous budesonide composition, in the range of 200-275 mcg budesonide per 2 mL of the homogenous budesonide composition, in the range of 225-325 mcg budesonide per 2 mL of the homogenous budesonide composition, in the range of 240-260 mcg budesonide per 2 mL of the homogenous budesonide composition, in the range of 375-675 mcg budesonide per 2 mL of the homogenous budesonide composition, in the range of 400-600 mcg budesonide per 2 mL of the homogenous budesonide composition, in the range of 450-550 mcg budesonide per 2 mL of the homogenous budesonide composition, in the range of 475-525 mcg budesonide per 2 mL of the homogenous budesonide composition, in the range of 400-575 mcg budesonide per 2 mL of the homogenous budesonide composition, in the range of 450-525 mcg budesonide per 2 mL of the homogenous budesonide composition, in the range of 475-600 mcg budesonide per 2 mL of the homogenous budesonide composition, or in the range of 475-515 mcg budesonide per 2 mL of the homogenous budesonide composition, or 125, 250, 375, 500, 625, 750 or 1000 mcg budesonide per 2 mL of the homogeneous budesonide composition), a polyvinyl caprolactam-polyvinyl acetate-polyethylene glycol graft copolymer, present at a weight ratio of less than (or no more than) 5:1 (for example less than (or no more than) 4:1 or less than (or no more than) 2:1) relative to the weight of budesonide in the homogeneous budesonide composition, and at least 90 wt. % water. In certain embodiments, for example, the homogeneous budesonide composition may be a solution. In certain embodiments, for example, the homogeneous budesonide composition may be a dispersion (for example a microdispersion or a nanodispersion). In certain embodiments, for example, less than 37.5 mg (for example in the range of 10-30 mg, in the range of 5-20 mg, or in the range of 12.5-25 mg) of the homogeneous budesonide composition may be retained by an 0.2 micron filter per 1 L of the composition passed through the filter, for example less than 25 mg, less than 12.5 mg, less than 6.25 mg, or less than 1 mg of the homogeneous budesonide composition may be retained by an 0.2 micron filter per 1 L of the homogeneous budesonide composition passed through the filter. In certain embodiments, for example, less than 75 mg (for example in the range of 20-60 mg, in the range of 10-40 mg, or in the range of 25-50 mg) of the homogeneous budesonide composition may be retained by an 0.05 micron filter per 1 L of the homogeneous budesonide composition passed through the filter, for example less than 35 mg, less than 17.5 mg, less than 12.5 mg, or less than 1 mg of the homogeneous budesonide composition may be retained by an 0.05 micron filter per 1 L of the homogeneous budesonide composition passed through the filter. In certain embodiments, for example, at least 90% of 0.5 micron wavelength light may be transmitted through 0.1 meters of the homogeneous budesonide composition, for example at least 95%, 98%, at least 99%, or at least 99.5% of 0.5 micron wavelength light may be transmitted through 0.1 meters of the homogeneous budesonide composition.

In certain embodiments, for example, the composition may be nebulized (for example using a vibrating mesh nebulizer) to form droplets having an average size in the range of 0.5-10 microns (for example 1-5 microns, 2-5 microns, 3-5 microns, or 1-6 microns). In certain embodiments, for example, the composition may further comprise polysorbate 80. In certain further embodiments, for example, the polysorbate 80 may be present at a weight ratio of less than (or no more than) 5:1 (for example less than (or no more than) 4:1, such as less than (or no more than) 3:1 or less than (or no more than) 2:1) relative to the weight of budesonide in the composition. In certain embodiments, for example, the composition may have a combined polysorbate 80 and polyvinyl caprolactam-polyvinyl acetate-polyethylene glycol graft copolymer content present at a weight ratio of less than (or no more than) 5:1 (for example less than (or no more than) 4:1, such as less than (or no more than) 3:1 or less than (or no more than) 2:1) relative to the weight of budesonide in the composition. In certain embodiments, for example, the composition may have a polysorbate 80 concentration that falls within limits defined by the United States Food and Drug Administration Inactive Ingredients Database and/or Inactive Ingredient Guide (for example, falling within pharmaceutically accepted limits).

Certain embodiments may provide, for example, a stable, homogeneous budesonide composition comprising in the range of 125-3000 mcg budesonide per 2 mL (62.5-1500 mcg/mL) of the homogenous budesonide composition (for example 125, 500, or 1000 mcg budesonide per 2 mL of the homogeneous budesonide composition), the stable, homogeneous budesonide composition exclusive of preservatives (for example exclusive of preservatives such as benzalkonium chloride, polyhexamethylene biguanide, benzoic acid, and benzoates). In certain further embodiments, for example, the budesonide may be completely dissolved in the composition. In certain embodiments, for example, the budesonide may have a particle size of less than 100 nm (for example less than 25 nm).

Certain embodiments may provide, for example, a stable 250 mcg/mL budesonide solution comprising budesonide, one or more alcohols (for example less than 10 wt. % of one or more alcohols, such as less than 5 wt. % of one or more alcohols), a polyvinyl caprolactam-polyvinyl acetate-polyethylene glycol graft copolymer, and iv) less than 600 mcg polysorbate 80 (for example less than 400 mcg polysorbate 80) per mL of the solution.

Certain embodiments may provide, for example, a stable budesonide solution consisting of 250 mcg budesonide per mL of the solution, a polyvinyl caprolactam-polyvinyl acetate-polyethylene glycol graft copolymer, less than 600 mcg polysorbate 80 (for example in the range of 500-580 mcg polysorbate 80) per mL of the solution, and a benzalkonium chloride-free aqueous buffer solution.

Certain embodiments may provide, for example, an pharmaceutical composition (for example an aqueous pharmaceutical composition) comprising budesonide, a polyvinyl caprolactam-polyvinyl acetate-polyethylene glycol graft copolymer, polysorbate 80, citric acid, and sodium citrate, and less than 0.01 wt. % ethylenediaminetetraacetic acid. In certain further embodiments, for example, the pharmaceutical composition may be exclusive of benzalkonium chloride.

Certain embodiments may provide, for example, a stable, homogeneous budesonide composition comprising at least 0.01 wt. % budesonide, less than 1.0 wt. % polyvinyl caprolactam-polyvinyl acetate-polyethylene glycol graft copolymer, and at least 25 wt. % water. In certain embodiments, for example, the composition may be a master batch. In certain embodiments, for example, a portion or all of the master batch may be diluted to form a stable, homogeneous drug product (for example a drug product solution or a drug product nanodispersion) having a therapeutic concentration of budesonide that is a lower concentration than the concentration of budesonide present in the master batch.

In certain embodiments, one or more than one (including for instance all) of the following embodiments may comprise each of the embodiments or parts thereof. In certain embodiments, for example, any one of the foregoing compositions may be precipitate-free. In certain embodiments, for example, any one of the foregoing compositions may be solids-free. In certain embodiments, for example, any one of the foregoing compositions may be preservative-free. In certain embodiments, for example, any one of the foregoing compositions may be benzalkonium chloride-free. In certain embodiments, for example, any one of the foregoing compositions may have a pH in the range of 3-6 (for example in the range of 4-5). In certain embodiments, for example, any one of the foregoing compositions may form less than 0.008 wt. % precipitate after being stored for 3 months at a temperature of 25° C. In certain embodiments, for example, any one of the foregoing compositions may be clear. In certain embodiments, for example, any one of the foregoing compositions may be colorless. In certain embodiments, for example, any one of the foregoing compositions may be foam-free. In certain embodiments, for example, any one of the foregoing compositions may be sterile and/or pyrogen-free. In certain embodiments, for example, a homogeneous budesonide composition may pass one or more laboratory tests for sterility conducted in accordance with U.S. Pharmacopeia <71>.

In certain embodiments, one or more than one (including for instance all) of the following embodiments may comprise each of the embodiments or parts thereof. In certain embodiments, for example, any one of the foregoing compositions may comprise an aqueous buffer solution. In certain further embodiments, for example, the buffer solution may comprise a stabilizer (for example ethylenediaminetetraacetic acid (EDTA) or a sodium salt such as sodium edetate or a magnesium salt such as magnesium chloride). In certain embodiments, for example, the buffer solution may comprise citric acid. In certain embodiments, for example, the buffer solution may comprise sodium citrate. In certain embodiments, for example, the buffer solution may comprise sodium chloride. In certain embodiments, for example, the aqueous buffer solution may be formed by combining in the range of 0.001-0.1 wt. % EDTA (for example 0.01 wt. % EDTA), relative to the total weight of the buffer solution, in the range of 0.005-0.5 wt. % citric acid anhydrous (for example 0.056 wt. % citric acid anhydrous), relative to the total weight of the buffer solution, in the range of 0.005-0.5 wt. % sodium citrate dihydrate (for example 0.048 wt. % sodium citrate dihydrate), relative to the total weight of the buffer solution, in the range of 0.05-5 wt. % sodium chloride (for example 0.8635 wt. % sodium chloride), relative to the total weight of the buffer solution, and water.

Certain embodiments may provide, for example, a homogeneous pharmaceutical composition comprising budesonide, a polyvinyl caprolactam-polyvinyl acetate-polyethylene glycol graft copolymer, polysorbate 80, less than 0.01 wt. % EDTA, citric acid, and sodium citrate, wherein the homogeneous, pharmaceutical composition is exclusive of benzalkonium chloride.

Certain embodiments may provide, for example, a method to prepare a precipitate-free budesonide composition, comprising a) dispersing (for example dissolving), in a volume of a first liquid a quantity of budesonide particulate (for example a powder, such as a budesonide micronized powder) followed by a quantity of polyvinyl caprolactam-polyvinyl acetate-polyethylene glycol graft copolymer, (a useful embodiment of this graft copolymer is sold under the SOLUPLUS trademark from BASF SE) to form budesonide-containing first liquid, and b) mixing a volume of a second liquid with the budesonide-containing first liquid to form the precipitate-free budesonide solution. In certain embodiments, for example, the first liquid may comprise propylene glycol and/or ethanol. In certain embodiments, for example, the second liquid may comprise polysorbate 80 dissolved in a buffer solution. In certain embodiments, for example, the method may be exclusive of "homogenization." In certain embodiments, for example, the budesonide composition may be a solution. In certain embodiments, for example, the budesonide composition may be a nanodispersion. In certain embodiments, for example, the budesonide particulate may be a budesonide micronized powder having an average particle size of less than 5 microns (for example less than 1 micron). In certain embodiments, for example, the budesonide particulate may have an average particle size of at least 25 microns (for example at least 50 microns or at least 100 microns). In certain embodiments, for example, the budesonide particulate may have a purity of at least 98 wt. % budesonide relative to the total weight of the particulate (for example at least 99 wt. %, such as at least 99.9 wt. %, at least 99.99 wt. %, or at least 99.999 wt. % budesonide). In certain embodiments, for example, the budesonide particulate may have a budesonide purity of less than 99.9 wt. % budesonide relative to the total weight of the particulate (for example less than 99 wt. %, less than 98 wt. %, less than 97 wt. %, or less than 95 wt. % budesonide). In certain embodiments, for example, the budesonide particulate may have an average particle size of less than 5 microns and a purity of at least 99 wt. % budesonide relative to the total weight of the particulate. In certain embodiments, for example, the budesonide particulate may have an average particle size of at least 25 microns and a purity of less than 98 wt. % budesonide relative to the total weight of the particulate. In certain embodiments, for example, the budesonide-containing first liquid may be clear. In certain embodiments, for example, the budesonide-containing first liquid may be colorless. In certain embodiments, for example, the quantity of budesonide particulate and the quantity of polyvinyl caprolactam-polyvinyl acetate-polyethylene glycol graft copolymer may be completely dissolved in the budesonide-containing first liquid. In certain further embodiments, for example, the budesonide particulate and the polyvinyl caprolactam-polyvinyl acetate-polyethylene glycol graft copolymer may comprise a nanodispersion in the budesonide-containing first liquid. In certain embodiments, for example, the budesonide-containing first liquid may be precipitate-free. In certain embodiments, for example, the budesonide-containing first liquid may be solids-free. In certain embodiments, for example, the ratio of the quantity of the budesonide particulate to the volume of the first liquid may be less than 10 mg/mL (for example the ratio may be 5 mg/mL). In certain embodiments, for example, the first liquid may be an alcohol. In certain embodiments, for example, the first liquid may be propylene glycol. In certain embodiments, for example, the first liquid may be ethanol. In certain embodiments, for example, the first liquid may be a blend of propylene glycol and ethanol. In certain embodiments, for example, the budesonide-containing first liquid may be exclusive of polyethylene glycol. In certain embodiments, for example, the ratio of the quantity of the polyvinyl caprolactam-polyvinyl acetate-polyethylene glycol graft copolymer to the volume of the first liquid may be less than 10 mg/mL (for example the ratio may be 6 mg/mL).

In certain embodiments, for example, the second liquid may be clear. In certain embodiments, for example, the second liquid may be colorless. In certain embodiments, for example, the second liquid may comprise a surfactant. The surfactant may be dissolved (for example, completely dissolved) in the second liquid. In certain embodiments, for example, the quantity of polysorbate 80 may be dissolved (for example, completely dissolved) in the second liquid. In certain embodiments, for example, the second liquid may be substantially precipitate-free (for example, precipitate-free). In certain embodiments, for example, the second liquid may be substantially solids-free (for example, solids-free). In certain embodiments, for example, the ratio of the quantity of polysorbate 80 to the volume of buffer in the second liquid may be 20 mg/mL. In certain embodiments, for example, the budesonide composition solution may be clear. In certain embodiments, for example, the budesonide composition may be colorless. In certain embodiments, for example, the budesonide composition may be solids-free. In certain embodiments, for example, the budesonide composition may be foam-free. In certain embodiments, for example, the budesonide composition may be stable (for example: less than 5% of the budesonide present in the budesonide composition may decompose after at least 3 months at 25° C., no observable precipitate may be present in the budesonide composition for at least 1 year at 25° C., the budesonide composition may remain pharmaceutically acceptable for least 1 year at 25° C., the budesonide composition may remain homogeneous for least 1 year at 25° C., the budesonide composition may remain sterile for least 1 year at 25° C., and/or the budesonide composition may remain solids-free for at least 1 year at 25° C.). In certain embodiments, for example, the budesonide composition may have budesonide concentration in the range of 1-10 mg/mL (for example 3.57 mg/mL). In certain embodiments, for example, the budesonide composition may be sterile. In certain embodiments, for example, the mixing may be vigorous. In certain embodiments, for example, the mixing may be low shear mixing. In certain embodiments, for example, the mixing may be high shear mixing.

In certain embodiments, for example, the polyvinyl caprolactam-polyvinyl acetate-polyethylene glycol graft copolymer may be introduced, in a solid state, to the volume of a first liquid to form the dispersion. In certain embodiments, for example, the polyvinyl caprolactam-polyvinyl acetate-polyethylene glycol graft copolymer may be introduced, in a liquid state, to the volume of a first liquid to form the dispersion. In certain embodiments, for example, the polyvinyl caprolactam-polyvinyl acetate-polyethylene glycol graft copolymer may be introduced, in a solid state, as part of a mixture to the volume of a first liquid to form the dispersion. In certain further embodiments, for example, the mixture may comprise one or more excipients. In certain embodiments, for example, the polyvinyl caprolactam-polyvinyl acetate-polyethylene glycol graft copolymer may be introduced, in a liquid state, as part of a mixture to the volume of a first liquid to form the dispersion. In certain further embodiments, for example, the mixture may comprise one or more excipients.

In certain embodiments, for example, the polysorbate 80 may be introduced, in a solid state, to the buffer to form the second liquid. In certain embodiments, for example, the polysorbate 80 may be introduced, in a liquid state, to the buffer to form the second liquid. In certain embodiments, for example, the polysorbate 80 may be introduced, in a solid state, as part of a mixture to the buffer to form the second liquid. In certain further embodiments, for example, the mixture may comprise one or more excipients. In certain embodiments, for example, the polysorbate 80 may be introduced, in a liquid state, as part of a mixture to the buffer to form the second liquid. In certain further embodiments, for example, the mixture may comprise one or more excipients.

Certain embodiments may provide, for example, a method to prepare a volume of a drug product composition (for example a dispersion, inclusive of a solution or a nanodispersion), comprising diluting a volume of the precipitate-free budesonide composition a volume of buffer solution (for example any of the aqueous buffers disclosed herein). In certain embodiments, for example, the volume of budesonide drug product solution may be precipitate-free and/or solids-free. In certain embodiments, for example, the volume of drug product solution may be preservative-free (for example free of benzalkonium chloride). In certain embodiments, for example, the volume of drug product solution may be complexing agent-free (for example free of ethylenediaminetetraacetic acid). In certain embodiments, for example, the concentration of budesonide in the volume of drug product solution may be 125 mcg/mL. In certain embodiments, for example, the concentration of budesonide in the volume of drug product solution may be 250 mcg/mL. In certain embodiments, for example, the concentration of budesonide in the volume of drug product solution may be 500 mcg/mL. In certain embodiments, for example, the method may further comprise sterile filtration of the diluted volume of the precipitate-free budesonide composition. In certain embodiments, for example, the method may further comprise sterile filtration of the drug product solution. In certain embodiments, for example, the method may be exclusive of "homogenization." In certain embodiments, for example, the method may comprise mixing the diluted volume of the precipitate-free budesonide composition under low shear for at least 30 minutes, for example at least 45 minutes, at least 60 minutes, at least 90 minutes, or the method may comprise the method may comprise mixing the diluted volume of the precipitate-free budesonide composition under low shear for at least 120 minutes. In certain embodiments, for example, the method may comprise mixing the diluted volume of the precipitate-free budesonide composition under low shear for a period of time in the range of 60-180 minutes, for example in the range of 90-150 minutes, or for a period of time of 120 minutes.

Certain embodiments may provide, for example, a method to prepare a volume of a homogeneous budesonide composition (for example a drug product solution) that does not require forming a master batch. In certain embodiments, for example, the method may comprise directly adding quantities of budesonide and quantities of polyvinyl caprolactam-polyvinyl acetate-polyethylene glycol graft copolymer to aqueous buffer, followed by adding a second solution comprising budesonide and propylene glycol to the buffer. In certain embodiments, for example, the propylene glycol concentration may be in the range of 5-20 wt. % (for example 15 wt. %) relative to the weight of the homogeneous budesonide composition. In certain embodiments, for example, the homogeneous budesonide composition may comprise 0.00625-0.3 wt. % budesonide. In certain embodiments, for example, the homogeneous budesonide composition may comprise 125 mcg/mL budesonide solution (250 mcg budesonide per 2 mL of the composition). In certain embodiments, for example, the homogeneous budesonide composition may comprise 250 mcg/mL budesonide solution (500 mcg budesonide per 2 mL of the composition). In certain embodiments, for example, the homogeneous budesonide composition may comprise 500 mcg/mL budesonide solution (1000 mcg budesonide per 2 mL of the composition). In certain embodiments, for example, the homogeneous budesonide composition may comprise polyvinyl caprolactam-polyvinyl acetate-polyethylene glycol graft copolymer, present at a weight ratio of less than (or no more than) 5:1 (for example less than (or no more than) 4:1, less than (or no more than) 3:1 or less than (or no more than) 2:1) relative to the weight of budesonide in the composition.

In any of the foregoing methods, for example, preparation of the drug product composition may comprise adjusting the pH of the diluted volume of the precipitate-free budesonide composition, for example by adding citric acid, sodium citrate, and/or hydrochloric acid (for example by mixing the diluted volume of the precipitate-free budesonide composition with an aqueous solution comprising citric acid, sodium citrate, and/or hydrochloric acid). In certain embodiments, for example, the pH of the precipitate-free budesonide composition may be adjusted to a target pH (for example a pH in the range of 3-5 (for example a pH in the range of 4-5, such as 4.5) by adding a quantity of 10% citric acid solution or 10% sodium citrate. In certain embodiments, for example, the adjusted pH may be in the range of 2-6, for example in the range of 3-5 (such as a pH of 4.5).

Certain embodiments may provide, for example, a drug product comprising a sterile volume of any one of the foregoing compositions in a container (for example a plastic container such as a low-density polyethylene container). In certain embodiments, for example, the sterile volume of the any one of the foregoing compositions may be a single dose. In certain embodiments, for example, the container may be a single-use container. In certain embodiments, for example, the container may be sized to contain a single dose of the any one of the foregoing compositions. In certain embodiments, for example, the container may be formed by a blow-fill-seal process (for example a single use, blow-fill-seal container with a twist-off top formed by a blow-fill-seal process). In certain embodiments, for example, the product may further comprise a label, the label disclosing a budesonide drug product solution concentration of 0.25 mg/2 mL. In certain embodiments, for example, the product may further comprise a label, the label disclosing a budesonide drug product solution concentration of 0.5 mg/2 mL. In certain embodiments, for example, the product may further comprise a label, the label disclosing a budesonide drug product solution concentration of 1 mg/2 mL.

Certain embodiments may provide, for example, an aseptic process to make a drug product, comprising injecting a volume of any one of the foregoing homogeneous budesonide compositions into a sterile blow-fill-seal container or partially formed container (for example a container in the process of being formed), and sealing the sterile blow-fill-seal container. In certain embodiments, for example, the blow-fill-seal container may be formed from molten plastic at a temperature above where micro-organisms can survive in a sterile chamber, whereby the formed blow-fill-seal container may be sterile. In certain embodiments, for example, the molten plastic may be at a temperature in the range of 170-193° C. In certain embodiments, for example, the process may be exclusive of sterilization (for example exclusive of heat sterilization) following the sealing. In certain further embodiments, for example, the blow-fill-seal container and the homogeneous budesonide composition disposed therein may be sterile (for example due to being formed in a sterile chamber), and may remain sterile for an extended period (for example at least 24 months) even if the process may be exclusive of heat sterilization following the sealing. In certain embodiments, for example, the blow-fill-seal container may be impermeable to air. In certain further embodiments, for example, the blow-fill-seal container may be permeable to air or at least one component thereof. In certain embodiments, for example, the blow-fill-seal container may be impermeable to micro-organisms, inclusive of bacteria and viruses. In certain embodiments, for example, the process may further comprise impressing an electronic batch data code (for example cipher text) onto the sterile blow-fill-seal container. In certain embodiments, for example, the electronic batch data code referenced by the electronic batch data code may be configured for distributed ledger processing (for example the electronic batch data or ciphertext thereof may be included in a blockchain or other distributed ledger technology). In certain embodiments, for example, a blow-fill-seal method may comprise impressing an electronic batch data code (for example ciphertext) onto a blow-fill-seal container. In certain embodiments, for example, the electronic batch data referenced by the electronic batch data code may be configured for distributed ledger processing (for example the electronic batch data or a ciphertext thereof may be included in a blockchain or a distributed ledger technology).

In certain further embodiments, for example, the process may further comprise sterile filtration of the any one of the homogeneous budesonide compositions disclosed herein prior to introduction to the blow-fill-seal container. In certain embodiments, for example, the sterile filtration may comprise microfiltration using one or more filters (for example the one or more filters may comprise a membrane filter). In certain embodiments, for example, the one or more filters may have a pore size of less than 1 micron, for example less than 0.5 microns, less than 0.2 microns, less than 0.1 micron, or the one or more filters may have a pore size of less than 0.05 microns. In certain embodiment, for example, the one or more filters may have a pore size in the range of 0.05-1 microns, for example in the range of 0.1-0.5 microns, in the range of 0.15-0.3 microns, or the one or more filters may have a pore size in the range of 0.19-0.25 microns. In certain embodiments, for example, any of the foregoing one or more filters may be a pre-filter. In certain embodiments, for example, the one or more filters may have a pore size of less than 100 nm, for example less than 75 nm, less than 50 nm, less than 30 nm, or the one or more filters may have a pore size of less than 20 nm. In certain embodiment, for example, the one or more filters may have a pore size in the range of 1-100 nm, for example in the range of 10-75 nm, in the range of 20-50 nm, or the one or more filters may have a pore size in the range of 30-50 nm. In certain embodiments, for example, the one or more filters may comprise mixed cellulose ester. In certain embodiments, for example, the one or more filters may be a polyvinylidene fluoride (PVDF) filter (for example an 0.2 micron PVDF filter). In certain embodiments, for example, the one or more filters may comprise polyethersulfone (PES). In certain embodiments, for example, the one or more filters may comprise a pre-sterilized disposable unit. In certain further embodiments, for example, the pre-sterilized disposable unit may be provided in a sealed package. In certain embodiments, for example, the one or more filters may be sterilized (for example by autoclaving at a temperature that does not damage the filter). In certain embodiments, for example, the one or more filters may be tested for integrity and/or sterility prior to use. In certain embodiments, for example, the one or more filters may be tested for integrity and/or sterility after use. In certain embodiments, for example, the sterile filtration may be performed in a clean room. In certain further embodiments, for example, the clean room may have no more than 1,000,000 particles, per cubic meter, having a size larger than 0.5 microns, for example no more than 100,000 particles per cubic meter, for example no more than 10,000 particles per cubic meter, for example no more than 5,000 particles per cubic meter, no more than 2,500 particles per cubic meter, no more than 2,000 particles per cubic meter, no more than 1,000 particles per cubic meter, no more than 100 particles per cubic meter, no more than 50 particles per cubic meter, no more than 12 particles per cubic meter, or the clean room may have fewer than 1000 particles, per cubic meter, having a size larger than 0.5 microns. In certain embodiments, for example, the clean room may be an ISO class 5 clean room. In certain embodiments, for example, the clean room may be an ISO class 4 clean room. In certain embodiments, for example, the clean room may be an ISO class 3 clean room. In certain embodiments, for example, the clean room may be an ISO class 2 clean room. In certain embodiments, for example, the clean room may be an ISO class 1 clean room. In certain embodiments, for example, air entering the clean room may be passed through a high-efficiency particulate air (HEPA) filter prior to entering the clean room. In certain embodiments, for example, air entering the clean room may be passed through a high-efficiency particulate air (HEPA) filter prior to entering the clean room. In certain embodiments, for example, air entering the clean room may be passed through an ultra-low particulate air (ULPA) filter.

In certain embodiments, for example, the sterile filtration of the homogeneous budesonide solution may remove at least 95 wt. % of microorganisms or other pathogens present in the homogeneous budesonide solution prior to the sterile filtration, for example at least 99 wt. %, 99.9 wt. %, 99.99 wt. %, 99.999 wt. %, 99.9999 wt. %, 99.99999 wt. %, 99.999999 wt. %, 99.9999999 wt. %, or the sterile filtration of the homogeneous budesonide solution may remove at least 99.99999999 wt. % of microorganisms or other pathogens present in the homogeneous budesonide solution prior to the sterile filtration Certain embodiments may provide, for example, a method of treating, preventing, or ameliorating one or more symptoms of a bronchoconstriction-related disease or disorder, comprising nebulizing, by a nebulizer, a unit dose of any one of the homogeneous budesonide compositions disclosed herein. In certain embodiments, for example, the unit dose may be nebulized by a vibrating mesh nebulizer. In certain embodiments, for example, the nebulizer may be a handheld, battery powered nebulizer. In certain embodiments, for example, the method may further comprise providing the unit dose to the nebulizer from a single use, blow-fill-seal container.

Certain embodiments may provide, for example, a stable, homogeneous budesonide composition comprising: i) at least 0.01 wt. % budesonide; ii) less than 1.0 wt. % polyvinyl caprolactam-polyvinyl acetate-polyethylene glycol graft copolymer, present at a weight ratio of less than 2:1 relative to the weight of budesonide in the composition; and iii) at least 25 wt. % water.

Certain embodiments may provide, for example, a stable, homogeneous budesonide composition comprising: i) 0.00625-0.05 wt. % budesonide; ii) a polyvinyl caprolactam-polyvinyl acetate-polyethylene glycol graft copolymer, present at a weight ratio of less than (or no more than) 4:1 (for example less than (or no more than) 2:1) relative to the weight of budesonide in the composition; and iii) at least 90 wt. % water.

Certain embodiments may provide, for example, a stable, homogeneous budesonide composition comprising: i) 0.00625-0.3 wt. % budesonide, the budesonide being completely dissolved or having a particle size of less than 10 nm; and ii) at least 90 wt. % water, wherein the stable, homogeneous budesonide composition may be exclusive of benzalkonium chloride.

Certain embodiments may provide, for example, a stable 125 mcg/mL budesonide solution (250 mcg budesonide per 2 mL of the composition) comprising: i) budesonide; ii) one or more alcohols; iii) a polyvinyl caprolactam-polyvinyl acetate-polyethylene glycol graft copolymer; and iv) less than 400 mcg polysorbate 80 per mL of the solution.

Certain embodiments may provide, for example, a stable 250 mcg/mL budesonide solution (500 mcg budesonide per 2 mL of the composition) comprising: i) budesonide; ii) one or more alcohols; iii) a polyvinyl caprolactam-polyvinyl acetate-polyethylene glycol graft copolymer; and iv) less than 400 mcg polysorbate 80 per mL of the solution.

Certain embodiments may provide, for example, a stable 500 mcg/mL budesonide solution (1000 mcg budesonide per 2 mL of the composition) comprising: i) budesonide; ii) one or more alcohols; iii) a polyvinyl caprolactam-polyvinyl acetate-polyethylene glycol graft copolymer; and iv) less than 400 mcg polysorbate 80 per mL of the solution.

Certain embodiments may provide, for example, a stable budesonide solution consisting of: i) 125 mcg budesonide per mL of the solution (250 mcg budesonide per 2 mL of the solution); ii) a polyvinyl caprolactam-polyvinyl acetate-polyethylene glycol graft copolymer; iii) less than 600 mcg polysorbate 80 per mL of the solution; and iv) a benzalkonium chloride-free aqueous buffer solution. In certain embodiments, for example, the stable budesonide solution may comprise less than 375 mcg polyvinyl caprolactam-polyvinyl acetate-polyethylene glycol graft copolymer per mL of the solution.

Certain embodiments may provide, for example, a stable budesonide solution consisting of: i) 250 mcg budesonide per mL of the solution (500 mcg budesonide per 2 mL of the solution); ii) a polyvinyl caprolactam-polyvinyl acetate-polyethylene glycol graft copolymer; iii) less than 600 mcg polysorbate 80 per mL of the solution; and iv) a benzalkonium chloride-free aqueous buffer solution. In certain embodiments, for example, the stable budesonide solution may comprise less than 750 mcg polyvinyl caprolactam-polyvinyl acetate-polyethylene glycol graft copolymer per mL of the solution.

Certain embodiments may provide, for example, a stable budesonide solution consisting of: i) 500 mcg budesonide per mL of the solution (1000 mcg budesonide per 2 mL of the solution); ii) a polyvinyl caprolactam-polyvinyl acetate-polyethylene glycol graft copolymer; iii) less than 1000 mcg polysorbate 80 per mL of the solution; and iv) a benzalkonium chloride-free aqueous buffer solution. In certain embodiments, for example, the stable budesonide solution may comprise less than 1500 mcg polyvinyl caprolactam-polyvinyl acetate-polyethylene glycol graft copolymer per mL of the solution.

Certain embodiments may provide, for example, a method to prepare a precipitate-free budesonide solution, comprising: i) dissolving, in a volume of a first liquid, a) a quantity of budesonide particulate (for example a powder such as a budesonide micronized powder); followed by b) a quantity of polyvinyl caprolactam-polyvinyl acetate-polyethylene glycol graft copolymer, to form budesonide-containing first liquid; and ii) mixing a volume of a second liquid with the budesonide-containing first liquid to form the budesonide solution, wherein the first liquid comprises: propylene glycol and/or ethanol; and the second liquid comprises: polysorbate 80 dissolved in a buffer solution.

Certain embodiments may provide, for example, a stable, homogeneous (substantially uniformly or uniformly dispersed) budesonide dispersion comprising in the range of 0.00625-0.3 wt. % (for example 0.0125-0.05 wt. %) budesonide, and at least 90 wt. % water, the stable, homogeneous budesonide dispersion exclusive of a preservative (for example benzalkonium chloride). In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) 125 mcg/mL budesonide dispersion (250 mcg per 2 mL of the dispersion) comprising budesonide, one or more alcohols (for example less than 5 wt. % of one or more alcohols), a polyvinyl caprolactam-polyvinyl acetate-polyethylene glycol graft copolymer, and iv) less than 400 mcg polysorbate 80 per mL of the dispersion. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) 250 mcg/mL budesonide dispersion (500 mcg per 2 mL of the dispersion) comprising budesonide, one or more alcohols (for example less than 15 wt. % of one or more alcohols), a polyvinyl caprolactam-polyvinyl acetate-polyethylene glycol graft copolymer, and iv) less than 400 mcg polysorbate 80 per mL of the dispersion. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) 500 mcg/mL budesonide dispersion (1000 mcg per 2 mL of the dispersion) comprising budesonide, one or more alcohols (for example less than 15 wt. % of one or more alcohols), a polyvinyl caprolactam-polyvinyl acetate-polyethylene glycol graft copolymer, and iv) less than 400 mcg polysorbate 80 per mL of the dispersion. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) budesonide dispersion consisting of 125 mcg budesonide per mL of the dispersion (250 mcg per 2 mL of the dispersion), a polyvinyl caprolactam-polyvinyl acetate-polyethylene glycol graft copolymer, less than 580 mcg polysorbate 80 per mL of the dispersion, and a benzalkonium chloride-free aqueous buffer solution. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) budesonide dispersion consisting of 250 mcg budesonide per mL of the dispersion (500 mcg per 2 mL of the dispersion), a polyvinyl caprolactam-polyvinyl acetate-polyethylene glycol graft copolymer, less than 580 mcg polysorbate 80 per mL of the dispersion, and a benzalkonium chloride-free aqueous buffer solution. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) budesonide dispersion consisting of 500 mcg budesonide per mL of the dispersion (1000 mcg per 2 mL of the dispersion), a polyvinyl caprolactam-polyvinyl acetate-polyethylene glycol graft copolymer, less than 1200 mcg polysorbate 80 per mL of the dispersion, and a benzalkonium chloride-free aqueous buffer solution. In certain further embodiments, for example, the budesonide may be completely dissolved in the dispersion. In certain embodiments, for example, the budesonide may have a particle size of less than 100 nm (for example less than 25 nm).

Certain embodiments may provide, for example, a stable homogeneous (substantially uniformly or uniformly dispersed) budesonide dispersion comprising 125 mcg budesonide per mL of the dispersion (250 mcg per 2 mL of the dispersion), in the range of 60-250 mcg polyvinyl caprolactam-polyvinyl acetate-polyethylene glycol graft copolymer per mL of the dispersion, in the range of 50-350 mcg polysorbate 80 per mL of the dispersion, and a benzalkonium chloride-free aqueous buffer solution. In certain further embodiments, for example, the dispersion may comprise in the range of 500-15,000 mcg of one or more alcohols per mL of the dispersion. In certain further embodiments, for example, the one or more alcohols may comprise propylene glycol. In certain embodiments, for example, the budesonide may be completely dissolved in the dispersion. In certain embodiments, for example, the budesonide may have a particle size of less than 100 nm (for example less than 25 nm) in the dispersion.

Certain embodiments may provide, for example, a stable homogeneous (substantially uniformly or uniformly dispersed) budesonide dispersion comprising 250 mcg budesonide per mL of the dispersion (500 mcg per 2 mL of the dispersion), in the range of 125-500 mcg polyvinyl caprolactam-polyvinyl acetate-polyethylene glycol graft copolymer per mL of the dispersion, in the range of 100-700 mcg polysorbate 80 per mL of the dispersion, and a benzalkonium chloride-free aqueous buffer solution. In certain further embodiments, for example, the dispersion may comprise in the range of 1000-15,000 mcg of one or more alcohols per mL of the dispersion. In certain further embodiments, for example, the one or more alcohols may comprise propylene glycol. In certain embodiments, for example, the budesonide may be completely dissolved in the dispersion. In certain embodiments, for example, the budesonide may have a particle size of less than 100 nm (for example less than 25 nm) in the dispersion.

Certain embodiments may provide, for example, a stable homogeneous (substantially uniformly or uniformly dispersed) budesonide dispersion comprising 500 mcg budesonide per mL of the dispersion (1000 mcg per 2 mL of the dispersion), in the range of 125-750 mcg polyvinyl caprolactam-polyvinyl acetate-polyethylene glycol graft copolymer per mL of the dispersion, in the range of 100-1100 mcg polysorbate 80 per mL of the dispersion, and a benzalkonium chloride-free aqueous buffer solution. In certain further embodiments, for example, the dispersion may comprise in the range of 1000-15,000 mcg of one or more alcohols per mL of the dispersion. In certain further embodiments, for example, the budesonide may be completely dissolved in the dispersion. In certain embodiments, for example, the budesonide may have a particle size of less than 100 nm (for example less than 25 nm) in the dispersion.

Certain embodiments may provide, for example, a stable, homogeneous budesonide composition comprising: 0.00625-0.3 wt. % (for example 0.0125-0.05 wt. %) budesonide, a polyvinyl caprolactam-polyvinyl acetate-polyethylene glycol graft copolymer present at a weight ratio of less than (or no more than) 5:1 (for example less than (or no more than) 4:1, less than (or no more than) 3:1, or less than (or no more than) 2:1), relative to the weight of budesonide in the composition, and at least 90 wt. % water. In certain embodiments, for example, the composition may further comprise polysorbate 80 present at a weight ratio of less than (or no more than) 2:1, relative to the budesonide concentration. In certain embodiments, for example, the composition may be benzalkonium chloride-free. In certain embodiments, for example, the composition may be stable (for example retain greater than 80%, 85%, or 95% of original budesonide content) following storage in a polyethylene container for 24 months at a temperature of 25° C. and 40% relative humidity. In certain embodiments, for example, the composition may be a solution. In certain embodiments, for example, the composition may be a nanodispersion. In certain embodiments, for example, the composition may form droplets having an average size in the range of 1-6 microns when passed through a Pari™ LC Jet Plus Nebulizer connected to a Pari™ Master compressor. Certain embodiments may provide, for example, a drug product comprising a sterile volume of one of the composition in a single dose, blow-fill-seal container. Certain embodiments may provide, for example, an aseptic process to form a drug product composition, comprising: injecting a volume of the composition into a sterile blow-fill-seal container, and sealing the sterile blow-fill-seal container. In certain embodiments, for example, the process may further comprise sterilizing the volume of the composition prior to the injecting. In certain embodiments, for example, the aseptic process may be exclusive of sterilization following the sealing. Certain embodiments may provide, for example, a method of treating, preventing, or ameliorating one or more symptoms of a bronchoconstriction-related disease or disorder, comprising: nebulizing, by a nebulizer, a unit dose of the composition.

Certain embodiments may provide, for example, a homogeneous, pharmaceutical composition comprising: at least 0.01 wt. % budesonide, less than 0.05 wt. % polyvinyl caprolactam-polyvinyl acetate-polyethylene glycol graft copolymer, less than 1 wt. % polysorbate 80, less than 0.01 wt. % ethylenediaminetetraacetic acid, citric acid, sodium citrate, and sodium chloride, the pharmaceutical composition exclusive of preservatives.

Certain embodiments may provide, for example, a method to prepare a precipitate-free composition, comprising: dispersing, in a volume of a first liquid, a quantity of budesonide particulate (for example a powder such as a budesonide micronized powder) followed by a quantity of polyvinyl caprolactam-polyvinyl acetate-polyethylene glycol graft copolymer to form a budesonide-containing first liquid, and mixing at least a portion of the budesonide-containing first liquid with a volume of a second liquid to form the precipitate-free composition.

Certain embodiments may provide, for example, a method to prepare a precipitate-free composition, comprising: forming a budesonide-containing first liquid, comprising: dispersing a quantity of budesonide particulate (for example a powder such as a budesonide micronized powder) in a volume of first liquid, forming a second liquid, comprising: dissolving a quantity of polyvinyl caprolactam-polyvinyl acetate-polyethylene glycol graft copolymer in a volume of water, and mixing at least a portion of the budesonide-containing first liquid with a volume of the second liquid for at least 30 minutes to form the precipitate-free composition, the precipitate-free composition comprising at least 90 wt. % water, wherein the method may be exclusive of high shear mixing. In certain embodiments, for example, the ratio of the quantity of polyvinyl caprolactam-polyvinyl acetate-polyethylene glycol graft copolymer to the quantity of budesonide particulate may be less than (or no more than) 5:1 (for example less than (or no more than) 4:1, such as less than (or no more than) 3:1 or less than (or no more than) 2:1). In certain embodiments, for example, the composition may be a solution. In certain embodiments, for example, the composition may be a nanodispersion. In certain embodiments, for example, the concentration of budesonide may be in the range of 125-1,500 mcg budesonide per 2 mL of the precipitate-free composition. In certain embodiments, for example, the first liquid may comprise propylene glycol and/or ethanol. In certain embodiments, for example, the second liquid may comprise polysorbate 80.

Certain embodiments may provide, for example, a homogeneous budesonide inhalation solution or nanodispersion consisting of: 0.035 wt. % a polyvinyl caprolactam-polyvinyl acetate-polyethylene glycol graft copolymer (for example SOLUPLUS), 0.056 wt. % citric acid anhydrous, 0.048 wt. % sodium citrate dihydrate, 0.8635 wt. % sodium chloride, 0.0125-0.025 wt. % budesonide, 0.058 wt. % polysorbate 80, 0-5 wt. % propylene glycol, and 0-5 wt. % ethanol.

Certain embodiments may provide, for example, a homogeneous budesonide composition that retains at least 85% active ingredient after 24 months at 25° C. and 40% relative humidity, the composition comprising: 0.00625-0.3 wt. % (for example 0.0125-0.05 wt. %) budesonide and a polyvinyl caprolactam-polyvinyl acetate-polyethylene glycol graft copolymer (for example SOLUPLUS), present at a weight ratio no more than 4:1, relative to the weight of budesonide in the composition, mixed exclusively by low shear mixing with at least 90 wt. % water.

Certain embodiments may provide, for example, a homogeneous budesonide composition that retains at least 85% active ingredient after 24 months at 25° C. and 40% relative humidity, the composition comprising: 0.00625-0.3 wt. % (for example 0.0125-0.05 wt. %) budesonide and a polyvinyl caprolactam-polyvinyl acetate-polyethylene glycol graft copolymer (for example SOLUPLUS), present at a weight ratio of no more than 4:1, relative to the weight of budesonide in the composition, and at least 90 wt. % water, the composition prepared without high shear mixing.

Certain embodiments may provide, for example, a homogeneous budesonide composition that retains at least 85% active ingredient after 24 months at 25° C. and 40% relative humidity, the composition comprising: 0.00625-0.3 wt. % (for example 0.0125-0.05 wt. %) budesonide and a polyvinyl caprolactam-polyvinyl acetate-polyethylene glycol graft copolymer (for example SOLUPLUS), present at a weight ratio of no more than 4:1, relative to the weight of budesonide in the composition, and at least 90 wt. % water. In certain embodiments, for example, the composition may be exclusive of cellulose-derived compounds. In certain embodiments, for example, the composition may be exclusive of cyclodextrines.

Certain embodiments may provide, for example, a homogeneous budesonide composition that retains at least 85% active ingredient after 24 months at 25° C. and 40% relative humidity, the composition comprising: 0.00625-0.3 wt. % (for example 0.0125-0.05 wt. %) budesonide and a polyvinyl caprolactam-polyvinyl acetate-polyethylene glycol graft copolymer (for example SOLUPLUS), present at a weight ratio of no more than 4:1, relative to the weight of budesonide in the composition, and at least 90 wt. % water, the composition exclusive of benzalkonium chloride, EDTA, cellulose derivatives, and cyclodextrines, the composition formed exclusive of high shear mixing.

Certain embodiments may provide, for example, a homogeneous budesonide composition comprising (or consisting or consisting essentially of) in the range of 0.01-0.05 wt. % budesonide, 0.01-0.1 wt. % of a polyvinyl caprolactam-polyvinyl acetate-polyethylene glycol graft copolymer (for example SOLUPLUS), 0.01-0.1 wt. % citric acid anhydrous, 0.01-0.1 wt. % sodium citrate dihydrate, 0.8-1 wt. % sodium chloride, 0.01-0.1 wt. % polysorbate 80, and 5-20 wt. % propylene glycol. In certain embodiments, for example, the budesonide may be present at a concentration in the range of 0.0125-0.025 wt. %, 0.015 wt. %, or 0.02 wt. %. In certain embodiments, for example, the budesonide may be present at a concentration of at least 0.01 wt. %, at least 0.02 wt. %, or at least 0.03 wt. %. In certain embodiments, for example, the budesonide may be present at a concentration of less than 0.01 wt. %, less than 0.02 wt. %, or less than 0.03 wt. %. In certain embodiments, for example, the polyvinyl caprolactam-polyvinyl acetate-polyethylene glycol graft copolymer may be present at a concentration in the range of 0.02-0.045 wt. %, for example in the range of 0.03-0.04 wt. %, 0.033 wt. %, 0.034 wt. %, 0.035 wt. %, 0.036 wt. %, or 0.037 wt. %. In certain embodiments, for example, the polyvinyl caprolactam-polyvinyl acetate-polyethylene glycol graft copolymer may be present at a concentration in the range of 0.05-0.075 wt. %, for example in the range of 0.06-0.07 wt. %, 0.065 wt. %, 0.066 wt. %, 0.067 wt. %, 0.068 wt. %, or 0.069 wt. %. In certain embodiments, for example, the polyvinyl caprolactam-polyvinyl acetate-polyethylene glycol graft copolymer may be present at a concentration in the range of 0.09-0.11 wt. %, for example in the range of 0.095-0.105 wt. %, 0.098 wt. %, 0.099 wt. %, 0.1 wt. %, 0.101 wt. %, or 0.102 wt. %. In certain embodiments, for example, the polyvinyl caprolactam-polyvinyl acetate-polyethylene glycol graft copolymer may be present at a concentration of at least 0.025 wt. %, at least 0.03 wt. %, at least 0.035 wt. %, at least 0.04 wt. %, at least 0.05 wt. %, at least 0.06 wt. %, at least 0.065 wt. %, at least 0.07 wt. %, at least 0.075 wt. %, at least 0.085 wt. %, at least 0.09 wt. %, at least 0.095 wt. %, at least 0.1 wt. %, at least 0.105 wt. %, or at least 0.11 wt. %. In certain embodiments, for example, the polyvinyl caprolactam-polyvinyl acetate-polyethylene glycol graft copolymer may be present at a concentration of less than 0.025 wt. %, less than 0.03 wt. %, less than 0.035 wt. %, less than 0.04 wt. %, less than 0.05 wt. %, less than 0.06 wt. %, less than 0.065 wt. %, less than 0.07 wt. %, less than 0.075 wt. %, less than 0.085 wt. %, less than 0.09 wt. %, less than 0.095 wt. %, less than 0.1 wt. %, less than 0.105 wt. %, or less than 0.11 wt. %. In certain embodiments, for example, the citric acid anhydrous may be present at a concentration in the range of 0.05-0.07 wt. %, for example in the range of 0.05-0.06 wt. %, 0.053 wt. %, 0.054 wt. %, 0.055 wt. %, 0.056 wt. %, or 0.057 wt. %. In certain embodiments, for example, the citric acid anhydrous may be present at a concentration of at least 0.03 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the citric acid anhydrous may be present at a concentration of less than 0.03 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the sodium citrate dihydrate may be present at a concentration in the range of 0.03-0.07 wt. %, for example in the range of 0.04-0.055 wt. %, 0.043 wt. %, 0.044 wt. %, 0.045 wt. %, 0.046 wt. %, 0.047 wt. %, 0.048 wt. %, 0.049 wt. %, 0.05 wt. %, 0.051 wt. %, 0.052 wt. %, 0.053 wt. % or 0.054 wt. %. In certain embodiments, for example, the sodium citrate dihydrate may be present at a concentration of at least 0.03 wt. %, at least 0.035 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the sodium citrate dihydrate may be present at a concentration of less than 0.03 wt. %, less than 0.035 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the sodium chloride may be present at a concentration in the range of 0.08-1 wt. %, for example in the range of 0.85-0.95 wt. %, 0.86 wt. %, 0.87 wt. %, 0.88 wt. %, 0.89 wt. %, 0.90 wt. %, 0.91 wt. %, 0.92 wt. %, or 0.93 wt. %. In certain embodiments, for example, the sodium chloride may be present at a concentration of at least 0.8 wt. %, at least 0.85 wt. %, at least 0.9 wt. %, or at least 0.95 wt. %. In certain embodiments, for example, the sodium chloride may be present at a concentration of less than 0.8 wt. %, less than 0.85 wt. %, less than 0.9 wt. %, or less than 0.95 wt. %. In certain embodiments, for example, the polysorbate 80 may be present at a concentration in the range of 0.05-0.07 wt. %, for example in the range of 0.05-0.065 wt. %, 0.053 wt. %, 0.054 wt. %, 0.055 wt. %, 0.056 wt. %, 0.057 wt. %, 0.058 wt. %, 0.059 wt. %, 0.06 wt. %, 0.061 wt. %, or 0.062 wt. %. In certain embodiments, for example, the polysorbate 80 may be present at a concentration of at least 0.03 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the polysorbate 80 may be present at a concentration of less than 0.03 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the propylene glycol may be present at a concentration in the range of 5-20 wt. %, for example in the range of 10-20 wt. %, 11 wt. %, 12 wt. %, 13 wt. %, 14 wt. %, 15 wt. %, 16 wt. %, 17 wt. %, or 18 wt. %. In certain embodiments, for example, the propylene glycol may be present at a concentration of at least 10 wt. %, at least 14 wt. %, at least 16 wt. %, or at least 18 wt. %. In certain embodiments, for example, the propylene glycol may be present at a concentration of less than 10 wt. %, less than 14 wt. %, less than 16 wt. %, or less than 18 wt. %. In certain further embodiments, for example, the homogeneous budesonide composition may comprise in the range of 0.005-0.05 wt. % EDTA, for example in the range of 0.005-0.02 wt. %, in the range of 0.0075-0.015 wt. % or in the range of 0.008-0.012 wt. % EDTA. In certain embodiments, for example, the homogeneous budesonide composition may comprise 0.008 wt. %, 0.009 wt. %, 0.01 wt. %, 0.011 wt. %, or 0.012 wt. % EDTA. In certain embodiments, for example, the homogeneous budesonide composition may comprise at least 0.005 wt. % EDTA, at least 0.008 wt. %, at least 0.01 wt. % or at least 0.02 wt. % EDTA. In certain embodiments, for example, the homogeneous budesonide composition may comprise less than 0.005 wt. % EDTA, less than 0.008 wt. %, less than 0.01 wt. % or less than 0.02 wt. % EDTA.

Certain embodiments may provide, for example, a homogeneous budesonide composition comprising (or consisting or consisting essentially of) 0.025 wt. % budesonide, 0.034 wt. % (or 0.035 wt. %) of a polyvinyl caprolactam-polyvinyl acetate-polyethylene glycol graft copolymer (for example SOLUPLUS), 0.055 wt. % citric acid anhydrous, 0.047 wt. % sodium citrate dihydrate, 0.0845 wt. % (or 0.085 wt. %) sodium chloride, 0.057 wt. % polysorbate 80, 15 wt. % propylene glycol, and water. In certain embodiments, for example, the pH may be in the range of 4.4-4.6 (for example 4.5).

Certain embodiments may provide, for example, a homogeneous budesonide composition comprising (or consisting or consisting essentially of) 0.025 wt. % budesonide, 0.034 wt. % (or 0.035 wt. %) of a polyvinyl caprolactam-polyvinyl acetate-polyethylene glycol graft copolymer (for example SOLUPLUS), 0.055 wt. % citric acid anhydrous, 0.047 wt. % sodium citrate dihydrate, 0.0845 wt. % (or 0.085 wt. %) sodium chloride, 0.057 wt. % polysorbate 80, 15 wt. % propylene glycol, 0.01 wt. % EDTA, and water. In certain embodiments, for example, the pH may be in the range of 4.4-4.6 (for example 4.5).

Certain embodiments may comprise, for example, an active pharmaceutical ingredient (API), a polyvinyl caprolactam-polyvinyl acetate-polyethylene glycol graft copolymer (for example SOLUPLUS), and water. In certain embodiments, for example, the API may be budesonide. In certain embodiments, for example, the API may be a poorly water soluble drug. In certain embodiments, for example, the API may be a corticosteroid (for example a poorly water-soluble corticosteroid). In certain embodiments, for example, the API may be a bronchodilator (for example a poorly water-soluble bronchodilator) such as an anticholinergic bronchodilator. In certain embodiments, for example, the API may be a beta-2 adrenergic agonist (for example a poorly water-soluble beta-2 adrenergic agonist). In certain embodiments, for example, the API may be a Biopharmaceutics Classification System (BCS) Class II drug. In certain embodiments, for example, the API may be a Biopharmaceutics Classification System (BCS) Class IV drug. In certain embodiments, for example, the API may be fexofenadine, nifedipine, griseofulvin, indomethacin, diacerein, megestrol acetate, estradiol, progesterone, medroxyprogesterone acetate, nicergoline, clonidine, etoposide, lorazepam, temazepam, digoxin, glibenclamide ketoprofen, indobufen, ibuprofen, nimesulide, diclofenac, naproxene, acemethacine, raloxifene, paroxetine, glimepiride, anagrelide, modafanil, paroxetine, cabergoline, replaginide, glipizide, benzodiazapines, clofibrate, chlorpheniramine, digoxine, diphen-hydramine, egrotamine, estradiol, fenofibrate, griseofulvin, hydrochlothizide, hydrocortisone, isosorbide, medrogeston, oxyphenbutazone, prednisolone (for example methylprednisolone acetate or methylprednisolone sodium succinate), prednisone, polythiazide, progesterone, spirono-lactone, tolbutamide, phenacetin, phenyloin, digitoxin, nilvadipine, diazepam, griseofulvin, triamcinolone (for example triamcinolone acetonide or triamcinolonehexacetonide), betamethasone (for example betamethasone acetate or betamethasone sodium phosphate), dexamethasone (for example dexamethasone sodium phosphate), fluticasone furoate, mometasone furoate, fluticasone propionate, beclomethasone dipropionate, ciclesonide, triamcinolone acetonide, flunisolide, albuterol, levalbuterol, pirbuterol, formoterol, salmeterol, terbutaline, epinephrine, ipratropium (for example ipratropium bromide), theophylline, chloramphenicol, azithromycin, carvedilol, cyclosporine, hydroxyzine, ibuprofen, ketoprofen, lorazepam, meloxicam, phenytoin, piroxicam, rofecoxib, acetaminophen, cephalexin, ciprofloxacin, doxycycline, furosemide, furosemide, linezolid, a salt (for example a pharmaceutically acceptable salt), isomer, tautomer, epimer, hydrate, solvate, crystal form, cocrystal form, amorphous form, and/or anhydrous form of any of the foregoing, or a combination of two or more of any of the foregoing.

Certain embodiments may provide, for example, a stable, homogenous, nebulizable API composition (for example a solution or nanodispersion) comprising an API (or pharmaceutically acceptable salt thereof) and a polyvinyl caprolactam-polyvinyl acetate-polyethylene glycol graft copolymer, the copolymer present at a weight ratio of less than (or no more than) 5:1 (for example less than (or no more than) 4:1 or less than (or no more than) 2:1) relative to the weight of the API in the composition, and at least 90 wt. % water. In certain embodiments, for example, the stable, homogenous, nebulizable API composition may further comprise a second drug (for example formoterol or pharmaceutically acceptable salt and/or hydrate thereof). In certain embodiments, for example, the stable, homogenous, nebulizable API composition may be a stable, homogenous, nebulizable API composition which introduces no additional side effects when inhaled compared to a nebulizable suspension of the API at the same active ingredient composition (for example introduces no additional side effects when inhaled into the stomach compared to a nebulizable suspension of the API at the same active ingredient composition).

Certain embodiments may provide, for example, a stable, benzalkonium chloride-free aqueous composition comprising a polyvinyl caprolactam-polyvinyl acetate-polyethylene glycol graft copolymer and 0.0001-1 wt. % of an API. In certain embodiments, for example, the stable, benzalkonium chloride-free aqueous composition may provide a unit dose of a therapeutic quantity of the API using a vibrating mesh nebulizer (for example a battery-powered, hand-held nebulizer). In certain embodiments, for example, the stable, benzalkonium chloride-free aqueous composition may provide a unit dose of a therapeutic quantity of the API using a Pari™ LC Jet Plus Nebulizer (with a face mask or mouthpiece) connected to a Pari™ Master compressor.

Certain embodiments may provide, for example, a stable, homogeneous API composition. In certain embodiments, for example, the composition may comprise in the range of 1-3000 mcg of an API per 2 mL of the homogenous API composition, a polyvinyl caprolactam-polyvinyl acetate-polyethylene glycol graft copolymer, present at a weight ratio of less than (or no more than) 5:1 (for example less than (or no more than) 4:1 or less than (or no more than) 2:1) relative to the weight of the API in the homogeneous API composition, and at least 90 wt. % water. In certain embodiments, for example, the homogeneous API composition may be a solution. In certain embodiments, for example, the homogeneous API composition may be a dispersion (for example a microdispersion or a nanodispersion). In certain embodiments, for example, less than 10 mg of the homogeneous API composition may be retained by an 0.2 micron filter per 1 L of the composition passed through the filter, for example less than 5 mg, less than 2 mg, less than 1 mg, or less than 0.5 mg of the homogeneous API composition may be retained by an 0.2 micron filter per 1 L of the homogeneous API composition passed through the filter. In certain embodiments, for example, less than 10 mg of the homogeneous API composition may be retained by an 0.05 micron filter per 1 L of the homogeneous API composition passed through the filter, for example less than 5 mg, less than 2 mg, less than 1 mg, or less than 0.5 mg of the homogeneous API composition may be retained by an 0.05 micron filter per 1 L of the homogeneous API composition passed through the filter. In certain embodiments, for example, at least 90% of 0.5 micron wavelength light may be transmitted through 0.1 meters of the homogeneous API composition, for example at least 95%, 98%, at least 99%, or at least 99.5% of 0.5 micron wavelength light may be transmitted through 0.1 meters of the homogeneous API composition.

In certain embodiments, for example, the composition may be nebulized (for example using a vibrating mesh nebulizer) to form droplets having an average size in the range of 0.5-10 microns (for example 1-5 microns, 2-5 microns, 3-5 microns, or 1-6 microns). In certain embodiments, for example, the composition may further comprise polysorbate 80. In certain further embodiments, for example, the polysorbate 80 may be present at a weight ratio of less than (or no more than) 5:1 (for example less than (or no more than) 4:1, such as less than (or no more than) 3:1 or less than (or no more than) 2:1) relative to the weight of the API in the composition. In certain embodiments, for example, the composition may have a combined polysorbate 80 and polyvinyl caprolactam-polyvinyl acetate-polyethylene glycol graft copolymer content present at a weight ratio of less than (or no more than) 5:1 (for example less than (or no more than) 4:1, such as less than (or no more than) 3:1 or less than (or no more than) 2:1) relative to the weight of the API in the composition. In certain embodiments, for example, the composition may have a polysorbate 80 concentration that falls within limits defined by the United States Food and Drug Administration Inactive Ingredients Database and/or Inactive Ingredient Guide (for example, falling within pharmaceutically accepted limits).

Certain embodiments may provide, for example, a stable, homogeneous API composition exclusive of preservatives (for example exclusive of preservatives such as benzalkonium chloride, polyhexamethylene biguanide, benzoic acid, and benzoates). In certain further embodiments, for example, the API may be completely dissolved in the composition. In certain embodiments, for example, the API may have a particle size of less than 100 nm (for example less than 25 nm).

Certain embodiments may provide, for example, a stable API solution comprising an API, one or more alcohols (for example less than 10 wt. % of one or more alcohols, such as less than 5 wt. % of one or more alcohols), a polyvinyl caprolactam-polyvinyl acetate-polyethylene glycol graft copolymer, and iv) less than 600 mcg polysorbate 80 (for example less than 400 mcg polysorbate 80) per mL of the solution.

Certain embodiments may provide, for example, a stable API solution consisting of the API, a polyvinyl caprolactam-polyvinyl acetate-polyethylene glycol graft copolymer, less than 600 mcg polysorbate 80 (for example in the range of 500-580 mcg polysorbate 80) per mL of the solution, and a benzalkonium chloride-free aqueous buffer solution.

Certain embodiments may provide, for example, an pharmaceutical composition (for example an aqueous pharmaceutical composition) comprising an API, a polyvinyl caprolactam-polyvinyl acetate-polyethylene glycol graft copolymer, polysorbate 80, citric acid, and sodium citrate, and less than (or no more than) 0.01 wt. % ethylenediaminetetraacetic acid. In certain further embodiments, for example, the pharmaceutical composition may be exclusive of benzalkonium chloride.

Certain embodiments may provide, for example, a stable, homogeneous API composition comprising at least 0.01 wt. % of an API, less than 1.0 wt. % polyvinyl caprolactam-polyvinyl acetate-polyethylene glycol graft copolymer, and at least 25 wt. % water. In certain embodiments, for example, the composition may be a master batch. In certain embodiments, for example, a portion or all of the master batch may be diluted to form a stable, homogeneous drug product (for example a drug product solution or a drug product nanodispersion) having a therapeutic concentration of the API that is a lower concentration than the concentration of the API present in the master batch.

In certain embodiments, one or more than one (including for instance all) of the following embodiments may comprise each of the embodiments or parts thereof. In certain embodiments, for example, any one of the foregoing compositions may be precipitate-free. In certain embodiments, for example, any one of the foregoing compositions may be solids-free. In certain embodiments, for example, any one of the foregoing compositions may be preservative-free. In certain embodiments, for example, any one of the foregoing compositions may be benzalkonium chloride-free. In certain embodiments, for example, any one of the foregoing compositions may have a pH in the range of 3-6 (for example in the range of 4-5). In certain embodiments, for example, any one of the foregoing compositions may form less than 0.008 wt. % precipitate after being stored for 3 months at a temperature of 25° C. In certain embodiments, for example, any one of the foregoing compositions may be clear. In certain embodiments, for example, any one of the foregoing compositions may be colorless. In certain embodiments, for example, any one of the foregoing compositions may be foam-free. In certain embodiments, for example, any one of the foregoing compositions may be sterile and/or pyrogen-free. In certain embodiments, for example, a homogeneous API composition may pass one or more laboratory tests for sterility conducted in accordance with U.S. Pharmacopeia <71>.

In certain embodiments, one or more than one (including for instance all) of the following embodiments may comprise each of the embodiments or parts thereof. In certain embodiments, for example, any one of the foregoing compositions may comprise an aqueous buffer solution. In certain further embodiments, for example, the buffer solution may comprise a stabilizer (for example ethylenediaminetetraacetic acid (EDTA) or a sodium salt such as sodium edetate or a magnesium salt such as magnesium chloride). In certain embodiments, for example, the buffer solution may comprise citric acid. In certain embodiments, for example, the buffer solution may comprise sodium citrate. In certain embodiments, for example, the buffer solution may comprise sodium chloride. In certain embodiments, for example, the aqueous buffer solution may be formed by combining in the range of 0.001-0.1 wt. % EDTA (for example 0.01 wt. % EDTA), relative to the total weight of the buffer solution, in the range of 0.005-0.5 wt. % citric acid anhydrous (for example 0.056 wt. % citric acid anhydrous), relative to the total weight of the buffer solution, in the range of 0.005-0.5 wt. % sodium citrate dihydrate (for example 0.048 wt. % sodium citrate dihydrate), relative to the total weight of the buffer solution, in the range of 0.05-5 wt. % sodium chloride (for example 0.8635 wt. % sodium chloride), relative to the total weight of the buffer solution, and water.

Certain embodiments may provide, for example, a homogeneous pharmaceutical composition comprising an API, a polyvinyl caprolactam-polyvinyl acetate-polyethylene glycol graft copolymer, polysorbate 80, less than 0.01 wt. % EDTA, citric acid, and sodium citrate, wherein the homogeneous, pharmaceutical composition is exclusive of benzalkonium chloride.

Certain embodiments may provide, for example, a method to prepare a precipitate-free API composition, comprising a) dispersing (for example dissolving), in a volume of a first liquid a quantity of the API particulate (for example a powder, such as an API micronized powder) followed by a quantity of polyvinyl caprolactam-polyvinyl acetate-polyethylene glycol graft copolymer, (a useful embodiment of this graft copolymer is sold under the SOLUPLUS trademark from BASF SE) to form API-containing first liquid, and b) mixing a volume of a second liquid with the API-containing first liquid to form the precipitate-free API solution. In certain embodiments, for example, the first liquid may comprise propylene glycol and/or ethanol. In certain embodiments, for example, the second liquid may comprise polysorbate 80 dissolved in a buffer solution. In certain embodiments, for example, the method may be exclusive of "homogenization." In certain embodiments, for example, the API composition may be a solution. In certain embodiments, for example, the API composition may be a nanodispersion. In certain embodiments, for example, the API particulate may be an API micronized powder having an average particle size of less than 5 microns (for example less than 1 micron). In certain embodiments, for example, the API particulate may have an average particle size of at least 25 microns (for example at least 50 microns or at least 100 microns). In certain embodiments, for example, the API particulate may have a purity of at least 98 wt. % of the API relative to the total weight of the particulate (for example at least 99 wt. %, such as at least 99.9 wt. %, at least 99.99 wt. %, or at least 99.999 wt. % of the API). In certain embodiments, for example, the API particulate may have an API purity of less than 99.9 wt. % of the API relative to the total weight of the particulate (for example less than 99 wt. %, less than 98 wt. %, less than 97 wt. %, or less than 95 wt. % of the API). In certain embodiments, for example, the API particulate may have an average particle size of less than 5 microns and a purity of at least 99 wt. % of the API relative to the total weight of the particulate. In certain embodiments, for example, the API particulate may have an average particle size of at least 25 microns and a purity of less than 98 wt. % of the API relative to the total weight of the particulate. In certain embodiments, for example, the API-containing first liquid may be clear. In certain embodiments, for example, the API-containing first liquid may be colorless. In certain embodiments, for example, the quantity of the API particulate and the quantity of polyvinyl caprolactam-polyvinyl acetate-polyethylene glycol graft copolymer may be completely dissolved in the API-containing first liquid. In certain further embodiments, for example, the API particulate and the polyvinyl caprolactam-polyvinyl acetate-polyethylene glycol graft copolymer may comprise a nanodispersion in the API-containing first liquid. In certain embodiments, for example, the API-containing first liquid may be precipitate-free. In certain embodiments, for example, the API-containing first liquid may be solids-free. In certain embodiments, for example, the ratio of the quantity of the API particulate to the volume of the first liquid may be less than 10 mg/mL (for example the ratio may be 5 mg/mL). In certain embodiments, for example, the first liquid may be an alcohol. In certain embodiments, for example, the first liquid may be propylene glycol. In certain embodiments, for example, the first liquid may be ethanol. In certain embodiments, for example, the first liquid may be a blend of propylene glycol and ethanol. In certain embodiments, for example, the API-containing first liquid may be exclusive of polyethylene glycol. In certain embodiments, for example, the ratio of the quantity of the polyvinyl caprolactam-polyvinyl acetate-polyethylene glycol graft copolymer to the volume of the first liquid may be less than 10 mg/mL (for example the ratio may be 6 mg/mL).

In certain embodiments, for example, the second liquid may be clear. In certain embodiments, for example, the second liquid may be colorless. In certain embodiments, for example, the second liquid may comprise a surfactant. The surfactant may be dissolved (for example, completely dissolved) in the second liquid. In certain embodiments, for example, the quantity of polysorbate 80 may be dissolved (for example, completely dissolved) in the second liquid. In certain embodiments, for example, the second liquid may be substantially precipitate-free (for example, precipitate-free). In certain embodiments, for example, the second liquid may be substantially solids-free (for example, solids-free). In certain embodiments, for example, the ratio of the quantity of polysorbate 80 to the volume of buffer in the second liquid may be 20 mg/mL. In certain embodiments, for example, the API composition solution may be clear. In certain embodiments, for example, the API composition may be colorless. In certain embodiments, for example, the API composition may be solids-free. In certain embodiments, for example, the API composition may be foam-free. In certain embodiments, for example, the API composition may be stable (for example: less than 5% of the API present in the API composition may decompose after at least 3 months at 25° C., no observable precipitate may be present in the API composition for at least 1 year at 25° C., the API composition may remain pharmaceutically acceptable for least 1 year at 25° C., the API composition may remain homogeneous for least 1 year at 25° C., the API composition may remain sterile for least 1 year at 25° C., and/or the API composition may remain solids-free for at least 1 year at 25° C.). In certain embodiments, for example, the API composition may be sterile. In certain embodiments, for example, the mixing may be vigorous. In certain embodiments, for example, the mixing may be low shear mixing. In certain embodiments, for example, the mixing may be high shear mixing.

In certain embodiments, for example, the polyvinyl caprolactam-polyvinyl acetate-polyethylene glycol graft copolymer may be introduced, in a solid state, to the volume of a first liquid to form the dispersion. In certain embodiments, for example, the polyvinyl caprolactam-polyvinyl acetate-polyethylene glycol graft copolymer may be introduced, in a liquid state, to the volume of a first liquid to form the dispersion. In certain embodiments, for example, the polyvinyl caprolactam-polyvinyl acetate-polyethylene glycol graft copolymer may be introduced, in a solid state, as part of a mixture to the volume of a first liquid to form the dispersion. In certain further embodiments, for example, the mixture may comprise one or more excipients. In certain embodiments, for example, the polyvinyl caprolactam-polyvinyl acetate-polyethylene glycol graft copolymer may be introduced, in a liquid state, as part of a mixture to the volume of a first liquid to form the dispersion. In certain further embodiments, for example, the mixture may comprise one or more excipients.

In certain embodiments, for example, the polysorbate 80 may be introduced, in a solid state, to the buffer to form the second liquid. In certain embodiments, for example, the polysorbate 80 may be introduced, in a liquid state, to the buffer to form the second liquid. In certain embodiments, for example, the polysorbate 80 may be introduced, in a solid state, as part of a mixture to the buffer to form the second liquid. In certain further embodiments, for example, the mixture may comprise one or more excipients. In certain embodiments, for example, the polysorbate 80 may be introduced, in a liquid state, as part of a mixture to the buffer to form the second liquid. In certain further embodiments, for example, the mixture may comprise one or more excipients.

Certain embodiments may provide, for example, a method to prepare a volume of a drug product composition (for example a dispersion, inclusive of a solution or a nanodispersion), comprising diluting a volume of the precipitate-free API composition a volume of buffer solution (for example any of the aqueous buffers disclosed herein). In certain embodiments, for example, the volume of API drug product solution may be precipitate-free and/or solids-free. In certain embodiments, for example, the volume of drug product solution may be preservative-free (for example free of benzalkonium chloride). In certain embodiments, for example, the volume of drug product solution may be complexing agent-free (for example free of ethylenediaminetetraacetic acid). In certain embodiments, for example, the method may further comprise sterile filtration of the diluted volume of the precipitate-free API composition. In certain embodiments, for example, the method may further comprise sterile filtration of the drug product solution. In certain embodiments, for example, the method may be exclusive of "homogenization." In certain embodiments, for example, the method may comprise mixing the diluted volume of the precipitate-free API composition under low shear for at least 30 minutes, for example at least 45 minutes, at least 60 minutes, at least 90 minutes, or the method may comprise the method may comprise mixing the diluted volume of the precipitate-free API composition under low shear for at least 120 minutes. In certain embodiments, for example, the method may comprise mixing the diluted volume of the precipitate-free API composition under low shear for a period of time in the range of 60-180 minutes, for example in the range of 90-150 minutes, or for a period of time of 120 minutes.

Certain embodiments may provide, for example, a method to prepare a volume of a homogeneous API composition (for example a drug product solution) that does not require forming a master batch. In certain embodiments, for example, the method may comprise directly adding quantities of the API and quantities of polyvinyl caprolactam-polyvinyl acetate-polyethylene glycol graft copolymer to aqueous buffer, followed by adding a second solution comprising the API and propylene glycol to the buffer. In certain embodiments, for example, the propylene glycol concentration may be in the range of 5-20 wt. % (for example 15 wt. %) relative to the weight of the homogeneous API composition. In certain embodiments, for example, the homogeneous API composition may comprise 0.0001-1 wt. % of the API. In certain embodiments, for example, the homogeneous API composition may comprise polyvinyl caprolactam-polyvinyl acetate-polyethylene glycol graft copolymer, present at a weight ratio of less than (or no more than) 5:1 (for example less than (or no more than) 4:1, less than (or no more than) 3:1 or less than (or no more than) 2:1) relative to the weight of the API in the composition.

In any of the foregoing methods, for example, preparation of the drug product composition may comprise adjusting the pH of the diluted volume of the precipitate-free API composition, for example by adding citric acid, sodium citrate, and/or hydrochloric acid (for example by mixing the diluted volume of the precipitate-free API composition with an aqueous solution comprising citric acid, sodium citrate, and/or hydrochloric acid). In certain embodiments, for example, the pH of the precipitate-free API composition may be adjusted to a target pH (for example a pH in the range of 2-7 (for example a pH in the range of 4-5) by adding a quantity of 10% citric acid solution or 10% sodium citrate. In certain embodiments, for example, the adjusted pH may be in the range of 2-6, for example in the range of 3-5.

Certain embodiments may provide, for example, a drug product comprising a sterile volume of any one of the foregoing compositions in a container (for example a plastic container such as a low-density polyethylene container). In certain embodiments, for example, the sterile volume of the any one of the foregoing compositions may be a single dose. In certain embodiments, for example, the container may be a single-use container. In certain embodiments, for example, the container may be sized to contain a single dose of the any one of the foregoing compositions. In certain embodiments, for example, the container may be formed by a blow-fill-seal process (for example a single use, blow-fill-seal container with a twist-off top formed by a blow-fill-seal process).

Certain embodiments may provide, for example, an aseptic process to make a drug product, comprising injecting a volume of any one of the foregoing homogeneous API compositions into a sterile blow-fill-seal container or partially formed container (for example a container in the process of being formed), and sealing the sterile blow-fill-seal container. In certain embodiments, for example, the blow-fill-seal container may be formed from molten plastic at a temperature above where micro-organisms can survive in a sterile chamber, whereby the formed blow-fill-seal container may be sterile. In certain embodiments, for example, the molten plastic may be at a temperature in the range of 170-193° C. In certain embodiments, for example, the process may be exclusive of sterilization (for example exclusive of heat sterilization) following the sealing. In certain further embodiments, for example, the blow-fill-seal container and the homogeneous API composition disposed therein may be sterile (for example due to being formed in a sterile chamber), and may remain sterile for an extended period (for example at least 24 months) even if the process may be exclusive of heat sterilization following the sealing. In certain embodiments, for example, the blow-fill-seal container may be impermeable to air. In certain further embodiments, for example, the blow-fill-seal container may be permeable to air or at least one component thereof. In certain embodiments, for example, the blow-fill-seal container may be impermeable to micro-organisms, inclusive of bacteria and viruses. In certain embodiments, for example, the process may further comprise impressing an electronic batch data code (for example cipher text) onto the sterile blow-fill-seal container. In certain embodiments, for example, the electronic batch data referenced by the electronic batch data code may be configured for distributed ledger processing (for example the electronic batch data or ciphertext thereof may be included in a blockchain or other distributed ledger technology). In certain embodiments, for example, a blow-fill-seal method may comprise impressing an electronic batch data code (for example ciphertext) onto a blow-fill-seal container. In certain embodiments, for example, the electronic batch data referenced by the electronic batch data code may be configured for distributed ledger processing (for example the electronic batch data or a ciphertext thereof may be included in a blockchain or a distributed ledger technology).

In certain further embodiments, for example, the process may further comprise sterile filtration of the any one of the homogeneous API compositions disclosed herein prior to introduction to the blow-fill-seal container. In certain embodiments, for example, the sterile filtration may comprise microfiltration using one or more filters (for example the one or more filters may comprise a membrane filter). In certain embodiments, for example, the one or more filters may have a pore size of less than 1 micron, for example less than 0.5 microns, less than 0.2 microns, less than 0.1 micron, or the one or more filters may have a pore size of less than 0.05 microns. In certain embodiment, for example, the one or more filters may have a pore size in the range of 0.05-1 microns, for example in the range of 0.1-0.5 microns, in the range of 0.15-0.3 microns, or the one or more filters may have a pore size in the range of 0.19-0.25 microns. In certain embodiments, for example, any of the foregoing one or more filters may be a pre-filter. In certain embodiments, for example, the one or more filters may have a pore size of less than 100 nm, for example less than 75 nm, less than 50 nm, less than 30 nm, or the one or more filters may have a pore size of less than 20 nm. In certain embodiment, for example, the one or more filters may have a pore size in the range of 1-100 nm, for example in the range of 10-75 nm, in the range of 20-50 nm, or the one or more filters may have a pore size in the range of 30-50 nm. In certain embodiments, for example, the one or more filters may comprise mixed cellulose ester. In certain embodiments, for example, the one or more filters may be a polyvinylidene fluoride (PVDF) filter (for example an 0.2 micron PVDF filter). In certain embodiments, for example, the one or more filters may comprise polyethersulfone (PES). In certain embodiments, for example, the one or more filters may comprise a pre-sterilized disposable unit. In certain further embodiments, for example, the pre-sterilized disposable unit may be provided in a sealed package. In certain embodiments, for example, the one or more filters may be sterilized (for example by autoclaving at a temperature that does not damage the filter). In certain embodiments, for example, the one or more filters may be tested for integrity and/or sterility prior to use. In certain embodiments, for example, the one or more filters may be tested for integrity and/or sterility after use. In certain embodiments, for example, the sterile filtration may be performed in a clean room. In certain further embodiments, for example, the clean room may have no more than 1,000,000 particles, per cubic meter, having a size larger than 0.5 microns, for example no more than 100,000 particles per cubic meter, for example no more than 10,000 particles per cubic meter, for example no more than 5,000 particles per cubic meter, no more than 2,500 particles per cubic meter, no more than 2,000 particles per cubic meter, no more than 1,000 particles per cubic meter, no more than 100 particles per cubic meter, no more than 50 particles per cubic meter, no more than 12 particles per cubic meter, or the clean room may have fewer than 1000 particles, per cubic meter, having a size larger than 0.5 microns. In certain embodiments, for example, the clean room may be an ISO class 5 clean room. In certain embodiments, for example, the clean room may be an ISO class 4 clean room. In certain embodiments, for example, the clean room may be an ISO class 3 clean room. In certain embodiments, for example, the clean room may be an ISO class 2 clean room. In certain embodiments, for example, the clean room may be an ISO class 1 clean room. In certain embodiments, for example, air entering the clean room may be passed through a high-efficiency particulate air (HEPA) filter prior to entering the clean room. In certain embodiments, for example, air entering the clean room may be passed through a high-efficiency particulate air (HEPA) filter prior to entering the clean room. In certain embodiments, for example, air entering the clean room may be passed through an ultra-low particulate air (ULPA) filter.

In certain embodiments, for example, the sterile filtration of the homogeneous API solution may remove at least 95 wt. % of microorganisms or other pathogens present in the homogeneous API solution prior to the sterile filtration, for example at least 99 wt. %, 99.9 wt. %, 99.99 wt. %, 99.999 wt. %, 99.9999 wt. %, 99.99999 wt. %, 99.999999 wt. %, 99.9999999 wt. %, or the sterile filtration of the homogeneous API solution may remove at least 99.99999999 wt. % of microorganisms or other pathogens present in the homogeneous API solution prior to the sterile filtration Certain embodiments may provide, for example, a method of treating, preventing, or ameliorating one or more symptoms of a bronchoconstriction-related disease or disorder, comprising nebulizing, by a nebulizer, a unit dose of any one of the homogeneous API compositions disclosed herein. In certain embodiments, for example, the unit dose may be nebulized by a vibrating mesh nebulizer. In certain embodiments, for example, the nebulizer may be a hand-held, battery powered nebulizer. In certain embodiments, for example, the method may further comprise providing the unit dose to the nebulizer from a single use, blow-fill-seal container.

Certain embodiments may provide, for example, a stable, homogeneous API composition comprising: i) at least 0.0001 wt. % of the API; ii) less than 1.0 wt. % polyvinyl caprolactam-polyvinyl acetate-polyethylene glycol graft copolymer, present at a weight ratio of less than (or no more than) 4:1 (for example less than (or no more than) 3:1 or less than (or no more than) 2:1) relative to the weight of the API in the composition; and iii) at least 25 wt. % water.

Certain embodiments may provide, for example, a stable, homogeneous API composition comprising: i) an API; ii) a polyvinyl caprolactam-polyvinyl acetate-polyethylene glycol graft copolymer, present at a weight ratio of less than (or no more than) 4:1 (for example less than (or no more than) 3:1 or less than (or no more than) 2:1) relative to the weight of the API in the composition; and iii) at least 90 wt. % water.

Certain embodiments may provide, for example, a stable, homogeneous API composition comprising: i) 0.0001-1 wt. % of an API, the API being completely dissolved or having a particle size of less than 10 nm; and ii) at least 90 wt. % water, wherein the stable, homogeneous API composition may be exclusive of benzalkonium chloride.

Certain embodiments may provide, for example, a stable API solution comprising: i) an API; ii) one or more alcohols; iii) a polyvinyl caprolactam-polyvinyl acetate-polyethylene glycol graft copolymer; and iv) less than 400 mcg polysorbate 80 per mL of the solution.

Certain embodiments may provide, for example, a stable API solution consisting of: i) an API; ii) a polyvinyl caprolactam-polyvinyl acetate-polyethylene glycol graft copolymer; iii) less than 600 mcg polysorbate 80 per mL of the solution; and iv) a benzalkonium chloride-free aqueous buffer solution. In certain embodiments, for example, the stable API solution may comprise less than 375 mcg polyvinyl caprolactam-polyvinyl acetate-polyethylene glycol graft copolymer per mL of the solution.

Certain embodiments may provide, for example, a stable API solution consisting of: i) an API; ii) a polyvinyl caprolactam-polyvinyl acetate-polyethylene glycol graft copolymer; iii) less than 600 mcg polysorbate 80 per mL of the solution; and iv) a benzalkonium chloride-free aqueous buffer solution. In certain embodiments, for example, the stable API solution may comprise less than 750 mcg polyvinyl caprolactam-polyvinyl acetate-polyethylene glycol graft copolymer per mL of the solution.

Certain embodiments may provide, for example, a stable API solution consisting of: i) an API; ii) a polyvinyl caprolactam-polyvinyl acetate-polyethylene glycol graft copolymer; iii) less than 1000 mcg polysorbate 80 per mL of the solution; and iv) a benzalkonium chloride-free aqueous buffer solution. In certain embodiments, for example, the stable API solution may comprise less than 1500 mcg polyvinyl caprolactam-polyvinyl acetate-polyethylene glycol graft copolymer per mL of the solution.

Certain embodiments may provide, for example, a method to prepare a precipitate-free API solution, comprising: i) dissolving, in a volume of a first liquid, a) a quantity of the API particulate (for example a powder such as an API micronized powder); followed by b) a quantity of polyvinyl caprolactam-polyvinyl acetate-polyethylene glycol graft copolymer, to form API-containing first liquid; and ii) mixing a volume of a second liquid with the API-containing first liquid to form the API solution, wherein the first liquid comprises: propylene glycol and/or ethanol; and the second liquid comprises: polysorbate 80 dissolved in a buffer solution.

Certain embodiments may provide, for example, a stable, homogeneous (substantially uniformly or uniformly dispersed) API dispersion comprising in the range of 0.0001-1 wt. % (for example 0.0125-0.05 wt. %) of an API, and at least 90 wt. % water, the stable, homogeneous API dispersion exclusive of a preservative (for example benzalkonium chloride). In certain further embodiments, for example, the API may be completely dissolved in the dispersion. In certain embodiments, for example, the API may have a particle size of less than 100 nm (for example less than 25 nm).

Certain embodiments may provide, for example, a stable homogeneous (substantially uniformly or uniformly dispersed) API dispersion comprising an API, one or more alcohols (for example less than 5 wt. % of one or more alcohols), a polyvinyl caprolactam-polyvinyl acetate-polyethylene glycol graft copolymer, and iv) less than 400 mcg polysorbate 80 per mL of the dispersion. In certain further embodiments, for example, the API may be completely dissolved in the dispersion. In certain embodiments, for example, the API may have a particle size of less than 100 nm (for example less than 25 nm).

Certain embodiments may provide, for example, a stable homogeneous (substantially uniformly or uniformly dispersed) API dispersion consisting of the API, a polyvinyl caprolactam-polyvinyl acetate-polyethylene glycol graft copolymer, less than 580 mcg polysorbate 80 per mL of the dispersion, and a benzalkonium chloride-free aqueous buffer solution. In certain further embodiments, for example, the API may be completely dissolved in the dispersion. In certain embodiments, for example, the API may have a particle size of less than 100 nm (for example less than 25 nm).

Certain embodiments may provide, for example, a stable homogeneous (substantially uniformly or uniformly dispersed) API dispersion comprising an API, in the range of 60-250 mcg polyvinyl caprolactam-polyvinyl acetate-polyethylene glycol graft copolymer per mL of the dispersion, in the range of 50-350 mcg polysorbate 80 per mL of the dispersion, and a benzalkonium chloride-free aqueous buffer solution. In certain further embodiments, for example, the dispersion may comprise in the range of 500-15,000 mcg of one or more alcohols per mL of the dispersion. In certain further embodiments, for example, the one or more alcohols may comprise propylene glycol. In certain embodiments, for example, the API may be completely dissolved in the dispersion. In certain embodiments, for example, the API may have a particle size of less than 100 nm (for example less than 25 nm) in the dispersion.

Certain embodiments may provide, for example, a stable, homogeneous API composition comprising: 0.0001-1 wt. % (for example 0.0125-0.05 wt. %) of an API, a polyvinyl caprolactam-polyvinyl acetate-polyethylene glycol graft copolymer present at a weight ratio of less than (or no more than) 5:1 (for example less than (or no more than) 4:1, less than (or no more than) 3:1, or less than (or no more than) 2:1), relative to the weight of the API in the composition, and at least 90 wt. % water. In certain embodiments, for example, the composition may further comprise polysorbate 80 present at a weight ratio of less than (or no more than) 2:1, relative to the API concentration. In certain embodiments, for example, the composition may be benzalkonium chloride-free. In certain embodiments, for example, the composition may be stable (for example retain greater than 80%, 85%, or 95% of original API content) following storage in a polyethylene container for 24 months at a temperature of 25° C. and 40% relative humidity. In certain embodiments, for example, the composition may be a solution. In certain embodiments, for example, the composition may be a nanodispersion. In certain embodiments, for example, the composition may form droplets having an average size in the range of 1-6 microns when passed through a Pari™ LC Jet Plus Nebulizer connected to a Pari™ Master compressor. Certain embodiments may provide, for example, a drug product comprising a sterile volume of one of the composition in a single dose, blow-fill-seal container. Certain embodiments may provide, for example, an aseptic process to form a drug product composition, comprising: injecting a volume of the composition into a sterile blow-fill-seal container, and sealing the sterile blow-fill-seal container. In certain embodiments, for example, the process may further comprise sterilizing the volume of the composition prior to the injecting. In certain embodiments, for example, the aseptic process may be exclusive of sterilization following the sealing. Certain embodiments may provide, for example, a method of treating, preventing, or ameliorating one or more symptoms of a bronchoconstriction-related disease or disorder, comprising: nebulizing, by a nebulizer, a unit dose of the composition.

Certain embodiments may provide, for example, a homogeneous, pharmaceutical composition comprising: at least 0.0001 wt. % of an API, less than 0.05 wt. % polyvinyl caprolactam-polyvinyl acetate-polyethylene glycol graft copolymer, less than 1 wt. % polysorbate 80, less than 0.01 wt. % ethylenediaminetetraacetic acid, citric acid, sodium citrate, and sodium chloride, the pharmaceutical composition exclusive of preservatives.

Certain embodiments may provide, for example, a method to prepare a precipitate-free composition, comprising: dispersing, in a volume of a first liquid, a quantity of API particulate (for example a powder such as a API micronized powder) followed by a quantity of polyvinyl caprolactam-polyvinyl acetate-polyethylene glycol graft copolymer to form a API-containing first liquid, and mixing at least a portion of the API-containing first liquid with a volume of a second liquid to form the precipitate-free composition.

Certain embodiments may provide, for example, a method to prepare a precipitate-free composition, comprising: forming a API-containing first liquid, comprising: dispersing a quantity of API particulate (for example a powder such as a API micronized powder) in a volume of first liquid, forming a second liquid, comprising: dissolving a quantity of polyvinyl caprolactam-polyvinyl acetate-polyethylene glycol graft copolymer in a volume of water, and mixing at least a portion of the API-containing first liquid with a volume of the second liquid for at least 30 minutes to form the precipitate-free composition, the precipitate-free composition comprising at least 90 wt. % water, wherein the method may be exclusive of high shear mixing. In certain embodiments, for example, the ratio of the quantity of polyvinyl caprolactam-polyvinyl acetate-polyethylene glycol graft copolymer to the quantity of API particulate may be less than (or no more than) 5:1 (for example less than (or no more than) 4:1, such as less than (or no more than) 3:1 or less than (or no more than) 2:1). In certain embodiments, for example, the composition may be a solution. In certain embodiments, for example, the composition may be a nanodispersion. In certain embodiments, for example, the first liquid may comprise propylene glycol and/or ethanol. In certain embodiments, for example, the second liquid may comprise polysorbate 80.

Certain embodiments may provide, for example, a homogeneous API inhalation solution or nanodispersion consisting of: 0.035 wt. % a polyvinyl caprolactam-polyvinyl acetate-polyethylene glycol graft copolymer (for example SOLUPLUS), 0.056 wt. % citric acid anhydrous, 0.048 wt. % sodium citrate dihydrate, 0.8635 wt. % sodium chloride, 0.0001-1 wt. % of an API, 0.058 wt. % polysorbate 80, 0-5 wt. % propylene glycol, and 0-5 wt. % ethanol.

Certain embodiments may provide, for example, a homogeneous API composition that retains at least 85% active ingredient after 24 months at 25° C. and 40% relative humidity, the composition comprising: 0.0001-1 wt. % (for example 0.0125-0.05 wt. %) of an API and a polyvinyl caprolactam-polyvinyl acetate-polyethylene glycol graft copolymer (for example SOLUPLUS), present at a weight ratio no more than 4:1, relative to the weight of the API in the composition, mixed exclusively by low shear mixing with at least 90 wt. % water.

Certain embodiments may provide, for example, a homogeneous API composition that retains at least 85% active ingredient after 24 months at 25° C. and 40% relative humidity, the composition comprising: 0.0001-1 wt. % (for example 0.0125-0.05 wt. %) of an API and a polyvinyl caprolactam-polyvinyl acetate-polyethylene glycol graft copolymer (for example SOLUPLUS), present at a weight ratio of no more than 4:1, relative to the weight of the API in the composition, and at least 90 wt. % water, the composition prepared without high shear mixing.

Certain embodiments may provide, for example, a homogeneous API composition that retains at least 85% active ingredient after 24 months at 25° C. and 40% relative humidity, the composition comprising: 0.0001-1 wt. % (for example 0.0125-0.05 wt. %) of an API and a polyvinyl caprolactam-polyvinyl acetate-polyethylene glycol graft copolymer (for example SOLUPLUS), present at a weight ratio of no more than 4:1, relative to the weight of the API in the composition, and at least 90 wt. % water. In certain embodiments, for example, the composition may be exclusive of cellulose-derived compounds. In certain embodiments, for example, the composition may be exclusive of cyclodextrines.

Certain embodiments may provide, for example, a homogeneous API composition that retains at least 85% active ingredient after 24 months at 25° C. and 40% relative humidity, the composition comprising: 0.0001-1 wt. % (for example 0.0125-0.05 wt. %) of an API and a polyvinyl caprolactam-polyvinyl acetate-polyethylene glycol graft copolymer (for example SOLUPLUS), present at a weight ratio of no more than 4:1, relative to the weight of the API in the composition, and at least 90 wt. % water, the composition exclusive of benzalkonium chloride, EDTA, cellulose derivatives, and cyclodextrines, the composition formed exclusive of high shear mixing.

Certain embodiments may provide, for example, a homogeneous API composition comprising (or consisting or consisting essentially of) in the range of 0.01-0.05 wt. % of an API, 0.01-0.1 wt. % of a polyvinyl caprolactam-polyvinyl acetate-polyethylene glycol graft copolymer (for example SOLUPLUS), 0.01-0.1 wt. % citric acid anhydrous, 0.01-0.1 wt. % sodium citrate dihydrate, 0.8-1 wt. % sodium chloride, 0.01-0.1 wt. % polysorbate 80, and 5-20 wt. % propylene glycol. In certain embodiments, for example, the API may be present at a concentration in the range of 0.0125-0.025 wt. %, 0.015 wt. %, or 0.02 wt. %. In certain embodiments, for example, the API may be present at a concentration of at least 0.01 wt. %, at least 0.02 wt. %, or at least 0.03 wt. %. In certain embodiments, for example, the API may be present at a concentration of less than 0.01 wt. %, less than 0.02 wt. %, or less than 0.03 wt. %. In certain embodiments, for example, the polyvinyl caprolactam-polyvinyl acetate-polyethylene glycol graft copolymer may be present at a concentration in the range of 0.02-0.045 wt. %, for example in the range of 0.03-0.04 wt. %, 0.033 wt. %, 0.034 wt. %, 0.035 wt. %, 0.036 wt. %, or 0.037 wt. %. In certain embodiments, for example, the polyvinyl caprolactam-polyvinyl acetate-polyethylene glycol graft copolymer may be present at a concentration in the range of 0.05-0.075 wt. %, for example in the range of 0.06-0.07 wt. %, 0.065 wt. %, 0.066 wt. %, 0.067 wt. %, 0.068 wt. %, or 0.069 wt. %. In certain embodiments, for example, the polyvinyl caprolactam-polyvinyl acetate-polyethylene glycol graft copolymer may be present at a concentration in the range of 0.09-0.11 wt. %, for example in the range of 0.095-0.105 wt. %, 0.098 wt. %, 0.099 wt. %, 0.1 wt. %, 0.101 wt. %, or 0.102 wt. %. In certain embodiments, for example, the polyvinyl caprolactam-polyvinyl acetate-polyethylene glycol graft copolymer may be present at a concentration of at least 0.025 wt. %, at least 0.03 wt. %, at least 0.035 wt. %, at least 0.04 wt. %, at least 0.05 wt. %, at least 0.06 wt. %, at least 0.065 wt. %, at least 0.07 wt. %, at least 0.075 wt. %, at least 0.085 wt. %, at least 0.09 wt. %, at least 0.095 wt. %, at least 0.1 wt. %, at least 0.105 wt. %, or at least 0.11 wt. %. In certain embodiments, for example, the polyvinyl caprolactam-polyvinyl acetate-polyethylene glycol graft copolymer may be present at a concentration of less than 0.025 wt. %, less than 0.03 wt. %, less than 0.035 wt. %, less than 0.04 wt. %, less than 0.05 wt. %, less than 0.06 wt. %, less than 0.065 wt. %, less than 0.07 wt. %, less than 0.075 wt. %, less than 0.085 wt. %, less than 0.09 wt. %, less than 0.095 wt. %, less than 0.1 wt. %, less than 0.105 wt. %, or less than 0.11 wt. %. In certain embodiments, for example, the citric acid anhydrous may be present at a concentration in the range of 0.05-0.07 wt. %, for example in the range of 0.05-0.06 wt. %, 0.053 wt. %, 0.054 wt. %, 0.055 wt. %, 0.056 wt. %, or 0.057 wt. %. In certain embodiments, for example, the citric acid anhydrous may be present at a concentration of at least 0.03 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the citric acid anhydrous may be present at a concentration of less than 0.03 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the sodium citrate dihydrate may be present at a concentration in the range of 0.03-0.07 wt. %, for example in the range of 0.04-0.055 wt. %, 0.043 wt. %, 0.044 wt. %, 0.045 wt. %, 0.046 wt. %, 0.047 wt. %, 0.048 wt. %, 0.049 wt. %, 0.05 wt. %, 0.051 wt. %, 0.052 wt. %, 0.053 wt. % or 0.054 wt. %. In certain embodiments, for example, the sodium citrate dihydrate may be present at a concentration of at least 0.03 wt. %, at least 0.035 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the sodium citrate dihydrate may be present at a concentration of less than 0.03 wt. %, less than 0.035 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the sodium chloride may be present at a concentration in the range of 0.08-1 wt. %, for example in the range of 0.85-0.95 wt. %, 0.86 wt. %, 0.87 wt. %, 0.88 wt. %, 0.89 wt. %, 0.90 wt. %, 0.91 wt. %, 0.92 wt. %, or 0.93 wt. %. In certain embodiments, for example, the sodium chloride may be present at a concentration of at least 0.8 wt. %, at least 0.85 wt. %, at least 0.9 wt. %, or at least 0.95 wt. %. In certain embodiments, for example, the sodium chloride may be present at a concentration of less than 0.8 wt. %, less than 0.85 wt. %, less than 0.9 wt. %, or less than 0.95 wt. %. In certain embodiments, for example, the polysorbate 80 may be present at a concentration in the range of 0.05-0.07 wt. %, for example in the range of 0.05-0.065 wt. %, 0.053 wt. %, 0.054 wt. %, 0.055 wt. %, 0.056 wt. %, 0.057 wt. %, 0.058 wt. %, 0.059 wt. %, 0.06 wt. %, 0.061 wt. %, or 0.062 wt. %. In certain embodiments, for example, the polysorbate 80 may be present at a concentration of at least 0.03 wt. %, at least 0.04 wt. %, at least 0.045 wt. %, at least 0.05 wt. %, at least 0.055 wt. %, at least 0.06 wt. %, at least 0.065 wt. %, at least 0.07 wt. %, or at least 0.075 wt. %. In certain embodiments, for example, the polysorbate 80 may be present at a concentration of less than 0.03 wt. %, less than 0.04 wt. %, less than 0.045 wt. %, less than 0.05 wt. %, less than 0.055 wt. %, less than 0.06 wt. %, less than 0.065 wt. %, less than 0.07 wt. %, or less than 0.075 wt. %. In certain embodiments, for example, the propylene glycol may be present at a concentration in the range of 5-20 wt. %, for example in the range of 10-20 wt. %, 11 wt. %, 12 wt. %, 13 wt. %, 14 wt. %, 15 wt. %, 16 wt. %, 17 wt. %, or 18 wt. %. In certain embodiments, for example, the propylene glycol may be present at a concentration of at least 10 wt. %, at least 14 wt. %, at least 16 wt. %, or at least 18 wt. %. In certain embodiments, for example, the propylene glycol may be present at a concentration of less than 10 wt. %, less than 14 wt. %, less than 16 wt. %, or less than 18 wt. %. In certain further embodiments, for example, the homogeneous API composition may comprise in the range of 0.005-0.05 wt. % EDTA, for example in the range of 0.005-0.02 wt. %, in the range of 0.0075-0.015 wt. % or in the range of 0.008-0.012 wt. % EDTA. In certain embodiments, for example, the homogeneous API composition may comprise 0.008 wt. %, 0.009 wt. %, 0.01 wt. %, 0.011 wt. %, or 0.012 wt. % EDTA. In certain embodiments, for example, the homogeneous API composition may comprise at least 0.005 wt. % EDTA, at least 0.008 wt. %, at least 0.01 wt. % or at least 0.02 wt. % EDTA. In certain embodiments, for example, the homogeneous API composition may comprise less than 0.005 wt. % EDTA, less than 0.008 wt. %, less than 0.01 wt. % or less than 0.02 wt. % EDTA.

Certain embodiments may provide, for example, an aqueous homogeneous pharmaceutical composition comprising: i) at least 0.01 wt. % (for example in the range of 0.01-1 wt. %, in the range of 0.0125-0.05 wt. %, in the range of 0.025-0.1 wt. %, in the range of 0.1-0.5 wt. %, or in the range of 0.5-1 wt. %) of an active pharmaceutical compound, combination of compounds or composition; ii) no more than 0.1 wt. %, (for example in the range of 0.0125-0.1 wt. %, in the range of 0.025-0.075 wt. %, or in the range of 0.05-0.1 wt. %) of a polyvinyl caprolactam-polyvinyl acetate-polyethylene glycol graft copolymer; and iii) optionally none or no more than 0.01 wt. % EDTA, wherein the pharmaceutical composition is exclusive of preservatives.

Certain embodiments may provide, for example, an aqueous homogeneous pharmaceutical composition comprising: i) at least 0.01 wt. % (for example in the range of 0.01-1 wt. %, in the range of 0.0125-0.05 wt. %, in the range of 0.025-0.1 wt. %, in the range of 0.1-0.5 wt. %, or in the range of 0.5-1 wt. %) of an active pharmaceutical compound, combination of compounds or composition; ii) no more than 0.1 wt. %, (for example in the range of 0.0125-0.1 wt. %, in the range of 0.025-0.075 wt. %, or in the range of 0.05-0.1 wt. %) of a polyvinyl caprolactam-polyvinyl acetate-polyethylene glycol graft copolymer; iii) less than 0.1 wt. % polysorbate 80 (for example in the range of 0.025-0.075 wt. %, in the range of 0.01-0.06 wt. %, or in the range of 0.04-0.09 wt. %); iv) optionally none or no more than 0.01 wt. % EDTA; v) citric acid; vi) sodium citrate; and vii) sodium chloride, wherein the pharmaceutical composition is exclusive of preservatives.

DETAILED DESCRIPTION OF THE INVENTION

Certain embodiments may provide, for example, a homogenous budesonide composition. In certain embodiments, for example, the homogeneous budesonide composition may be a drug product. In certain embodiments, for example, the drug product may be a sterile nebulizable pharmaceutical solution or nanodispersion for inhalation via nebulization. In certain embodiments, for example, the drug product may be a sterile ophthalmic solution or nanodispersion. In certain embodiments, for example, the drug product may be a sterile nasal spray. In certain embodiments, for example, the drug product may be a sterile topical solution or nanodispersion. In certain embodiments, for example, the drug product may be a sterile solution or nanodispersion suitable for intravenous injection or injection into tissue. In certain embodiments, for example, the homogenous budesonide composition may be a solution or nanodispersion that may be dried (for example spray dried or freeze dried) to form a sterile powdered drug product (for example a powdered drug product suitable for delivery by nasal or pulmonary inhalation).

Certain embodiments may provide, for example, a homogeneous (substantially uniformly or uniformly dispersed) budesonide composition comprising budesonide. In certain embodiments, for example, the homogeneous budesonide composition may be a solution (for example an aqueous solution). In certain embodiments, for example, the homogeneous budesonide composition may be a nanodispersion. In certain embodiments, for example, the total budesonide content of the composition may be a unit dose of budesonide in the range of 0.0625 mg to no more than 10 mg, for example the total budesonide content of the composition may be a unit dose of budesonide in the range of 0.125 mg to no more than 5 mg, in the range of 0.175 mg to no more than 5 mg, in the range of 0.25 mg to no more than 2.5 mg, or the total budesonide content of the composition may be a unit dose of budesonide in the range of 0.25 mg to no more than 1 mg. In certain embodiments, for example, the total budesonide content of the composition may be a unit dose of budesonide in the range of 0.1 mg to no more than 0.4 mg, for example the total budesonide content of the composition may be a unit dose of budesonide in the range of 0.15 mg to no more than 0.35 mg, in the range of 0.2 mg to no more than 0.3 mg, or the total budesonide content of the composition may be a unit dose of budesonide in the range of 0.24 mg to no more than 0.3 mg. In certain embodiments, for example, the total budesonide content of the composition may be a unit dose of budesonide of 0.25 mg. In certain embodiments, for example, the total budesonide content of the composition may be a unit dose of budesonide of 0.5 mg. In certain embodiments, for example, the total budesonide content of the composition may be a unit dose of budesonide of 1 mg. In certain embodiments, for example, the total budesonide content of the composition may be a unit dose of budesonide in the range of 0.35 mg to no more than 0.65 mg, for example the total budesonide content of the composition may be a unit dose of budesonide in the range of 0.4 mg to no more than 0.6 mg, in the range of 0.45 mg to no more than 0.55 mg, or the total budesonide content of the composition may be a unit dose of budesonide in the range of 0.48 mg to no more than 0.52 mg. In certain embodiments, for example, the total budesonide content of the composition may be a unit dose of budesonide in the range of 0.85 mg to no more than 1.15 mg, for example the total budesonide content of the composition may be a unit dose of budesonide in the range of 0.9 mg to no more than 1.1 mg, in the range of 0.95 mg to no more than 1.05 mg, or the total budesonide content of the composition may be a unit dose of budesonide in the range of 0.98 mg to no more than 1.02 mg. In certain embodiments, for example, the total budesonide content of the composition may be a unit dose of budesonide in the range of 0.025 mg to no more than 10 mg, for example the total budesonide content of the composition may be a unit dose of budesonide in the range of 0.025 mg to no more than 0.125 mg, in the range of 0.125 mg to no more than 0.225 mg, in the range of 0.225 mg to no more than 0.325 mg, in the range of 0.325 mg to no more than 0.425 mg, in the range of 0.425 mg to no more than 0.525 mg, in the range of 0.525 mg to no more than 0.625 mg, in the range of 0.625 mg to no more than 0.725 mg, in the range of 0.725 mg to no more than 0.825 mg, in the range of 0.825 mg to no more than 0.925 mg, in the range of 0.925 mg to no more than 1.025 mg, in the range of 1.025 mg to no more than 1.2 mg, in the range of 1.2 mg to no more than 2 mg, in the range of 2 mg to no more than 4 mg, in the range of 4 mg to no more than 6 mg, in the range of 6 mg to no more than 8 mg, or the total budesonide content of the composition may be a unit dose of budesonide in the range of 8 mg to no more than 10 mg. In certain embodiments, for example, the total budesonide content of the composition may be an 0.125 mg unit dose of budesonide. In certain embodiments, for example, the total budesonide content of the composition may be an 0.25 mg unit dose of budesonide. In certain embodiments, for example, the total budesonide content of the composition may be an 0.5 mg unit dose of budesonide. In certain embodiments, for example, the total budesonide content of the composition may be a 1.0 mg unit dose of budesonide. In certain embodiments, for example, the homogeneous budesonide composition may be a nanodispersion. In certain embodiments, for example, the budesonide may be present in the composition at a concentration in the range of 0.0125-5 mg/mL, for example the budesonide may be present in the composition at a concentration in the range of 0.0625-2.5 mg/mL, in the range of 0.0875-2.5 mg/mL, in the range of 0.125-1.25 mg/mL, or the budesonide may be present in the composition at a concentration in the range of 0.125-0.5 mg/mL. In certain embodiments, for example, the budesonide may be present in the composition at a concentration in the range of 0.05-0.2 mg/mL, for example the budesonide may be present in the composition at a concentration in the range of 0.075-0.175 mg/mL, in the range of 0.1-0.15 mg/mL, or the budesonide may be present in the composition at a concentration in the range of 0.12-0.3 mg/mL. In certain embodiments, for example, the budesonide may be present in the composition at a concentration of 0.125 mg/m L. In certain embodiments, for example, the budesonide may be present in the composition at a concentration of 0.25 mg/mL. In certain embodiments, for example, the budesonide may be present in the composition at a concentration of 0.5 mg/mL. In certain embodiments, for example, the budesonide may be present in the composition at a concentration in the range of 0.175-0.325 mg/mL, for example the budesonide may be present in the composition at a concentration in the range of 0.2-0.3 mg/mL, in the range of 0.225-0.275 mg/mL, or the budesonide may be present in the composition at a concentration in the range of 0.24-0.26 mg/mL. In certain embodiments, for example, the budesonide may be present in the composition at a concentration in the range of 0.425-0.575 mg/mL, for example the budesonide may be present in the composition at a concentration in the range of 0.45-0.55 mg/mL, in the range of 0.475-0.525 mg/mL, or the budesonide may be present in the composition at a concentration in the range of 0.49-0.51 mg/mL. In certain embodiments, for example, the budesonide may be present in the composition at a concentration in the range of 0.0125-5 mg/mL, for example the budesonide may be present in the composition at a concentration in the range of 0.0125-0.0625 mg/mL, in the range of 0.0625-0.1125 mg/mL, in the range of 0.1125-0.1625 mg/mL, in the range of 0.1625-0.2125 mg/mL, in the range of 0.2125-0.2625 mg/mL, in the range of 0.2625-0.3125 mg/mL, in the range of 0.3125-0.3625 mg/mL, in the range of 0.3625-0.4125 mg/mL, in the range of 0.4125-0.4625 mg/mL, in the range of 0.4625-0.5125 mg/mL, in the range of 0.5125-0.6 mg/mL, in the range of 0.6-1 mg/mL, in the range of 1-2 mg/mL, in the range of 2-3 mg/mL, in the range of 3-4 mg/mL, or the budesonide may be present in the composition at a concentration in the range of 4-5 mg/mL. In certain embodiments, for example, the budesonide may be present in the composition at a concentration in the range of 0.0625-10 mg/2 mL, for example the budesonide may be present in the composition at a concentration in the range of 0.125-5 mg/2 mL, in the range of 0.175-5 mg/2 mL, in the range of 0.25-2.5 mg/2 mL, or the budesonide may be present in the composition at a concentration in the range of 0.25-1 mg/2 mL. In certain embodiments, for example, the budesonide may be present in the composition at a concentration in the range of 0.1-0.4 mg/2 mL, for example the budesonide may be present in the composition at a concentration in the range of 0.15-0.35 mg/2 mL, in the range of 0.2-0.3 mg/2 mL, or the budesonide may be present in the composition at a concentration in the range of 0.24-0.3 mg/2 mL. In certain embodiments, for example, the budesonide may be present in the composition at a concentration of 0.25 mg/2 mL. In certain embodiments, for example, the budesonide may be present in the composition at a concentration of 0.5 mg/2 mL. In certain embodiments, for example, the budesonide may be present in the composition at a concentration of 1 mg/2 mL. In certain embodiments, for example, the budesonide may be present in the composition at a concentration in the range of 0.35-0.65 mg/2 mL, for example the budesonide may be present in the composition at a concentration in the range of 0.4-0.6 mg/2 mL, in the range of 0.45-0.55 mg/2 mL, or the budesonide may be present in the composition at a concentration in the range of 0.48-0.52 mg/2 mL. In certain embodiments, for example, the budesonide may be present in the composition at a concentration in the range of 0.85-1.15 mg/2 mL, for example the budesonide may be present in the composition at a concentration in the range of 0.9-1.1 mg/2 mL, in the range of 0.95-1.05 mg/2 mL, or the budesonide may be present in the composition at a concentration in the range of 0.98-1.02 mg/2 mL. In certain embodiments, for example, the budesonide may be present in the composition at a concentration in the range of 0.025-10 mg/2 mL, for example the budesonide may be present in the composition at a concentration in the range of 0.025-0.125 mg/2 mL, in the range of 0.125-0.225 mg/2 mL, in the range of 0.225-0.325 mg/2 mL, in the range of 0.325-0.425 mg/2 mL, in the range of 0.425-0.525 mg/2 mL, in the range of 0.525-0.625 mg/2 mL, in the range of 0.625-0.725 mg/2 mL, in the range of 0.725-0.825 mg/2 mL, in the range of 0.825-0.925 mg/2 mL, in the range of 0.925-1.025 mg/2 mL, in the range of 1.025-1.2 mg/2 mL, in the range of 1.2-2 mg/2 mL, in the range of 2-4 mg/2 mL, in the range of 4-6 mg/2 mL, in the range of 6-8 mg/2 mL, or the budesonide may be present in the composition at a concentration in the range of 8-10 mg/2 mL. In certain embodiments, for example, the budesonide may be present in the composition at a concentration in the range of 0.00125-0.5 wt. %, for example the budesonide may be present in the composition at a concentration in the range of 0.00625-0.25 wt. %, in the range of 0.00875-0.25 wt. %, in the range of 0.0125-0.125 wt. %, or the budesonide may be present in the composition at a concentration in the range of 0.0125-0.05 wt. %. In certain embodiments, for example, the budesonide may be present in the composition at a concentration in the range of 0.005-0.02 wt. %, for example the budesonide may be present in the composition at a concentration in the range of 0.0075-0.0175 wt. %, in the range of 0.01-0.015 wt. %, or the budesonide may be present in the composition at a concentration in the range of 0.012-0.03 wt. %. In certain embodiments, for example, the budesonide may be present in the composition at a concentration of 0.0125 wt. %. In certain embodiments, for example, the budesonide may be present in the composition at a concentration of 0.025 wt. %. In certain embodiments, for example, the budesonide may be present in the composition at a concentration of 0.05 wt. %. In certain embodiments, for example, the budesonide may be present in the composition at a concentration in the range of 0.0175-0.0325 wt. %, for example the budesonide may be present in the composition at a concentration in the range of 0.02-0.03 wt. %, in the range of 0.0225-0.0275 wt. %, or the budesonide may be present in the composition at a concentration in the range of 0.024-0.026 wt. %. In certain embodiments, for example, the budesonide may be present in the composition at a concentration in the range of 0.0425-0.0575 wt. %, for example the budesonide may be present in the composition at a concentration in the range of 0.045-0.055 wt. %, in the range of 0.0475-0.0525 wt. %, or the budesonide may be present in the composition at a concentration in the range of 0.049-0.051 wt. %. In certain embodiments, for example, the budesonide may be present in the composition at a concentration in the range of 0.00125-5 wt. %, for example the budesonide may be present in the composition at a concentration in the range of 0.00125-0.00625 wt. %, in the range of 0.00625-0.01125 wt. %, in the range of 0.01125-0.01625 wt. %, in the range of 0.01625-0.02125 wt. %, in the range of 0.02125-0.02625 wt. %, in the range of 0.02625-0.03125 wt. %, in the range of 0.03125-0.03625 wt. %, in the range of 0.03625-0.04125 wt. %, in the range of 0.04125-0.04625 wt. %, in the range of 0.04625-0.05125 wt. %, in the range of 0.05125-0.06 wt. %, in the range of 0.06-0.1 wt. %, in the range of 0.1-0.2 wt. %, in the range of 0.2-0.3 wt. %, in the range of 0.3-0.4 wt. %, or the budesonide may be present in the composition at a concentration in the range of 0.4-0.5 wt. %. In certain embodiments, for example, the budesonide may be present in the composition at a concentration of at least 0.01 wt. %, for example a concentration of at least 0.025 wt. %, at least 0.05 wt. %, at least 0.075 wt. %, at least 0.1 wt. %, at least 0.25 wt. %, or the budesonide may be present in the composition at a concentration of at least 0.5 wt. %.

In certain embodiments, for example, the homogeneous budesonide composition may comprise at least a second drug. In certain embodiments, for example, the second drug may be an active ingredient for treatment of an inflammatory lung disease. In certain further embodiments, for example, the second drug may comprise (for example may consist of formoterol or the formoterol may be present as part of a composition such as formoterol fumarate dihydrate). In certain embodiments, for example, the weight ratio of formoterol to budesonide present in the homogeneous budesonide composition may be less than 50 wt. %, for example less than 10 wt. %, less than 6 wt. %, less than 3 wt. %, less than 2 wt. %, or the weight ratio of formoterol to budesonide present in the homogeneous budesonide composition may be less than 1 wt. %. In certain embodiments, for example, the weight ratio of formoterol to budesonide present in the homogeneous budesonide composition may be in the range of 1-10 wt. %, for example in the range of 2-4 wt. %, in the range of 2.5-3 wt. %, in the range of 5-7 wt. %, or the weight ratio of formoterol to budesonide present in the homogeneous budesonide composition may be in the range of 5.5-6 wt. %. In certain further embodiments, for example, the homogeneous budesonide composition may further comprise formoterol fumarate dihydrate. In certain embodiments, for example, the weight ratio of formoterol fumarate dihydrate to budesonide present in the homogeneous budesonide composition may be less than 50 wt. %, for example less than 10 wt. %, less than 6 wt. %, less than 3 wt. %, less than 2 wt. %, or the weight ratio of formoterol fumarate dihydrate to budesonide present in the homogeneous budesonide composition may be less than 1 wt. %. In certain embodiments, for example, the weight ratio of formoterol fumarate dihydrate to budesonide present in the homogeneous budesonide composition may be in the range of 1-10 wt. %, for example in the range of 2-4 wt. %, in the range of 2.5-3 wt. %, in the range of 5-7 wt. %, or the weight ratio of formoterol fumarate dihydrate to budesonide present in the homogeneous budesonide composition may be in the range of 5.5-6 wt. %. In certain embodiments, for example, the weight ratio of formoterol fumarate dihydrate to budesonide present in the homogeneous budesonide composition may be 2.8125 wt. %. In certain embodiments, for example, the weight ratio of formoterol fumarate dihydrate to budesonide present in the homogeneous budesonide composition may be 5.625 wt. %.

In certain embodiments, for example, the homogeneous budesonide composition may comprise at least 70 wt. % water, for example at least 80 wt. % water, at least 85 wt. % water, at least 90 wt. % water, at least 95 wt. % water, at least 96 wt. % water, at least 97 wt. % water, at least 98 wt. % water, or the aqueous solution may comprise at least 99 wt. % water. In certain embodiments, for example, the homogeneous budesonide composition may comprise in the range of 80-99 wt. % water, for example in the range of 90-99 wt. %, in the range of 93-98 wt. % water, or the homogeneous budesonide composition may comprise in the range of 95-98 wt. % water.

In certain embodiments, for example, the homogeneous budesonide composition may comprise a bifunctional polymer. In certain further embodiments, for example, the bifunctional polymer may be configured to a) reduce precipitation of budesonide in an aqueous solution, and b) remain homogeneously dispersed in the aqueous solution. In certain embodiments, for example, the bifunctional polymer may promote formation of budesonide-containing micelles comprising the bifunctional polymer. In certain embodiments, for example, the bifunctional polymer may promote formation of budesonide-containing micelles comprising a further polymer (for example a micelle comprising the bifunctional polymer and the further polymer). In certain embodiments, for example, the bifunctional polymer may increase the solubility of budesonide in the aqueous solution, for example by a factor of at least 1.5, by a factor of at least 2, by a factor of at least 2.5, by a factor of at least 3, by a factor of at least 4, by a factor of at least 5, by a factor of at least 7.5, or the bifunctional polymer may increase the solubility of budesonide in the aqueous solution by a factor of at least 10, relative to the solubility of budesonide in the aqueous solution exclusive of the bifunctional polymer. In certain embodiments, for example, the bifunctional polymer may increase the solubility of budesonide in the aqueous solution, for example by a factor in the range of 1.5-7.5, for example by a factor in the range of 2-5, relative to the solubility of budesonide in the aqueous solution exclusive of the bifunctional polymer.

In certain embodiments, for example, the homogeneous budesonide composition may comprise budesonide (for example dissolved budesonide or budesonide particles) and the bifunctional polymer, wherein the weight of budesonide may be increased by a factor of at least 1.5, by a factor of at least 2, by a factor of at least 2.5, by a factor of at least 3, by a factor of at least 4, by a factor of at least 5, by a factor of at least 7.5, or by a factor of at least 10, relative to a weight of budesonide calculated based on the solubility of budesonide in the aqueous solution exclusive of the bifunctional polymer. In certain embodiments, for example, the homogeneous budesonide composition may comprise budesonide (for example dissolved budesonide or budesonide particles) and the bifunctional polymer, wherein the weight of the budesonide increased by a factor in the range of 1.5-7.5, for example by a factor in the range of 2-5, relative to a weight of budesonide calculated based on the solubility of budesonide in the aqueous solution exclusive of the bifunctional polymer.

In certain embodiments, for example, the bifunctional polymer may be an amphiphilic polymer comprising hydrophobic and hydrophilic portions. In certain embodiments, for example, the hydrophobic portion may comprise aliphatic groups. In certain embodiments, for example, the hydrophobic portion may comprise aromatic hydrocarbon groups. In certain embodiments, for example, the hydrophilic portion may comprise ionizable groups. In certain embodiments, for example, the hydrophilic portion may comprise non-ionizable groups. In certain embodiments, for example, the hydrophilic portion may comprise one or more hydrogen bonding groups, for example one or more hydroxyl groups, one or more carboxylic acids, one or more esters, one or more amines, one or more amides, or a combination thereof. In certain embodiments, for example, the hydrophilic portion may comprise one or more alkoxy groups, one or more acrylate groups, one or more methacrylate groups, one or more sulphonate groups, one or more carboxylate groups, one or more quaternary ammonium groups, or a combination or a combination of two or more of the foregoing groups.

In certain embodiments, for example, the amphiphilic polymer may interact with budesonide to form a polymer/budesonide assembly in the aqueous solution. In certain embodiments, for example, the size of the polymer/budesonide assembly may be limited due to one or more ionized groups present on the amphiphilic polymer in the aqueous solution. In certain further embodiments, for example, the size of the polymer/budesonide assembly may be less than 1 micron, for example less than 500 nm, less than 250 nm, less than 100 nm, less than 50 nm, or the size of the polymer/budesonide assembly may be less than 10 nm. In certain embodiments, for example, the polymer/drug assembly may comprise budesonide (for example a budesonide molecule or a budesonide particle) surrounded by the amphiphilic polymer, wherein a hydrophobic portion of the amphiphilic polymer is proximate (or oriented towards) the budesonide and a hydrophilic portion of the amphiphilic polymer is proximate (or oriented towards) the surrounding aqueous solution. In certain embodiments, for example, a polar functional group present on the amphiphilic polymer may associate with (for example by hydrogen bonding) with a polar group present on the budesonide. In certain embodiments, for example, the amphiphilic polymer may be an ionizable polymer. In certain further embodiments, for example, the ionizable polymer may comprise at least one hydrophilic ionized functional group. In certain further embodiments, for example, a polymer/drug assembly comprising the ionizable polymer in an aqueous solution may be a charged polymeric micelle. In certain embodiments, for example, the amphiphilic polymer may increase the solubility of budesonide in the aqueous solution, for example by a factor of at least 1.5, by a factor of at least 2, by a factor of at least 2.5, by a factor of at least 3, by a factor of at least 4, by a factor of at least 5, by a factor of at least 7.5, or the amphiphilic polymer may increase the solubility of budesonide in the aqueous solution by a factor of at least 10, relative to the solubility of budesonide in the aqueous solution exclusive of the amphiphilic polymer. In certain embodiments, for example, the amphiphilic polymer may increase the solubility of budesonide in the aqueous solution, for example by a factor in the range of 1.5-7.5, for example by a factor in the range of 2-5, relative to the solubility of budesonide in the aqueous solution exclusive of the amphiphilic polymer.

In certain embodiments, for example, the homogeneous budesonide composition may comprise budesonide (for example dissolved budesonide or budesonide particles) and the amphiphilic polymer, wherein the weight of budesonide may be increased by a factor of at least 1.5, by a factor of at least 2, by a factor of at least 2.5, by a factor of at least 3, by a factor of at least 4, by a factor of at least 5, by a factor of at least 7.5, or by a factor of at least 10, relative to a weight of budesonide calculated based on the solubility of budesonide in the aqueous solution exclusive of the amphiphilic polymer. In certain embodiments, for example, the homogeneous budesonide composition may comprise budesonide (for example dissolved budesonide or budesonide particles) and the amphiphilic polymer, wherein the weight of the budesonide increased by a factor in the range of 1.5-7.5, for example by a factor in the range of 2-5, relative to a weight of budesonide calculated based on the solubility of budesonide in the aqueous solution exclusive of the amphiphilic polymer.

In certain embodiments, for example, the amphiphilic polymer may be selected from the group consisting of a vinyl copolymer having substituents of hydroxyl, alkylacyloxy, and cyclicamido polyvinyl alcohols that have at least a portion of their repeat units in the unhydrolyzed (vinyl acetate) form; a polyvinyl alcohol polyvinyl acetate copolymer; a polyvinyl pyrrolidone; a polyvinylpyrrolidone vinyl acetate; a polyethylene polyvinyl alcohol copolymer; a ionizable non-cellulosic polymer, including, but not limited to, a carboxylic acid-functionalized vinyl polymer, such as a carboxylic acid functionalized polymethacrylate or a carboxylic acid functionalized polyacrylate (for example a copolymers of methacrylates and acrylates sold under the EUDRAGITS trademark); an amine-functionalized polyacrylate or polymethacrylate; a proteins; a carboxylic acid functionalized starch such as starch glycolate; a non-cellulosic copolymer such as acrylate and methacrylate copolymer; a cellulosic polymers such as methyl cellulose, ethyl cellulose, hydroxyethyl cellulose, hydroxyethyl methyl cellulose, hydroxypropyl cellulose, hydroxypropyl methyl cellulose, hydroxypropyl methyl cellulose phthalate, hydroxypropyl methyl cellulose acetate, hydroxypropyl methyl cellulose acetate succinate, hydroxypropyl cellulose acetate succinate, hydroxyethyl cellulose acetate succinate, hydroxyethyl methyl cellulose succinate, hydroxyethyl methyl cellulose acetate succinate, carboxymethyl cellulose, carboxyethyl cellulose, carboxymethyl ethyl cellulose, hydroxypropyl methyl cellulose acetate phthalate, hydroxypropyl methyl cellulose acetate trimellitate; a polyvinyl alcohol; a polyvinyl pyrrolidone; a polyvinyl acetate; a vinylpyrrolidon vinylacetat copolymer (for example the copolymer sold under the trade name COPOVIDON KOLLIDON VA 64); a polyvinylacetate polyvinyl pyrrolidone copolymer; a polyvinyl polypyrrolidone; a polyvinyl alcohol polyethylene glycol copolymer; a polypropylene glycol; polyethylene glycols (for example PEG 300, 400, 500, 600, 700, 800, 900, 1000, 1500, 3000, 3350, 4000, 6000, 8000, 10000, 12000, 20000); a polyoxyethylene polyoxypropylene copolymer (for example the copolymers sold under the trade name POLOXAMERS); apolyoxyethylene-polyoxypropylene copolymers (such as the apolyoxyethylene-polyoxypropylene copolymer sold under the PLURONICS trademark); gum traganth; alginates; gum Arabic; and gum guar. In certain embodiments, for example, the homogeneous budesonide composition may comprise a mixture of two or more of the foregoing polymers (or their derivatives)

In certain embodiments, for example, the homogeneous budesonide composition may comprise a polyvinyl caprolactam-polyvinyl acetate-polyethylene glycol graft copolymer. In certain embodiments, for example, the homogeneous budesonide composition may comprise a polyvinyl caprolactam-polyvinyl acetate-polyethylene glycol graft copolymer-containing composition sold by BASF SE under the SOLUPLUS trademark. SOLUPLUS is a free flowing white to slightly yellowish granule with a faint characteristic odor having the following chemical structure:

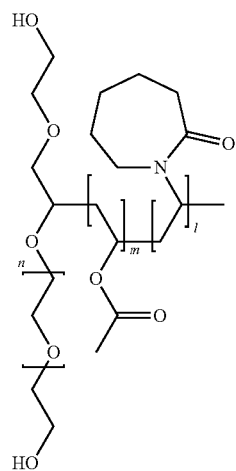

In certain embodiments, for example, forming the homogeneous budesonide composition may comprise introducing a polyvinyl caprolactam-polyvinyl acetate-polyethylene glycol graft copolymer-containing composition in a liquid to at least one component of the homogeneous budesonide composition. In certain embodiments, for example, forming the homogeneous budesonide composition may comprise introducing a polyvinyl caprolactam-polyvinyl acetate-polyethylene glycol graft copolymer-containing composition in solid form to at least one component of the homogeneous budesonide composition. In certain embodiments, for example, forming the homogeneous budesonide composition may comprise introducing a mixture to at least one component of the homogeneous budesonide composition, wherein the mixture may comprise a polyvinyl caprolactam-polyvinyl acetate-polyethylene glycol graft copolymer and one or more other components (for example one or more excipients).

In certain embodiments, for example, the polyvinyl caprolactam-polyvinyl acetate-polyethylene glycol graft copolymer may have an average molecular weight in the range of 90,000-140,000 Daltons. In certain embodiments, for example, the polyvinyl caprolactam-polyvinyl acetate-polyethylene glycol graft copolymer may have a polyethylene glycol backbone with one or two side chains. In certain embodiments, for example, the polyethylene glycol backbone may have an average molecular weight of 1,000 or more (for example 3,000 or more). In certain embodiments, for example, the polyethylene glycol backbone may have an average molecular weight of 20,000 or less (for example 10,000 or less). In certain embodiments, for example, each side chain of the polyethylene glycol backbone may be a random copolymer of vinyl acetate and N-vinyl caprolactam. In certain embodiments, for example, the polyvinyl caprolactam-polyvinyl acetate-polyethylene glycol graft copolymer may have an average molecular weight of 30,000 or higher (for example 50,000 or higher, such as or 70,000 or higher). In certain embodiments, for example, the polyvinyl caprolactam-polyvinyl acetate-polyethylene glycol graft copolymer may have an average molecular weight of 1,000,000 or lower (for example 500,000 or lower, such as 200,000 or lower). In certain embodiments, for example, the amount of polyethylene glycol backbone in the polyvinyl caprolactam-polyvinyl acetate-polyethylene glycol graft copolymer may be, by weight based on the weight of the polyvinyl caprolactam-polyvinyl acetate-polyethylene glycol graft copolymer, 3% or more, (for example 5% or more such as 7% or more). In certain embodiments, for example, the amount of polyethylene glycol backbone in the polyvinyl caprolactam-polyvinyl acetate-polyethylene glycol graft copolymer may be, by weight based on the weight of the polyvinyl caprolactam-polyvinyl acetate-polyethylene glycol graft copolymer, 50% or less (for example 35% or less, such as 25% or less). In certain embodiments, for example, the amount of polymerized units of vinyl acetate in the polyvinyl caprolactam-polyvinyl acetate-polyethylene glycol graft copolymer may be, by weight based on the weight of the polyvinyl caprolactam-polyvinyl acetate-polyethylene glycol graft copolymer, 5% or more (for example 10% or more, such as 15% or more). Preferably, the amount of polymerized units of vinyl acetate in the polyvinyl caprolactam-polyvinyl acetate-polyethylene glycol graft copolymer may be, by weight based on the weight of the polyvinyl caprolactam-polyvinyl acetate-polyethylene glycol graft copolymer, 70% or less (for example 60% or less, such as 50% or less). In certain embodiments, for example, the amount of polymerized units of vinyl caprolactam in the polyvinyl caprolactam-polyvinyl acetate-polyethylene glycol graft copolymer may be, by weight based on the weight of the polyvinyl caprolactam-polyvinyl acetate-polyethylene glycol graft copolymer, 10% or more (for example 20% or more, such as 30% or more). In certain embodiments, for example, the amount of polymerized units of vinyl caprolactam in the polyvinyl caprolactam-polyvinyl acetate-polyethylene glycol graft copolymer may be, by weight based on the weight of the polyvinyl caprolactam-polyvinyl acetate-polyethylene glycol graft copolymer, 90% or less (for example as 80% or less).

In certain embodiments, for example, the polyvinyl caprolactam-polyvinyl acetate-polyethylene glycol graft copolymer may be soluble in water. In certain embodiments, for example, the polyvinyl caprolactam-polyvinyl acetate-polyethylene glycol graft copolymer may be soluble in a buffer (for example an aqueous buffer). In certain embodiments, for example, the polyvinyl caprolactam-polyvinyl acetate-polyethylene glycol graft copolymer may be soluble in acetone at a concentration of up to 50 wt. % of the polyvinyl caprolactam-polyvinyl acetate-polyethylene glycol graft copolymer. In certain embodiments, for example, the polyvinyl caprolactam-polyvinyl acetate-polyethylene glycol graft copolymer may be at least partially soluble in certain alcohols, including but not limited to: ethanol at a concentration of up to 50 wt. % of the polyvinyl caprolactam-polyvinyl acetate-polyethylene glycol graft copolymer; propylene glycol, at a concentration of up to 50 wt. % of the polyvinyl caprolactam-polyvinyl acetate-polyethylene glycol graft copolymer; polyhydric alcohols; and organic, water-soluble glycols. In certain embodiments, for example, the polyvinyl caprolactam-polyvinyl acetate-polyethylene glycol graft copolymer may be present in the homogeneous budesonide composition at a concentration of less than 1 wt. %, for example at a concentration of less than 0.9 wt. %, less than 0.8 wt. %, less than 0.7 wt. %, less than 0.6 wt. %, less than 0.5 wt. %, less than 0.4 wt. %, less than 0.3 wt. %, less than 0.2 wt. %, less than 0.1 wt. %, less than 0.075 wt. %, less than 0.05 wt. %, less than 0.025 wt. %, or the polyvinyl caprolactam-polyvinyl acetate-polyethylene glycol graft copolymer may be present in the homogeneous budesonide composition at a concentration of less 0.01 wt. %. In certain embodiments, for example, the polyvinyl caprolactam-polyvinyl acetate-polyethylene glycol graft copolymer may be present in the homogeneous budesonide composition at a concentration in the range of 0.1-0.75 wt. %, for example in the range of 0.2-0.6 wt. %, in the range of 0.3-0.5 wt. %, or the polyvinyl caprolactam-polyvinyl acetate-polyethylene glycol graft copolymer may be present in the homogeneous budesonide composition at a concentration in the range of 0.4-0.5 wt. %. In certain embodiments, for example, the polyvinyl caprolactam-polyvinyl acetate-polyethylene glycol graft copolymer may be present in the homogeneous budesonide composition at a concentration in the range of 0.01-0.1 wt. %, for example in the range of 0.02-0.04 wt. %, in the range of 0.025-0.035 wt. %, or the polyvinyl caprolactam-polyvinyl acetate-polyethylene glycol graft copolymer may be present in the homogeneous budesonide composition at a concentration in the range of 0.0275-0.0325 wt. %.

In certain embodiments, for example, the polyvinyl caprolactam-polyvinyl acetate-polyethylene glycol graft copolymer may be present in the homogeneous budesonide composition at a ratio, relative to the budesonide, of less than 10:1, for example at a ratio of less than 5:1, less than 4:1, less than 3:1, less than 2:1, less than 1.75:1, less than 1.5:1, less than 1.25:1, less than 1:1, less than 0.75:1, less than 0.5:1, or the polyvinyl caprolactam-polyvinyl acetate-polyethylene glycol graft copolymer may be present in the homogeneous budesonide composition at a ratio, relative to the budesonide, of less than 0.25:1. In certain embodiments, for example, the polyvinyl caprolactam-polyvinyl acetate-polyethylene glycol graft copolymer may be present in the homogeneous budesonide composition at a ratio, relative to the budesonide, of no more than 10:1, for example at a ratio of no more than 5:1 (for example in the range of 1:1-5:1, in the range of 2:1-5:1, in the range of 3:1-5:1, in the range of 4:1-5:1, or in the range of 4.5:1-5:1), no more than 4.5:1 (for example in the range of 1:1-4.5:1, in the range of 2:1-4.5:1, in the range of 3:1-4.5:1, or in the range of 4:1-4.5:1), no more than 4:1 (for example in the range of 1:1-4:1, in the range of 2:1-4:1, or in the range of 3:1-4:1), no more than 3:1 (for example in the range of 1:1-3:1, or in the range of 2:1-3:1), no more than 2:1 (for example in the range of 1:1-2:1), no more than 1.75:1, no more than 1.5:1, no more than 1.25:1, no more than 1:1, no more than 0.75:1, no more than 0.5:1, or the polyvinyl caprolactam-polyvinyl acetate-polyethylene glycol graft copolymer may be present in the homogeneous budesonide composition at a ratio, relative to the budesonide, of no more than 0.25:1. In certain embodiments, for example, the polyvinyl caprolactam-polyvinyl acetate-polyethylene glycol graft copolymer may be present in the homogeneous budesonide composition at a ratio, relative to the budesonide, in the range of 0.25:1-10:1, for example a ratio in the range of 0.75:1-1.75:1, at a ratio in the range of 1:1-1.5:1, in the range of 1:1-1.25:1, in the range of 1.25:1-1.5:1, in the range of 2:1-5:1, in the range of 2:1-3:1, in the range of 3:1-4:1, or the polyvinyl caprolactam-polyvinyl acetate-polyethylene glycol graft copolymer may be present in the homogeneous budesonide composition at a ratio, relative to the budesonide, in the range of 4:1-5:1.

In certain embodiments, for example, the homogeneous budesonide composition comprising budesonide may further comprise one or more polysorbates (for example one type of polysorbate such as polysorbate 80), for example one or more polysorbates sold under the TWEEN trademark from ICI Americas, Inc. In certain embodiments, for example, the one or more polysorbates may comprise polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), polysorbate 85 (polyoxyethylene (20) sorbitan trioleate), or a mixture of or a combination of two or more of the foregoing polysorbates.

In certain embodiments, for example, the homogeneous budesonide composition comprising budesonide may further comprise polysorbate 80. In certain embodiments, for example, the polysorbate 80 may be present in the homogeneous budesonide composition at a concentration of less than 1 wt. %, for example at a concentration of less than 0.9 wt. %, less than 0.8 wt. %, less than 0.7 wt. %, less than 0.6 wt. %, less than 0.5 wt. %, less than 0.4 wt. %, less than 0.3 wt. %, less than 0.2 wt. %, less than 0.1 wt. %, less than 0.075 wt. %, less than 0.05 wt. %, less than 0.25 wt. %, or the polysorbate 80 may be present in the homogeneous budesonide composition at a concentration of less 0.01 wt. %. In certain embodiments, for example, the polysorbate 80 may be present in the homogeneous budesonide composition at a concentration in the range of 0.1-0.75 wt. %, for example in the range of 0.2-0.8 wt. %, in the range of 0.3-0.7 wt. %, or the polysorbate 80 may be present in the homogeneous budesonide composition at a concentration in the range of 0.4-0.6 wt. %. In certain embodiments, for example, the polysorbate 80 may be present in the homogeneous budesonide composition at a concentration in the range of 0.01-0.1 wt. %, for example in the range of 0.02-0.07 wt. %, in the range of 0.03-0.05 wt. %, or the polysorbate 80 may be present in the homogeneous budesonide composition at a concentration in the range of 0.035-0.05 wt. %.

In certain embodiments, for example, the polysorbate 80 may be present in the homogeneous budesonide composition at a ratio, relative to the budesonide, of less than 2:1, for example at a ratio of less than 1.75:1, less than 1.5:1, less than 1.25:1, less than 1:1, less than 0.75:1, less than 0.5:1, or the polysorbate 80 may be present in the homogeneous budesonide composition at a ratio, relative to the budesonide, of less than 0.25:1. In certain embodiments, for example, the polysorbate 80 may be present in the homogeneous budesonide composition at a ratio, relative to the budesonide, of no more than 2:1, for example at a ratio of no more than 1.75:1, no more than 1.5:1, no more than 1.25:1, no more than 1:1, no more than 0.75:1, no more than 0.5:1, or the polysorbate 80 may be present in the homogeneous budesonide composition at a ratio, relative to the budesonide, of no more than 0.25:1. In certain embodiments, for example, the polysorbate 80 may be present in the homogeneous budesonide composition at a ratio, relative to the budesonide, in the range of 0.5-2, for example a ratio in the range of 0.75-1.75, at a ratio in the range of 1-1.5, in the range of 1-1.25, or the polysorbate 80 may be present in the homogeneous budesonide composition at a ratio, relative to the budesonide, in the range of 1.25-1.5.

In certain embodiments, for example, the homogenous budesonide composition (for example a master batch or a drug product composition) may comprise one or more alcohols. In certain embodiments, for example, the one or more alcohols may comprise an organic glycol. In certain further embodiments, for example, the one or more alcohols may comprise an organic glycol that is at least partially soluble in water. In certain embodiments, for example, the one or more alcohols may comprise ethanol and/or propanol. In certain embodiments, for example, the one or more alcohols may comprise propylene glycol and ethanol. In certain embodiments, for example, homogeneous budesonide composition may comprise less than 90 wt. % of the one or more alcohols, for example less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the homogeneous budesonide composition may comprise less than 1 wt. % of the one or more alcohols. In certain embodiments, for example, the homogeneous budesonide composition may comprise in the range of 1-90 wt. % of the one or more alcohols, for example in the range of 1-10 wt. %, in the range of 2-8 wt. %, in the range of 3-7 wt. %, in the range of 4-6 wt. %, in the range of 1-2 wt. %, in the range of 2-4 wt. %, in the range of 6-8 wt. %, or the homogeneous budesonide composition may comprise in the range of 8-10 wt. % of the one or more alcohols. In certain embodiments, for example, the homogeneous budesonide composition may comprise in the range of 50-90 wt. % of the one or more alcohols, for example in the range of 60-80 wt. %, in the range of 65-75 wt. %, in the range of 68-72 wt. %, in the range of 50-55 wt. %, in the range of 55-60 wt. %, in the range of 60-65 wt. %, in the range of 65-70 wt. %, in the range of 70-75 wt. %, in the range of 75-80 wt. %, in the range of 80-85 wt. %, or the homogeneous budesonide composition may comprise in the range of 85-90 wt. % of the one or more alcohols.

In certain embodiments, for example, the at least one alcohol may comprise propylene glycol, or a derivative thereof. In certain embodiments, for example, the one or more alcohols may comprise less than 90 wt. % propylene glycol relative to the total weight of the homogeneous budesonide composition, for example less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the one or more alcohols may comprise less than 1 wt. % propylene glycol relative to the total weight of the homogeneous budesonide composition. In certain embodiments, for example, the one or more alcohols may comprise in the range of 1-90 wt. % propylene glycol relative to the total weight of the homogeneous budesonide composition, for example in the range of 1-10 wt. %, in the range of 2-8 wt. %, in the range of 3-7 wt. %, in the range of 4-6 wt. %, in the range of 1-2 wt. %, in the range of 2-4 wt. %, in the range of 6-8 wt. %, or the one or more alcohols may comprise in the range of 8-10 wt. % propylene glycol relative to the total weight of the homogeneous budesonide composition. In certain embodiments, for example, the one or more alcohols may comprise in the range of 50-90 wt. % propylene glycol relative to the total weight of the homogeneous budesonide composition, for example in the range of 60-80 wt. %, in the range of 65-75 wt. %, in the range of 68-72 wt. %, in the range of 50-55 wt. %, in the range of 55-60 wt. %, in the range of 60-65 wt. %, in the range of 65-70 wt. %, in the range of 70-75 wt. %, in the range of 75-80 wt. %, in the range of 80-85 wt. %, or the one or more alcohols may comprise in the range of 85-90 wt. % propylene glycol relative to the total weight of the homogeneous budesonide composition.

In certain embodiments, for example, the one or more alcohols may comprise ethylene glycol, or a derivative thereof. In certain embodiments, for example, the one or more alcohols may comprise less than 90 wt. % ethylene glycol relative to the total weight of the homogeneous budesonide composition, for example less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the one or more alcohols may comprise less than 1 wt. % ethylene glycol relative to the total weight of the homogeneous budesonide composition. In certain embodiments, for example, the one or more alcohols may comprise in the range of 1-90 wt. % ethylene glycol relative to the total weight of the homogeneous budesonide composition, for example in the range of 1-10 wt. %, in the range of 2-8 wt. %, in the range of 3-7 wt. %, in the range of 4-6 wt. %, in the range of 1-2 wt. %, in the range of 2-4 wt. %, in the range of 6-8 wt. %, or the one or more alcohols may comprise in the range of 8-10 wt. % ethylene glycol relative to the total weight of the homogeneous budesonide composition. In certain embodiments, for example, the one or more alcohols may comprise in the range of 50-90 wt. % ethylene glycol relative to the total weight of the homogeneous budesonide composition, for example in the range of 60-80 wt. %, in the range of 65-75 wt. %, in the range of 68-72 wt. %, in the range of 50-55 wt. %, in the range of 55-60 wt. %, in the range of 60-65 wt. %, in the range of 65-70 wt. %, in the range of 70-75 wt. %, in the range of 75-80 wt. %, in the range of 80-85 wt. %, or the one or more alcohols may comprise in the range of 85-90 wt. % ethylene glycol relative to the total weight of the homogeneous budesonide composition.

In certain embodiments, for example, the one or more alcohols may comprise ethanol, or a derivative thereof. In certain embodiments, for example, the one or more alcohols may comprise less than 90 wt. % ethanol relative to the total weight of the homogeneous budesonide composition, for example less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the one or more alcohols may comprise less than 1 wt. % ethanol relative to the total weight of the homogeneous budesonide composition. In certain embodiments, for example, the one or more alcohols may comprise in the range of 1-90 wt. % ethanol relative to the total weight of the homogeneous budesonide composition, for example in the range of 1-10 wt. %, in the range of 2-8 wt. %, in the range of 3-7 wt. %, in the range of 4-6 wt. %, in the range of 1-2 wt. %, in the range of 2-4 wt. %, in the range of 6-8 wt. %, or the one or more alcohols may comprise in the range of 8-10 wt. % ethanol relative to the total weight of the homogeneous budesonide composition. In certain embodiments, for example, the one or more alcohols may comprise in the range of 50-90 wt. % ethanol relative to the total weight of the homogeneous budesonide composition, for example in the range of 60-80 wt. %, in the range of 65-75 wt. %, in the range of 68-72 wt. %, in the range of 50-55 wt. %, in the range of 55-60 wt. %, in the range of 60-65 wt. %, in the range of 65-70 wt. %, in the range of 70-75 wt. %, in the range of 75-80 wt. %, in the range of 80-85 wt. %, or the one or more alcohols may comprise in the range of 85-90 wt. % ethanol relative to the total weight of the homogeneous budesonide composition.

In certain embodiments, for example, the one or more alcohols may comprise a polyol. In certain further embodiments, for example, the one or more alcohols may comprise a polyhydric alcohol.

In certain embodiments, for example, the one or more alcohols may comprise polyhedric alcohol, or a derivative thereof. In certain embodiments, for example, the one or more alcohols may comprise less than 90 wt. % polyhedric alcohol relative to the total weight of the homogeneous budesonide composition, for example less than 85 wt. %, less than 80 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the one or more alcohols may comprise less than 1 wt. % polyhedric alcohol relative to the total weight of the homogeneous budesonide composition. In certain embodiments, for example, the one or more alcohols may comprise in the range of 1-90 wt. % polyhedric alcohol relative to the total weight of the homogeneous budesonide composition, for example in the range of 1-10 wt. %, in the range of 2-8 wt. %, in the range of 3-7 wt. %, in the range of 4-6 wt. %, in the range of 1-2 wt. %, in the range of 2-4 wt. %, in the range of 6-8 wt. %, or the one or more alcohols may comprise in the range of 8-10 wt. % polyhedric alcohol relative to the total weight of the homogeneous budesonide composition. In certain embodiments, for example, the one or more alcohols may comprise in the range of 50-90 wt. % polyhedric alcohol relative to the total weight of the homogeneous budesonide composition, for example in the range of 60-80 wt. %, in the range of 65-75 wt. %, in the range of 68-72 wt. %, in the range of 50-55 wt. %, in the range of 55-60 wt. %, in the range of 60-65 wt. %, in the range of 65-70 wt. %, in the range of 70-75 wt. %, in the range of 75-80 wt. %, in the range of 80-85 wt. %, or the one or more alcohols may comprise in the range of 85-90 wt. % polyhedric alcohol relative to the total weight of the homogeneous budesonide composition.

In certain embodiments, for example, the homogenous budesonide composition may comprise water. In certain embodiments, for example, the homogenous budesonide composition may comprise less than 99 wt. % water, for example less than 95 wt. %, less than 90 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the homogenous budesonide composition may comprise less than 1 wt. % water. In certain embodiments, for example, the homogenous budesonide composition may comprise in the range of 1-99 wt. % water, for example in the range of 1-10 wt. %, in the range of 10-20 wt. %, in the range of 20-30 wt. %, in the range of 30-40 wt. %, in the range of 40-50 wt. %, in the range of 50-60 wt. %, in the range of 60-70 wt. %, in the range of 70-80 wt. %, in the range of 80-90 wt. %, in the range of 90-95 wt. %, or the homogenous budesonide composition may comprise in the range of 95-99 wt. % water. In certain embodiments, for example, the homogenous budesonide composition may comprise in the range of 10-40 wt. % water, for example in the range of 15-35 wt. %, in the range of 20-30 wt. %, in the range of 25-30 wt. %, or the homogenous budesonide composition may comprise in the range of 26-29 wt. % water. In certain embodiments In certain embodiments, for example, the homogenous budesonide composition may comprise 28 wt. % water, 28.5 wt. % water, or 29 wt. % water. In certain embodiments, for example, the homogenous budesonide composition may comprise in the range of 80-99 wt. % water, for example in the range of 85-99 wt. %, in the range of 90-99 wt. %, in the range of 92-97 wt. %, or the homogenous budesonide composition may comprise in the range of 94-96 wt. % water. In certain embodiments In certain embodiments, for example, the homogenous budesonide composition may comprise 94.9 wt. % water.

In certain embodiments, for example, the homogenous budesonide composition may have a pH in the range of 2-6, for example a pH in the range of 2-5, in the range of 2-4.5, a pH in the range of 2.5-3.5, in the range of 2.7-3.2, in the range of 4-6, in the range of 4-5, or the homogenous budesonide composition may have a pH in the range of 4.2-4.7. In certain embodiments, for example, the pH of the homogeneous budesonide composition may be adjusted by adding a quantity of one or more pharmaceutically acceptable acids. In certain embodiments, for example, the one or more pharmaceutically acceptable acids may be an inorganic acid, such as hydrochloric acid, hydrobromic acid, nitric acid, sulfuric acid, and phosphoric acid, or a combination of two or more of the foregoing acids. In certain embodiments, for example, the one or more pharmaceutically acceptable acids may comprise one or more organic acids, such as ascorbic acid, citric acid, malic acid, maleic acid, tartaric acid, succinic acid, fumaric acid, acetic acid, formic acid, propionic acid, or a combination of two or more of the foregoing acids. In certain embodiments, for example, the pH of the homogeneous budesonide solution may be adjusted by adding a quantity of 1 N hydrochloric acid or 1 N sulfuric acid. In certain embodiments, for example, the pH of the homogeneous budesonide solution may be adjusted by adding a quantity of one or more organic acids selected from the group consisting of ascorbic acid, fumaric acid, citric acid, and combinations of two or more of the foregoing acids. In certain embodiments, for example, mixtures of two or more of the above-mentioned acids may be used.

In certain embodiments, for example, the homogeneous budesonide composition may be iso-osmolal with respect to fluids in the lungs. In certain embodiments, for example, the homogeneous budesonide composition may be iso-osmolal with respect to fluids in the eye. In certain embodiments, for example, the homogeneous budesonide composition may be iso-osmolal with respect to fluids in the nose. In certain embodiments, for example, the homogeneous budesonide composition may have an osmolality in the range of 200-500 mOsm/kg, for example the homogeneous budesonide composition may have an osmolality in the range of 175-330 mOsm/kg, in the range of 275-325 mOsm/kg, or the homogeneous budesonide composition may have an osmolality in the range of 280-320 mOsm/kg. In certain embodiments, for example, the osmolality and/or tonicity of the homogeneous budesonide solution may be adjusted by adding a quantity of ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethyl sulfoxide, edetate disodium, edetate trisodium monohydrate, fluorescein sodium, fructose, galactose, glycerin, lactic acid, lactose, magnesium chloride, magnesium sulfate, mannitol, PEG (for example PEG 300), potassium acetate, potassium chlorate, potassium chloride, potassium iodide, potassium chloride, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thio sulfate, sorbitol, sucrose, tartaric acid, triethanolamine, urea, urethan, uridine, zinc sulfate, one or more monosaccharides, or a combination of two or more of the foregoing components. In certain embodiments, for example, the homogeneous budesonide composition may be isotonic with respect to fluids in the lungs. In certain embodiments, for example, the homogeneous budesonide composition may be isotonic with respect to fluids in the eye. In certain embodiments, for example, the homogeneous budesonide composition may be isotonic with respect to fluids in the nose.

In certain embodiments, for example, the homogeneous budesonide composition may comprise citric acid at a concentration in the range of 0.005-0.2 wt. %, for example at a concentration in the range of 0.0075-0.02 wt. %, in the range of 0.01-0.0175 wt. %, in the range of 0.0125-0.0175 wt. %, or the homogeneous budesonide composition may comprise citric acid at a concentration in the range of 0.015-0.0175 wt. %. In certain embodiments, for example, the homogeneous budesonide composition may comprise citric acid at a concentration in the range of 0.02-0.2 wt. %, for example at a concentration in the range of 0.01-0.1 wt. %, in the range of 0.02-0.075 wt. %, in the range of 0.04-0.07 wt. %, or the homogeneous budesonide composition may comprise citric acid at a concentration in the range of 0.05-0.06 wt. %. In certain embodiments, for example, the homogeneous budesonide composition may comprise citric acid at a concentration of 0.053 wt. %. In certain embodiments, for example, the homogeneous budesonide composition may comprise citric acid at a concentration of 0.016 wt. %. In certain embodiments, for example, the homogeneous budesonide composition may comprise citric acid at a concentration of less than 0.1 wt. %, for example a concentration of less than 0.075 wt. %, less than 0.06 wt. %, less than 0.05 wt. %, less than 0.04 wt. %, less than 0.03 wt. %, less than 0.02 wt. %, or the homogeneous budesonide composition may comprise citric acid at a concentration of less than 0.01 wt. %. In certain embodiments, for example, the homogeneous budesonide composition may comprise citric acid at a concentration of at least 0.01 wt. %, for example a concentration of at least 0.02 wt. %, at least 0.03 wt. %, at least 0.04 wt. %, or the homogeneous budesonide composition may comprise citric acid at a concentration of at least 0.05 wt. %.

In certain embodiments, for example, the homogeneous budesonide composition may comprise sodium chloride at a concentration in the range of 0.01-2 wt. %, for example at a concentration in the range of 0.25-1.75 wt. %, in the range of 0.5-1.5 wt. %, in the range of 0.75-1.25 wt. %, or the homogeneous budesonide composition may comprise sodium chloride at a concentration in the range of 0.8-0.825 wt. %. In certain embodiments, for example, the homogeneous budesonide composition may comprise sodium chloride at a concentration of less than 1 wt. %, for example at a concentration of less than 0.85 wt. %. In certain embodiments, for example, the homogeneous budesonide composition may comprise sodium chloride at a concentration of 0.82 wt. %.

In certain embodiments, for example, the homogeneous budesonide composition may comprise sodium citrate at a concentration in the range of 0.005-0.2 wt. %, for example at a concentration in the range of 0.0075-0.02 wt. %, in the range of 0.01-0.0175 wt. %, in the range of 0.0125-0.0175 wt. %, or the homogeneous budesonide composition may comprise sodium citrate at a concentration in the range of 0.0125-0.014 wt. %. In certain embodiments, for example, the homogeneous budesonide composition may comprise sodium citrate at a concentration in the range of 0.02-0.2 wt. %, for example at a concentration in the range of 0.01-0.1 wt. %, in the range of 0.02-0.075 wt. %, in the range of 0.03-0.06 wt. %, or the homogeneous budesonide composition may comprise sodium citrate at a concentration in the range of 0.04-0.05 wt. %. In certain embodiments, for example, the homogeneous budesonide composition may comprise sodium citrate at a concentration of 0.0456 wt. %. In certain embodiments, for example, the homogeneous budesonide composition may comprise sodium citrate at a concentration of 0.014 wt. %. In certain embodiments, for example, the homogeneous budesonide composition may comprise sodium citrate at a concentration of less than 0.1 wt. %, for example a concentration of less than 0.075 wt. %, less than 0.06 wt. %, less than 0.05 wt. %, less than 0.04 wt. %, less than 0.03 wt. %, less than 0.02 wt. %, or the homogeneous budesonide composition may comprise sodium citrate at a concentration of less than 0.01 wt. %. In certain embodiments, for example, the homogeneous budesonide composition may comprise sodium citrate at a concentration of at least 0.01 wt. %, for example a concentration of at least 0.02 wt. %, at least 0.03 wt. %, at least 0.04 wt. %, or the homogeneous budesonide composition may comprise sodium citrate at a concentration of at least 0.05 wt. %. In the foregoing embodiments, sodium citrate may refer to anhydrous sodium citrate or hydrated sodium citrate, for example sodium citrate dihydrate.

In certain embodiments, for example, the homogeneous budesonide composition may be complexing agent-free, for example free of ethylenediaminetetraacetic acid (EDTA). In certain embodiments, for example, the homogeneous budesonide composition may comprise EDTA at a concentration in the range of 0.0001-0.02 wt. % EDTA, for example at a concentration in the range of 0.0025-0.0175 wt. %, in the range of 0.0005-0.0015 wt. %, in the range of 0.0075-0.0125 wt. %, or the homogeneous budesonide composition may comprise EDTA at a concentration in the range of 0.009-0.012 wt. %. In certain embodiments, for example, the homogeneous budesonide composition may comprise EDTA at a concentration in the range of 0.0001-0.01 wt. % EDTA, for example at a concentration in the range of 0.00075-0.0075 wt. %, in the range of 0.001-0.0075 wt. %, in the range of 0.001-0.005 wt. %, or the homogeneous budesonide composition may comprise EDTA at a concentration in the range of 0.002-0.003 wt. %. In certain embodiments, for example, the homogeneous budesonide composition may comprise EDTA at a concentration of 0.0095 wt. %. In certain embodiments, for example, the homogeneous budesonide composition may comprise EDTA at a concentration of 0.003 wt. %. In certain embodiments, for example, the homogeneous budesonide composition may comprise EDTA at a concentration of less than 0.02 wt. %, for example at a concentration of less than 0.015 wt. %, less than 0.01 wt. %, a concentration of less than 0.005 wt. %, or the homogeneous budesonide composition may comprise EDTA at a concentration of less than 0.003 wt. %.

In certain embodiments, for example, the homogenous budesonide composition (for example a master batch or a drug product solution) may comprise 10-99 wt. % buffer. In certain embodiments, for example, the homogenous budesonide composition may comprise buffer. In certain embodiments, for example, the homogenous budesonide composition may comprise less than 99 wt. % buffer, for example less than 95 wt. %, less than 90 wt. %, less than 75 wt. %, less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, less than 20 wt. %, less than 15 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. % or the homogenous budesonide composition may comprise less than 1 wt. % buffer. In certain embodiments, for example, the homogenous budesonide composition may comprise in the range of 1-99 wt. % buffer, for example in the range of 1-10 wt. %, in the range of 10-20 wt. %, in the range of 20-30 wt. %, in the range of 30-40 wt. %, in the range of 40-50 wt. %, in the range of 50-60 wt. %, in the range of 60-70 wt. %, in the range of 70-80 wt. %, in the range of 80-90 wt. %, in the range of 90-95 wt. %, or the homogenous budesonide composition may comprise in the range of 95-99 wt. % buffer. In certain embodiments, for example, the homogenous budesonide composition may comprise in the range of 10-40 wt. % buffer, for example in the range of 15-35 wt. %, in the range of 20-30 wt. %, in the range of 25-30 wt. %, or the homogenous budesonide composition may comprise in the range of 26-29 wt. % buffer. In certain embodiments In certain embodiments, for example, the homogenous budesonide composition may comprise 28 wt. % buffer, 28.5 wt. % buffer, or 29 wt. % buffer. In certain embodiments, for example, the homogenous budesonide composition may comprise in the range of 80-99 wt. % buffer, for example in the range of 85-99 wt. %, in the range of 90-99 wt. %, in the range of 92-97 wt. %, or the homogenous budesonide composition may comprise in the range of 94-96 wt. % buffer. In certain embodiments In certain embodiments, for example, the homogenous budesonide composition may comprise 94.9 wt. % buffer.

In certain embodiments, one or more than one (including for instance all) of the following embodiments may comprise each of the embodiments or parts thereof. In certain embodiments, for example, the buffer may comprise ethylenediaminetetraacetic acid (EDTA). In certain embodiments, for example, the buffer may comprise citric acid. In certain embodiments, for example, the buffer may comprise sodium citrate. In certain embodiments, for example, the buffer may comprise sodium chloride.

In certain of the foregoing embodiments in which EDTA is present in the buffer, for example, the EDTA may be present in the buffer at a concentration in the range of 0.0001-0.02 wt. % EDTA, for example at a concentration in the range of 0.0025-0.0175 wt. %, in the range of 0.0005-0.0015 wt. %, in the range of 0.0075-0.0125 wt. %, or the EDTA may be present in the buffer at a concentration in the range of 0.009-0.012 wt. %. In certain embodiments, for example, the EDTA may be present in the buffer at a concentration in the range of 0.0001-0.01 wt. % EDTA, for example at a concentration in the range of 0.00075-0.0075 wt. %, in the range of 0.001-0.0075 wt. %, in the range of 0.001-0.005 wt. %, or the EDTA may be present in the buffer at a concentration in the range of 0.002-0.003 wt. %. In certain embodiments, for example, the EDTA may be present in the buffer at a concentration of 0.01 wt. %. In certain embodiments, for example, the EDTA may be present in the buffer at a concentration of 0.003 wt. %. In certain embodiments, for example, the EDTA may be present in the buffer at a concentration of less than 0.02 wt. %, for example at a concentration of less than 0.015 wt. %, less than 0.01 wt. %, a concentration of less than 0.005 wt. %, or the EDTA may be present in the buffer at a concentration of less than 0.003 wt. %.

In certain of the foregoing embodiments in which sodium citrate is present in the buffer, for example, the sodium citrate may be present in the buffer at a concentration in the range of 0.02-0.2 wt. %, for example at a concentration in the range of 0.01-0.1 wt. %, in the range of 0.02-0.075 wt. %, in the range of 0.03-0.06 wt. %, or the sodium citrate may be present in the buffer at a concentration in the range of 0.04-0.05 wt. %. In certain embodiments, for example, the sodium citrate may be present in the buffer at a concentration of 0.048 wt. %. In certain embodiments, for example, the sodium citrate may be present in the buffer at a concentration of less than 0.1 wt. %, for example a concentration of less than 0.075 wt. %, less than 0.06 wt. %, less than 0.05 wt. %, less than 0.04 wt. %, less than 0.03 wt. %, less than 0.02 wt. %, or the sodium citrate may be present in the buffer at a concentration of less than 0.01 wt. %. In certain embodiments, for example, the sodium citrate may be present in the buffer at a concentration of at least 0.01 wt. %, for example a concentration of at least 0.02 wt. %, at least 0.03 wt. %, at least 0.04 wt. %, or the sodium citrate may be present in the buffer at a concentration of at least 0.05 wt. %. In the foregoing embodiments, sodium citrate may refer to anhydrous sodium citrate or hydrated sodium citrate, for example sodium citrate dihydrate. Unless otherwise specified, the foregoing weight percentages of sodium citrate are calculated based on molecular weight of the particular form (for example the dihydrate form) in which it is added to form the composition. In certain embodiments, for example, the foregoing weight percentages of sodium citrate are calculated based on the molecular weight of sodium citrate.

In certain of the foregoing embodiments in which citric acid is present in the buffer, for example, the citric acid may be present in the buffer at a concentration in the range of 0.02-0.2 wt. %, for example at a concentration in the range of 0.01-0.1 wt. %, in the range of 0.02-0.075 wt. %, in the range of 0.04-0.07 wt. %, or the citric acid may be present in the buffer at a concentration in the range of 0.05-0.06 wt. %. In certain embodiments, for example, the citric acid may be present in the buffer at a concentration of 0.056 wt. %. In certain embodiments, for example, the citric acid may be present in the buffer at a concentration of less than 0.1 wt. %, for example a concentration of less than 0.075 wt. %, less than 0.06 wt. %, less than 0.05 wt. %, less than 0.04 wt. %, less than 0.03 wt. %, less than 0.02 wt. %, or the citric acid may be present in the buffer at a concentration of less than 0.01 wt. %. In certain embodiments, for example, the citric acid may be present in the buffer at a concentration of at least 0.01 wt. %, for example a concentration of at least 0.02 wt. %, at least 0.03 wt. %, at least 0.04 wt. %, or the citric acid may be present in the buffer at a concentration of at least 0.05 wt. %.

In certain of the foregoing embodiments in which sodium chloride is present in the buffer, for example, the sodium chloride may be present in the buffer at a concentration in the range of 0.01-2 wt. %, for example at a concentration in the range of 0.25-1.75 wt. %, in the range of 0.5-1.5 wt. %, in the range of 0.75-1.25 wt. %, or the sodium chloride may be present in the buffer at a concentration in the range of 0.825-0.875 wt. %. In certain embodiments, for example, the In certain embodiments, for example, the sodium chloride may be present in the buffer at a concentration of less than 1 wt. %, for example at a concentration of less than 0.875 wt. %. In certain embodiments, for example, the sodium chloride may be present in the buffer at a concentration of 0.8635 wt. %.

In certain embodiments, for example, the buffer may comprise one or more of acetate, barbital, borate, Britton-Robinson, cacodylate, citrate, collidine, formate, maleate, McMaine, phosphate, PrideauxWard, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, orAMPD buffer. In certain embodiments, for example, the buffer may consist of acetate, barbital, borate, Britton-Robinson, cacodylate, citrate, collidine, formate, maleate, McMaine, phosphate, PrideauxWard, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, orAMPD buffer.

In certain embodiments, for example, the homogeneous budesonide composition may comprise one or more surfactants. In certain embodiments, for example, the one or more surfactants may comprise C5-20 fatty alcohols, C5-20 fatty acids, C5-20 fatty acid esters, lecithin, glycerides, propylene glycol, esters, polyoxyethylenes, polysorbates, sorbitan esters and/or carbohydrates, or a combination of two or more of the foregoing surfactants.

In certain embodiments, for example, the homogeneous budesonide composition may comprise one or more antioxidants. In certain embodiments, for example, the one or more antioxidants may comprise ascorbic acid, vitamin A, vitamin E, tocopherols, vitamins or pro-vitamins occurring in the human body, or a combination of two or more of the foregoing antioxidants.

In certain embodiments, for example, the homogeneous budesonide composition may comprise one or more ingredients (for example one or more, such as all, inactive ingredients present in the homogeneous budesonide composition) at a concentration falling within limits defined by the United States Food and Drug Administration Inactive Ingredients Database and/or Inactive Ingredient Guide.

In certain embodiments, for example, the homogeneous budesonide composition may be free, or substantially free (i.e., less than 0.008 wt. %), of preservative including, but not limited to, quaternary ammonium preservatives, such as a benzalkonium salt, (e.g., benzalkonium chloride). In certain embodiments, for example, the homogeneous budesonide composition may comprise less than 0.1 wt. % preservative (or quaternary ammonium preservative) (such as less than 0.05 wt. %, less than 0.02 wt. %, or less than 0.008 wt. % preservative).

In certain embodiments, for example, the homogeneous budesonide composition may be free, or substantially free (i.e., less than 0.008 wt. %), of complexing agent (such as ethylene diamine tetra-acetic acid). In certain embodiments, for example, the homogeneous budesonide composition may comprise less than about 0.1 wt. % complexing agent (such as less than about 0.05 wt. %, less than about 0.02 wt. %, or less than about 0.008 wt. %), based on the weight of the homogeneous budesonide composition.

In certain embodiments, for example, the homogeneous budesonide solution may be free, or substantially free (i.e., less than 0.008 wt. %), of any component (for example any preservative (for example benzalkonium chloride), stabilizing agent, or complexing agent) which causes airway constriction in an ordinary subject when inhaled. In certain embodiments, for example, the homogeneous budesonide solution may be free, or substantially free (i.e., less than 0.008 wt. %) of any component (for example any preservative (for example benzalkonium chloride), stabilizing agent, or complexing agent) which reduces (or offsets) the effectiveness of budesonide in an ordinary subject when inhaled.

In certain embodiments, for example, the homogeneous budesonide composition may be free, or substantially free (i.e., less than 0.008 wt. %), of solids. In certain embodiments, for example, homogeneous budesonide composition may comprise less than 0.1 wt. % solids (such as less than 0.05 wt. %, less than 0.02 wt. %, or less than 0.008 wt. % solids), based on the total weight of the homogeneous budesonide composition. In certain embodiments, for example, the solids may comprise a precipitate. In certain embodiments, for example, the solids may comprise a flocculate. In certain embodiments, for example, the solids may comprise a residue. In certain embodiments, for example, the solids may comprise an impurity. In certain embodiments, for example, the solids may form in the homogeneous budesonide composition after a period of time (for example after 3 days, 7 days, 2 weeks, 3 weeks, 1 month, 3 months, 6 months, 12 months, 24 months, or 36 months). In certain embodiments, for example, the solids may form after heating the homogeneous budesonide composition (for example heating from 25° C. to 40° C., from 25° C. to 60° C., or from 25° C. to a temperature greater than 40° C.). In certain embodiments, for example, the solids may form after exposing the homogeneous budesonide composition to oxygen.

In certain embodiments, for example, the homogeneous budesonide composition may be exclusive of cyclodextrins. In certain embodiments, for example, the homogeneous budesonide composition may be exclusive of phospholipids. In certain embodiments, for example, the homogeneous budesonide composition may be exclusive of ethylene oxide-propylene oxide block copoylmers (for example one or more ethylene oxide-propylene oxide block copoylmers sold under the trade name PLURONIC). In certain embodiments, for example, the homogeneous budesonide composition may be exclusive of phosphatidylcholine derivatives. In certain embodiments, for example, the homogeneous budesonide composition may be exclusive of one or more PEG compounds. In certain embodiments, for example, the homogeneous budesonide composition may be exclusive of cellulose derivatives.

In certain embodiments, for example, the homogeneous budesonide solution may comprise a preservative. In certain embodiments, for example, the preservative may comprise a quarternary ammonium salt. In certain embodiments, for example, the preservative may comprise benzalkonium chloride. In certain embodiments, for example, the preservative may comprise polyhexamethylene biguanide. In certain embodiments, for example, the preservative may comprise benzoic acid. In certain embodiments, for example, the preservative may comprise a benzoate (for example sodium benzoate).

In certain embodiments, for example, the homogeneous budesonide composition may be a master batch comprising a concentrated amount of budesonide, for example a concentrated amount of budesonide of at least 0.1 wt. %, at least 0.2 wt. %, at least 0.3 wt. %, at least 0.35 wt. % or at least 0.5 wt. %. In certain embodiments, for example, the master batch may be diluted to form a second homogeneous budesonide composition. In certain embodiments, for example, the homogeneous budesonide composition may be an aqueous or nonaqueous solution and the second homogeneous budesonide composition may be a nanodispersion comprising nanoparticles of budesonide. In certain embodiments, for example, the homogeneous budesonide composition may be a nanodispersion comprising nanoparticles of budesonide and the second homogeneous budesonide composition may be an aqueous or nonaqueous solution. In certain embodiments, for example, the homogeneous budesonide composition may be a nanodispersion comprising nanoparticles of budesonide and the second homogeneous budesonide composition may be a nanodispersion comprising nanoparticles of budesonide. In certain embodiments, for example, the homogeneous budesonide composition may be an aqueous or nonaqueous solution and the second homogeneous budesonide composition may be an aqueous or nonaqueous solution. In certain embodiments, for example, the master batch may be diluted with water. In certain embodiments, for example, the master batch may be diluted by a buffer. In certain embodiments, for example, the second homogeneous budesonide composition may be a drug product. In certain further embodiments, for example, the drug product may be a sterile nebulizable pharmaceutical solution or nanodispersion for inhalation via nebulization. In certain embodiments, for example, the drug product may be a sterile ophthalmic solution or nanodispersion. In certain embodiments, for example, the drug product may be a sterile nasal spray (for example a sterile nasal spray providing in the range of 0.01-0.1 mg budesonide per spray, for example in the range of 0.01-0.05 mg budesonide per spray, for example 0.032 mg budesonide per spray). In certain embodiments, for example, the drug product may be a sterile topical solution or nanodispersion. In certain embodiments, for example, the drug product may be a sterile solution or nanodispersion suitable for intravenous injection or injection into tissue. In certain embodiments, for example, the second homogenous budesonide composition may be dried (for example spray dried or freeze dried) to form a sterile powdered drug product (for example a powdered drug product suitable for delivery by nasal or pulmonary inhalation).

In certain embodiments, for example, the homogeneous budesonide composition (for example a master batch or a drug product) may have a long (or acceptable) shelf life. In certain embodiments, for example, the homogeneous budesonide composition may be stable during long term storage. In certain embodiments, for example, the homogeneous budesonide composition may comprise greater than 80% of an initial quantity of budesonide following storage for a period of time, relative to a quantity of budesonide initially present in the homogeneous budesonide composition, for example greater than 85%, greater than 90%, greater than 95%, or the homogeneous budesonide composition may comprise or greater than 98% of an initial quantity of budesonide following storage for a period of time, relative to a quantity of budesonide initially present in the homogeneous budesonide composition. In certain further embodiments, for example, the storage may be at a temperature of 25° C. and the period of time may be 3 months, 6 months, 1 year, 2 years, or the period of time may be 3 years. In certain embodiments, for example, the storage may be at a temperature of 40° C. and the period of time may be 1 week, 2 weeks, 1 month, 2 months, or the period of time may be 3 months. In certain embodiments, for example, the storage may be at a temperature of 60° C. and the period of time may be 1 week, 2 weeks, 1 month, 2 months, or the period of time may be 3 months. In certain embodiments, for example, the storage may be at a specified relative humidity. In certain embodiments, for example, the specified relative humidity may be in the range of 10-90%, for example in the range of 20-30%, in the range of 30-50%, or the specified relative humidity may be in the range of 50-80%. In certain embodiments, for example, the specified relative humidity may be 25% or the specified relative humidity may be 40%. In certain embodiments, for example, the storage may be under low light or dark conditions (for example the container may be placed in an opaque wrapper such as a foil wrapper).

In certain embodiments, for example, the homogeneous budesonide composition may have an acceptable shelf life. In certain embodiments, for example, the acceptable shelf life may be greater than 80% of an initial quantity of budesonide following storage for six months, relative to a quantity of budesonide initially present in the homogeneous budesonide composition, for example greater than 85%, greater than 90%, greater than 95%, or the homogeneous budesonide composition may comprise or greater than 98% of an initial quantity of budesonide following storage for six months, relative to a quantity of budesonide initially present in the homogeneous budesonide composition.

In certain embodiments, for example, the homogeneous budesonide composition may have an acceptable shelf life. In certain embodiments, for example, the acceptable shelf life may be greater than 80% of an initial quantity of budesonide following storage for one year, relative to a quantity of budesonide initially present in the homogeneous budesonide composition, for example greater than 85%, greater than 90%, greater than 95%, or the homogeneous budesonide composition may comprise or greater than 98% of an initial quantity of budesonide following storage for one year, relative to a quantity of budesonide initially present in the homogeneous budesonide composition. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 80% of an initial quantity of budesonide following storage for one year. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 85% of an initial quantity of budesonide following storage for one year. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 90% of an initial quantity of budesonide following storage for one year. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 95% of an initial quantity of budesonide following storage for one year. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 98% of an initial quantity of budesonide following storage for one year.

In certain embodiments, for example, the homogeneous budesonide composition may have an acceptable shelf life. In certain embodiments, for example, the acceptable shelf life may be greater than 80% of an initial quantity of budesonide following storage for two years, relative to a quantity of budesonide initially present in the homogeneous budesonide composition, for example greater than 85%, greater than 90%, greater than 95%, or the homogeneous budesonide composition may comprise or greater than 98% of an initial quantity of budesonide following storage for two years, relative to a quantity of budesonide initially present in the homogeneous budesonide composition.

In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 80% of an initial quantity of budesonide following storage for two years. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 85% of an initial quantity of budesonide following storage for two years. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 90% of an initial quantity of budesonide following storage for two years. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 95% of an initial quantity of budesonide following storage for two years. In certain embodiments, for example, the homogeneous budesonide composition with an acceptable shelf life may comprise less than 0.1 wt. % (for example less than 0.07 wt. %, less than 0.04 wt. %, or in the range of 0.025-0.1 wt. %) of a polyvinyl caprolactam-polyvinyl acetate-polyethylene glycol graft copolymer (for example SOLUPLUS) and greater than 98% of an initial quantity of budesonide following storage for two years.

In certain embodiments, for example, a portion of a sample of one or more of the foregoing stored homogeneous budesonide compositions may be passed through an 0.2 micron polyvinylidene fluoride filter. In certain embodiments, for example, the budesonide content of the filtered portion may be reduced by less than 10% (as determined, for example, using high-performance liquid chromatography) compared to an unfiltered portion of the sample, for example reduced by less than less than 8%, less than 4%, less than 2%, less than 1%, or the budesonide content of the filtered portion may be reduced by less than 0.5% when the homogeneous budesonide composition is passed through an 0.2 micron polyvinylidene fluoride filter. In certain embodiments, for example, the portion of the sample passed through the filter may have been exposed to dark (no light) conditions at temperature of 25° C. and 40% relative humidity for 6 months, 1 year, or 2 years. In certain further embodiments, for example, the homogenous budesonide composition may be stored (prior to filtration) in a glass or blow-fill-seal container having an impermeable or semipermeable lid.

In certain embodiments, for example, a portion of a sample of a homogeneous budesonide composition may be passed through an 0.2 micron polyvinylidene fluoride filter. In certain embodiments, for example, the budesonide content of the filtered portion may be reduced by less than 10% (as determined, for example, using high-performance liquid chromatography) compared to an unfiltered portion of the sample, for example reduced by less than less than 8%, less than 4%, less than 2%, less than 1%, or the budesonide content of the filtered portion may be reduced by less than 0.5% when the homogeneous budesonide composition is passed through an 0.2 micron polyvinylidene fluoride filter.

In certain embodiments, for example, the sample may be unaged when filtered. In certain embodiments, for example, the sample may have been exposed to the Ambient Stability Test initially or for 14 days when filtered. In certain embodiments, for example, the sample may have been exposed to the Freeze-Thaw Stability Test for 3, 7, or 14 days when filtered. In certain embodiments, for example, sample may have been exposed to the Elevated Temperature Stability Test for 14 days when filtered. In certain embodiments, for example, the sample may have been exposed to the High Temperature Stability Test for 7 or 14 days when filtered.

In certain embodiments, for example, the storage may be in a glass container (for example a sterilized glass container). In certain embodiments, for example, the storage may be in a plastic container (for example a sterilized plastic container). In certain embodiments, for example, the plastic container may be a low density polyethylene container. In certain embodiments, for example, the plastic container may be a sterile, blow-fill-seal polyethylene container that is semipermeable to air and impermeable to microorganisms. In certain embodiments, for example, the storage may be in a cyclic olefin polymer container. In certain embodiments, for example, the storage may be in a cyclic olefin copolymer container. In certain embodiments, for example, the storage may be in a unit dose container. In certain embodiments, for example, the storage may be in a unit dose blow-fill-seal container. In certain embodiments, for example, the unit dose blow-fill-seal container may be contained in a foil pouch (for example a sealed foil pouch). In certain embodiments, for example, the sterile, stable, homogeneous budesonide composition may be sterile and remain sterile during the storage. In certain further embodiments, for example, the sterile, stable, homogeneous budesonide composition may be preservative-free or substantially preservative-free. In certain embodiments, for example, the sterile, stable, homogeneous budesonide composition may be benzalkonium chloride-free or substantially benzalkonium chloride-free.

In certain embodiments, for example, a unit dose of the homogeneous budesonide composition may retain greater than 85 wt. % of an initial quantity of budesonide and remain sterile when stored for 24 months in a unit dose, semi-permeable blow-fill-seal container under low light or no light (dark conditions) at 25° C. and 40% relative humidity. In certain embodiments, for example, a unit dose of the homogeneous budesonide composition may retain greater than 85 wt. % of an initial quantity of budesonide and remain sterile when stored for 1 month, 3 months, or 6 months in a unit dose, semi-permeable blow-fill-seal container under low light or no light (dark) conditions at 40° C. and 15% relative humidity.

In certain embodiments, for example, the homogeneous budesonide composition may be a nanodispersion comprising budesonide nanoparticles stably dispersed in a liquid medium. In certain further embodiments, for example, the nanodispersion may comprise supersaturated, stabilized nanoparticles of budesonide. In certain further embodiments, for example, the nanoparticles may be stabilized and/or their growth inhibited by an amphiphilic polymer. In certain embodiments, for example, the nanoparticles may be stabilized and/or their growth inhibited by a polyvinyl caprolactam-polyvinyl acetate-polyethylene glycol graft copolymer, polysorbate 80, or a combination of two or more of the foregoing polymers. In certain embodiments, for example, the nanoparticles may have an average size of less than 1 micron, for example an average size of less than 800 nm, less than 500 nm, less than 250 nm, less than 100 nm, less than 75 nm, less than 50 nm, or the nanoparticles may have an average size of less than 25 nm. In certain embodiments, for example, the nanoparticles may have an average size in the range of 10-800 nm, an average size in the range of 10-500 nm, in the range of 100-250 nm, or the nanoparticles may have an average size in the range of 250-800 nm.

In certain embodiments, for example, the homogeneous budesonide composition (for example a solution, nanodisperson, or microdispersion) may be nebulized to form droplets having an average size in the range of 0.1-10 microns, for example droplets having an average size in the range of 1-6 microns, in the range of 1-5 microns, in the range of 2-6 microns, or the homogeneous budesonide composition may be nebulized to form droplets having an average size in the range of 0.5-5 microns. In certain further embodiments, for example, the nebulizer may be a vibrating mesh nebulizer. In certain further embodiments, for example, the nebulizer may be a battery-powered, hand-held vibrating mesh nebulizer.

Certain embodiments may provide, for example, a unit dose container that contains a unit dose of the homogeneous budesonide composition (for example a homogeneous budesonide drug product). In certain further embodiments, for example, the unit dose may have a volume in the range of 0.1-6 mL, for example a volume in the range of 0.5-3 mL, such as a unit dose volume of 0.5 mL, 1 mL, or 2 mL. In certain embodiments, for example, the unit dose container may contain a volume of the homogeneous budesonide composition comprising a therapeutic quantity of budesonide. In certain further embodiments, for example, the unit dose container may comprise in the range of 1-3000 mcg of budesonide, for example in the range of 25-1500 mcg, 50-750 mcg, in the range of 75-600 mcg, in the range of 100-150 mcg, in the range of 120-130 mcg, in the range of 200-300 mcg, in the range of 225-257 mcg, in the range of 240-260 mcg, in the range of 400-600 mcg, in the range of 475-525 mcg, in the range of 500-750 mcg, in the range of 550-750 mcg, in the range of 525-700 mcg, in the range of 525-650 mcg, in the range of 550-675 mcg, in the range of 575-700 mcg, in the range of 575-675 mcg, in the range of 600-650 mcg, in the range of 575-625 mcg, or the unit dose container may comprise in the range of 490-510 mcg of budesonide. In certain embodiments, for example, any of the foregoing therapeutic quantities of budesonide may be present in a 0.5 mL unit dose volume of the homogeneous budesonide composition. In certain embodiments, for example, any of the foregoing therapeutic quantities of budesonide may be present in a 1 mL unit dose volume of the homogeneous budesonide composition. In certain embodiments, for example, any of the foregoing therapeutic quantities of budesonide may be present in a 2 mL unit dose volume of the homogeneous budesonide composition. In certain embodiments, for example, the unit dose may be defined by 250 mcg budesonide in 2 mL of the homogeneous budesonide composition. In certain embodiments, for example, the unit dose may be defined by 500 mcg budesonide in 2 mL of the homogeneous budesonide composition. In certain embodiments, for example, the unit dose may be defined by 1000 mcg budesonide, in 2 mL of the homogeneous budesonide composition.

In certain embodiments, for example, the unit dose container may be prepackaged. In certain embodiments, for example, the unit dose container may be sterile. In certain embodiments, for example, the unit dose container may contain a ready-to-use quantity of the homogeneous budesonide composition. In certain further embodiments, for example, the ready-to-use quantity of the homogeneous budesonide composition may not require any mixing or dilution prior to administration. In certain embodiments, for example, the unit dose container may contain a sterile, therapeutically effective quantity of budesonide, for the treatment, prevention, or amelioration of one or more symptoms of a disease or condition that causes a constriction or narrowing of the bronchi (for example a bronchoconstrictive disorder). In certain embodiments, for example, the disease or condition may be asthma, pediatric asthma, bronchial asthma, allergic asthma, intrinsic asthma, chronic obstructive pulmonary disease (COPD), chronic bronchitis, emphysema, or a combination of two or more of the foregoing diseases or conditions.

In certain embodiments, for example, the unit dose container may be formed aseptically using a blow-fill-seal process, wherein the container is formed, filled with a sterile volume of the homogeneous budesonide solution, and sealed in a continuous process without human intervention, in a sterile enclosed area inside a machine. In certain embodiments, for example, the blow-fill-seal process may comprise a) vertically heat extruding a pharmaceutical-grade plastic through a circular throat to form a parison (i.e., a tube such as a hanging tube); b) enclosing the extruded tube within a two-part mould; c) cutting the tube above the mould; transferring the mold to a sterile filling space, wherein one or more mandrels (i.e., filling needles) are lowered and used to inflate the plastic to form the container within the mould; d) filling the container, using the one or more filling needles, with the homogeneous budesonide solution; e) retracting the one or more filling needles; and f) forming a top in a secondary top mould to seal the container. In certain embodiments, for example, the process may comprise sterilization (for example sterile filtration) of the homogeneous budesonide composition prior to the filling. In certain embodiments, for example, the process may be exclusive of sterilization (for example thermal sterilization) following the filling. In certain embodiments, for example, the pharmaceutical-grade plastic may be polyethylene. In certain embodiments, for example, the pharmaceutical-grade plastic may be polypropylene.

Certain embodiments may provide, for example, a method to treat, prevent, or ameliorate one or more symptoms of a disease or condition that causes a constriction or narrowing of the bronchi (for example a bronchoconstrictive disorder). In certain embodiments, for example, the disease or condition may be asthma, pediatric asthma, bronchial asthma, allergic asthma, intrinsic asthma, chronic obstructive pulmonary disease (COPD), chronic bronchitis, and emphysema. In certain embodiments, for example, the method may comprise nebulization of one of the homogeneous budesonide compositions disclosed herein. In certain embodiments, for example, the method may comprise inhalation of one of the homogeneous budesonide compositions disclosed herein by a mammal, for example a human subject. In certain embodiments, for example, the method may comprise daily (for example once daily, twice daily, three times daily, or four times daily) nebulization of one of the homogeneous budesonide compositions disclosed herein by a mammal (for example a human subject in need of treatment). In certain further embodiments, for example, the method may comprise nebulization of at least a portion of a volume (for example a portion of 0.5 mL, 1 mL, 2 mL, or 4 mL) of the homogeneous budesonide composition using a nebulizer. In certain embodiments, for example, the nebulizer may be a jet nebulizer (for example an air-driven jet nebulizer or a jet nebulizer connected to an air compressor). In certain embodiments, for example, the nebulizer may be an ultrasonic nebulizer. In certain embodiments, for example, the nebulizer may be a vibrating mesh nebulizer. In certain embodiments, for example, the nebulizer may be a breath actuated nebulizer.

Certain embodiments may provide, for example, a method of treatment for subjects who find it difficult to use an inhaler. In certain embodiments, for example, the method may comprise administering one of the homogeneous budesonide compositions disclosed herein with one of the nebulizers disclosed herein (for example a jet nebulizer or a vibrating mesh nebulizer). In certain further embodiments, for example, the subject may be a pediatric patient. In certain further embodiments, for example, the subject may be a geriatric patient. In certain further embodiments, for example, the subject may be a patient with poor hand-inhalation coordination.

Certain embodiments may provide, for example, a kit to treat, prevent, or ameliorate one or more symptoms of a disease or condition that causes a constriction or narrowing of the bronchi (for example a bronchoconstrictive disorder). In certain embodiments, for example, the kit may comprise at least one (for example five) sterile unit dose container (for example a blow-fill-seal plastic container with a twist-off cap) containing a unit dose of the homogeneous budesonide composition, the unit dose having a therapeutically effective quantity budesonide. In certain embodiments, for example, the kit may further comprise a foil pouch (for example an opaque aluminum foil pouch) that contains the at least one sterile unit dose container. In certain embodiments, for example, the kits may comprise instructions for use. In certain embodiments, for example, the kit may comprise a medicine cup component of a hand-held vibrating mesh nebulizer. In certain embodiments, for example, the kit may comprise a hand-held, battery powered nebulizer.

EXAMPLES

In the following Examples: "q.s." refers to a quantity of buffer sufficient to bring the listed components to the concentrations indicated; "n.a." means "not applicable"; and "-" or "--" indicates no data presented.

Relative amounts of each component added to form the Examples are presented in Tables 1-5 and noted buffers are presented in Table 6.

Preparation of Example 1

A first solution was formed by dissolving, in 425 mL water: 4.3175 grams of sodium chloride, 240 mg of sodium citrate dihydrate, and 280 mg of citric acid anhydrous, followed by 175 mg SOLUPLUS and 290 mg Polysorbate 80. A second solution was formed by dissolving 125 mg budesonide micronized powder in 75 mL propylene glycol. The drug product composition having a budesonide concentration of 0.025 wt. % and pH of 4.5 was prepared by combining the first and second solutions with mixing under low shear for 30 minutes.

Preparation of Examples 2-8, 10, and 11

Budesonide micronized powder, followed by SOLUPLUS, were dissolved in solvent (propylene glycol, PEG 300, or ethanol) to form a clear, colorless first solution without any observable undissolved matter. A second solution was formed by dissolving polysorbate 80 in buffer to form a clear, colorless solution without any observable undissolved matter. Mixing the first solution and the second solution under low shear yielded a master batch with little or no foaming. The master batch was clear, colorless, and contained no observable undissolved matter. Diluting the master batch with buffer followed by mixing under low shear for 30 minutes gave a drug product composition having a pH of 4.5. Buffer A (see Table 6) was used in Examples 2-5, 10 and 11 and Buffer B was used in Examples 6-8.

Preparation of Example 9

SOLUPLUS, followed by micronized budesonide, were dissolved in PEG 300 to form a clear, colorless first solution without any observable undissolved matter. A second solution was formed by dissolving polysorbate 80 in Buffer B, followed by heating until colorless. Mixing the first solution and the second solution under low shear yielded a master batch with little or no foaming. Diluting the master batch with Buffer B followed by mixing under low shear for 30 minutes gave a drug product composition having a pH of 4.5.

Preparation of Comparative Example A

The drug product composition of Comparative Example A was prepared by the same procedure as Example 2, except that SOLUPLUS was omitted. The drug product composition had a pH of 4.5.

Preparation of Comparative Example B

Budesonide micronized powder, followed by SOLUPLUS, were dissolved in propylene glycol and diluted with Buffer A to form a master batch. Diluting the master batch with Buffer A followed by mixing under low shear for 30 minutes gave a drug product composition having a pH of 4.5.

Preparation of Comparative Example C

The master batch and drug product composition of Comparative Example C were prepared by the same procedure as Example 6, except that SOLUPLUS was omitted. The drug product composition had a pH of 4.5.

Preparation of Comparative Example D

The master batch and drug product composition of Comparative Example D were prepared by the same procedure as Example 6, except that polysorbate 80 was omitted. The drug product composition had a pH of 4.5.

Preparation of Comparative Example E

Budesonide micronized powder was dissolved in PEG 300 to form a first solution. A second solution was formed by dissolving SOLUPLUS in Buffer B followed by addition of polysorbate 80. Mixing the first solution and the second solution under high shear for 45 minutes yielded a master batch. Diluting the master batch with Buffer B followed by mixing under low shear for 30 minutes gave a drug product composition having a pH of 4.5.

Preparation of Comparative Example F

Budesonide micronized powder and SOLUPLUS were dissolved in PEG 300 to form a first solution. A second solution was formed by dissolving polysorbate 80 in Buffer B. Mixing the first solution and the second solution under high shear for 45 minutes yielded a master batch. Diluting the master batch with Buffer B followed by mixing under low shear for 30 minutes gave a drug product composition having a pH of 4.5.

Preparation of Comparative Examples G-M

Budesonide micronized powder was mixed with PEG 300 and SOLUPLUS, followed by addition to ethanol to form a master batch. Diluting the master batch with Buffer B followed by mixing under low shear for 30 minutes gave a drug product composition having a pH of 4.5.

Preparation of Comparative Example N

Budesonide micronized powder was dissolved in ethanol to form a first solution. A second solution was formed by dissolving SOLUPLUS in Buffer B. The drug product composition having a pH of 4.5 was prepared by combining the first solution and the second solution followed by low shear mixing for 30 minutes.

Preparation of Comparative Example 0

Budesonide micronized powder and SOLUPLUS were dissolved in propylene glycol, followed by dilution with Buffer B to form a master batch. The drug product composition having a pH of 4.5 was prepared by diluting a portion of the master batch with further Buffer B, followed by low shear mixing for 30 minutes.

Preparation of Example 12

A first solution was formed by dissolving sodium chloride, sodium citrate dihydrate, citric acid anhydrous, and EDTA in water, followed by addition of SOLUPLUS and Polysorbate 80. A second solution was formed by dissolving budesonide micronized powder in propylene glycol. The drug product composition having a budesonide concentration of 0.025 wt. % and pH of approximately 4.5 was prepared by combining the first and second solutions with mixing at 400 RPM until the budesonide was fully dissolved, followed by mixing at 400 RPM at a temperature of 60° C. for 60 minutes, cooling to room temperature and adjusting the pH using 2.5 mL of 10% sodium citrate solution.

Preparation of Examples 13-15

A first solution was formed by dissolving sodium chloride, sodium citrate dihydrate, and citric acid anhydrous in water, followed by addition of SOLUPLUS and Polysorbate 80. A second solution was formed by dissolving budesonide micronized powder in propylene glycol. The drug product composition having a budesonide concentration of approximately 0.025 wt. % and pH of approximately 4.5 was prepared by combining the first and second solutions with mixing at 400 RPM until the budesonide was fully dissolved, followed by mixing at 400 RPM at a temperature of 60° C. for 60 minutes, cooling to room temperature and adjusting the pH using 2.5 mL of 10% sodium citrate solution.

Preparation of Example 16

A first solution was formed by dissolving sodium chloride, sodium citrate dihydrate, and citric acid anhydrous followed by addition of SOLUPLUS and Polysorbate 80. A second solution was formed by dissolving budesonide micronized powder in propylene glycol. The drug product composition having a budesonide concentration of approximately 0.025 wt. % and pH of approximately 4.5 was prepared by combining the first and second solutions with mixing at 400 RPM until the budesonide was fully dissolved, followed by mixing at 400 RPM at a temperature of 60° C. for 30 minutes and further heating (without mixing) at a temperature of 60° C. for 30 minutes, cooling to room temperature and adjusting the pH using 2.5 mL of 10% sodium citrate solution.

Other Experiments

In a separate series of experiments, compositions exclusive of SOLUPLUS and/or polysorbate 80 were each observed to have a hazy appearance and/or form precipitate.

In a further experiment, budesonide was found not to be soluble in pure glycerol.

In another series of experiments, compositions comprising 0.125-0.5 mg budesonide added to a clear solution of up to 1.5 mg SOLUPLUS dissolved in Buffer A had a cloudy-white appearance.

TABLE 1

Drug Product Compositions (wt. %)

| Component | Examples | | | | | | | | | | |
|---|---|---|---|---|---|---|---|---|---|---|---|
| | 2 | 3 | 4 | 5 | 6 | 7 | 8a | 8b | 9 | 10 | 11 |
| Propylene glycol | 5 | 5 | — | — | 5 | 6.2 | 7.5 | 5.2 | — | 7.4 | 5.2 |
| PEG 300 | — | — | — | — | — | — | — | — | 1.1 | — | — |
| Ethanol | — | — | 4 | 4 | — | — | — | — | — | — | — |
| Budesonide | 0.025 | 0.025 | 0.025 | 0.025 | 0.025 | 0.025 | 0.036 | 0.025 | 0.025 | 0.025 | 0.025 |
| SOLUPLUS | 0.035 | 0.05 | 0.035 | 0.05 | 0.03 | 0.03 | 0.05 | 0.035 | 0.025 | 0.035 | 0.035 |
| Polysorbate 80 | 0.058 | 0.058 | 0.059 | 0.059 | 0.04 | 0.2 | 0.029 | 0.02 | 0.20 | 0.058 | 0.058 |
| Buffer A[1] | q.s. | q.s. | q.s. | q.s. | — | — | — | — | — | q.s. | q.s. |
| Buffer B | — | — | — | — | q.s. | q.s. | q.s. | q.s. | q.s. | — | — |

[1]Buffer compositions disclosed in Table 5.

TABLE 2

Drug Product Compositions (wt. %)

| Component | Examples | | | | |
|---|---|---|---|---|---|
| | 12 | 13 | 14 | 15 | 16 |
| Propylene glycol | 15.265 | 15.266 | 15.261 | 15.257 | 15.266 |
| Budesonide | 0.025 | 0.025 | 0.024 | 0.024 | 0.024 |
| SOLUPLUS | 0.034 | 0.034 | 0.068 | 0.098 | 0.034 |
| Polysorbate 80 | 0.057 | 0.057 | 0.057 | 0.057 | 0.057 |
| EDTA | 0.010 | — | — | — | — |
| Citric Acid Anhydrous | 0.055 | 0.055 | 0.055 | 0.055 | 0.055 |
| Sodium Citrate Dihydrate | 0.047 | 0.047 | 0.047 | 0.047 | 0.047 |
| Sodium Chloride | 0.845 | 0.845 | 0.845 | 0.844 | 0.845 |
| Water | q.s. | q.s. | q.s. | q.s. | q.s. |

TABLE 3

Drug Product Compositions (wt. %)

| Component | Comparative Examples | | | | | | | | | | | | | | |
|---|---|---|---|---|---|---|---|---|---|---|---|---|---|---|---|
| | A | B | C | D | E | F | G | H | I | J | K | L | M | N | O |
| Propylene glycol | 5 | 5 | 5 | 5 | — | — | — | — | — | — | — | — | — | — | 2.0 |
| PEG 300 | — | — | — | — | 1.1 | 1.1 | 3.4 | 3.4 | 3.4 | 3.4 | 3.4 | 3.4 | 3.4 | — | — |
| Ethanol | — | — | — | — | — | — | 0.79 | 0.79 | 0.79 | 0.79 | 0.79 | 0.79 | 0.79 | 0.79 | — |
| Budesonide | 0.025 | 0.025 | 0.025 | 0.025 | 0.025 | 0.025 | 0.025 | 0.025 | 0.025 | 0.025 | 0.025 | 0.025 | 0.025 | 0.025 | 0.025 |
| SOLUPLUS | — | 0.05 | — | 0.03 | 0.025 | 0.025 | 0.010 | 0.02 | 0.025 | 0.03 | 0.04 | 0.05 | 0.06 | 0.050 | 0.025 |
| Polysorbate 80 | 0.058 | — | 0.04 | — | 0.2 | 0.2 | — | — | — | — | — | — | — | — | — |
| Buffer A | q.s. | q.s. | — | — | — | — | — | — | — | — | — | — | — | — | — |
| Buffer B | — | — | q.s. | q.s. | q.s. | q.s. | q.s. | q.s. | q.s. | q.s. | q.s. | q.s. | q.s. | q.s. | q.s. |

TABLE 4

Master Batch Compositions (wt. %)

| Component | Examples | | | | | | | | | | |
|---|---|---|---|---|---|---|---|---|---|---|---|
| | 2 | 3 | 4 | 5 | 6 | 7 | 8a | 8b | 9 | 10 | 11 |
| Propylene glycol | 50 | 50 | — | — | 70 | 59 | 71 | 71 | — | 59 | 51 |
| PEG 300 | — | — | — | — | — | — | — | — | 22 | — | — |
| Ethanol | — | — | 44 | 44 | — | — | — | — | — | — | — |
| Budesonide | 0.25 | 0.25 | 0.28 | 0.28 | 0.35 | 0.24 | 0.34 | 0.34 | 0.48 | 0.20 | 0.24 |
| SOLUPLUS | 0.35 | 0.50 | 0.39 | 0.55 | 0.42 | 0.29 | 0.48 | 0.48 | 0.48 | 0.28 | 0.34 |
| Polysorbate 80 | 0.58 | 0.58 | 0.64 | 0.64 | 0.56 | 1.9 | 0.28 | 0.28 | 3.9 | 0.47 | 0.57 |
| Buffer A | q.s. | q.s. | q.s. | q.s. | — | — | — | — | — | q.s. | q.s. |
| Buffer B | — | — | — | — | q.s. | q.s. | q.s. | q.s. | q.s. | — | — |

TABLE 5

Master Batch Compositions (wt. %)

| Component | Comparative Examples | | | | | | | | | | | | | | |
|---|---|---|---|---|---|---|---|---|---|---|---|---|---|---|---|
| | A | B | C | D | E | F | G | H | I | J | K | L | M | N | O |
| Propylene glycol | 50 | 50 | 70 | 70 | — | — | — | — | — | — | — | — | — | n.a. | 17 |
| PEG 300 | — | — | — | — | 11.4 | 11.4 | 80.4 | 80.2 | 80.1 | 80.0 | 79.8 | 79.6 | 79.4 | — | — |
| Ethanol | — | — | — | — | — | — | 18.8 | 18.7 | 18.7 | 18.7 | 18.7 | 18.6 | 18.6 | — | — |
| Budesonide | 0.25 | 0.25 | 0.35 | 0.35 | 0.26 | 0.26 | 0.6 | 0.6 | 0.6 | 0.6 | 0.6 | 0.6 | 0.6 | — | 0.2 |
| SOLUPLUS | — | 0.50 | — | 0.42 | 0.26 | 0.26 | 0.2 | 0.5 | 0.6 | 0.7 | 0.9 | 1.2 | 1.4 | — | 0.2 |
| Polysorbate 80 | 0.58 | — | 0.56 | — | 2.1 | 2.1 | — | — | — | — | — | — | — | — | — |
| Buffer A | q.s. | q.s. | — | — | — | — | — | — | — | — | — | — | — | — | q.s. |
| Buffer B | — | — | q.s. | q.s. | q.s. | q.s. | — | — | — | — | — | — | — | — | q.s. |

TABLE 6

| Component | Buffer A (EDTA-free) | Buffer B (with EDTA) |
|---|---|---|
| Buffer Compositions (wt. %) | | |
| EDTA | — | 0.01 |
| Citric Acid Anhydrous | 0.056 | 0.056 |
| Sodium Citrate Dihydrate | 0.048 | 0.048 |
| Sodium Chloride | 0.8635 | 0.8635 |
| Water | q.s. | q.s. |

Unfiltered and filtered samples of drug product compositions of Examples 1-5 and 12-16 and Comparative Examples A and B were assayed by high-performance liquid chromatography (HPLC). Percent budesonide assay results (sample signal relative to control) are presented in Tables 7 and 8. Polyvinylidene fluoride filters (0.2 micron) were used for sample filtration.

In Examples 6-11 and Comparative Examples C-O, visual stability observations were logged for the master batch and drug product compositions. Results are presented in Table 9.

TABLE 7

Stability Test Results - Percent Budesonide Assay (%)

| Example | Sample | Ambient Stability Test[1] Initial | Ambient Stability Test[1] 14 Days | Freeze-Thaw Stability Test[2] 3 Days | Freeze-Thaw Stability Test[2] 7 Days | Freeze-Thaw Stability Test[2] 14 Days | Elevated Temperature Stability Test[3] 14 Days | High Temperature Stability Test[4] 7 Days | High Temperature Stability Test[4] 14 Days |
|---|---|---|---|---|---|---|---|---|---|
| 1 | Unfiltered | 99.7 | 99.2 | 99.1 | 96.0 | 96.9 | 98.2 | 95.4 | 92.8 |
|   | Filtered | 94.7 | 93.5 | 88.7 | 87.8 | 91.0 | 92.5 | 90.8 | 88.7 |
| 2 | Unfiltered | 103.9 | 102.8 | 99.4 | 101.0 | 104.6 | 100.0 | 92.6 | 84.1 |
|   | Filtered | 95.6 | 92.6 | 87.4 | 79.2 | 86.1 | 91.5 | 83.2 | 75.1 |
| 3 | Unfiltered | 105.5 | 103.5 | 97.4 | 96.1 | 101.2 | 103.1 | 99.4 | 95.6 |
|   | Filtered | 97.7 | 94.4 | 84.7 | 76.9 | 86.3 | 92.9 | 89.7 | 85.3 |
| 4 | Unfiltered | 105.3 | 103.5 | 98.9 | 99.5 | 101.6 | 102.3 | 87.8 | 79.8 |
|   | Filtered | 97.6 | 95.1 | 87.4 | 81.3 | 69.7 | 93.5 | 79.5 | 73.4 |
| 5 | Unfiltered | 106.4 | 102.6 | 95.5 | 94.3 | 94.1 | 103.2 | 96.9 | 86.7 |
|   | Filtered | 99.3 | 93.1 | 83.1 | 77.6 | 75.3 | 93.8 | 88.7 | 79.2 |
| Comparative Example | | | | | | | | | |
| A | Unfiltered | 97.0 | 100.2 | 103.0 | 101.0 | 106.8 | 99.5 | 103.2 | 101.5 |
|   | Filtered | 15.3 | 14.8 | 10.3 | 10.2 | 10.9 | 15.3 | 20.5 | 21.4 |
| B | Unfiltered | 101.8 | 100.9 | 94.8 | 92.5 | 90.1 | 100.5 | 98.3 | 97.1 |
|   | Filtered | 92.4 | 87.9 | 73.8 | 68.7 | 79.1 | 88.4 | 85.8 | 82.1 |

Percent budesonide assay was determined by HPLC under the conditions indicated:
[1]Glass container in dark at 25° C. (60% relative humidity).
[2]Glass container in dark at −20° C., then thawed to 25° C. for assay.
[3]Glass container in dark at 40° C. (75% relative humidity).
[4]Glass container in dark at 60° C.

TABLE 8

Stability Test Results - Percent Budesonide Assay (%)

| Example | Sample | Ambient Stability Test[1] Initial | Ambient Stability Test[1] 6 Months | Low Temperature Stability Test[2] 3 Months | Elevated Temperature Stability Test[3] 3 Months | High Temperature Stability Test[4] 1 Month |
|---|---|---|---|---|---|---|
| 12 | Unfiltered | 104.8 | 52.3 | 105.6 | 92.5 | 97.5 |
|    | Filtered | 98.9 | 46.0 | 87.4 | 87.1 | 93.6 |
| 13 | Unfiltered | 107.5 | 56.9 | 104.0 | 99.7 | 94.7 |
|    | Filtered | 101.5 | 52.9 | 97.0 | 94.1 | 88.7 |
| 14 | Unfiltered | 106.2 | 75.6 | 104.8 | 97.1 | 97.1 |
|    | Filtered | 100.2 | 71.7 | 100.1 | 98.9 | 92.5 |
| 15 | Unfiltered | 103.0 | 95.2 | 103.1 | 98.3 | 89.9 |
|    | Filtered | 98.0 | 91.2 | 97.0 | 94.8 | 80.7 |
| 16 | Unfiltered | 101.2 | 55.2 | 98.4 | 94.4 | 89.8 |
|    | Filtered | 97.7 | 52.0 | 92.1 | 88.8 | 84.5 |

Percent budesonide assay was determined by HPLC under the conditions indicated:
[1]Glass container in dark at 25° C. (60% relative humidity).
[2]Glass container in dark at 2-8° C.
[3]Glass container in dark at 40° C. (75% relative humidity).
[4]Glass container in dark at 60° C.

TABLE 9

Stability Test Results

| Composition | Master Batch Observations | Drug Product Composition Observations |
|---|---|---|
| Example 6 | Clear, colorless, precipitate-free | Clear, colorless, precipitate-free |
| Example 7 | Clear, colorless, precipitate-free | Clear, colorless, precipitate-free |
| Example 8-a | Clear, colorless, precipitate-free | Clear, colorless, precipitate-free |
| Example 8-b | Clear, colorless, precipitate-free | Clear, colorless, precipitate-free |
| Example 9 | Clear, colorless, precipitate-free | Clear, colorless, precipitate-free |
| Example 10 | Clear, colorless, precipitate-free | Clear, colorless, precipitate-free |
| Example 11 | Clear, colorless, precipitate-free | Clear, colorless, precipitate-free |
| Comparative Example C | Precipitate | — |
| Comparative Example D | Precipitate | — |
| Comparative Example E | Opaque white haze (no particulates), foam | — |
| Comparative Example F | Milky-white haze (no particulates); foam | — |
| Comparative Example G | — | Slight haze, precipitate-free |
| Comparative Example H | — | Slight haze, precipitate-free |
| Comparative Example I | — | Slight haze, precipitate-free |
| Comparative Example J | — | Slight haze, precipitate-free |
| Comparative Example K | — | Slight haze, precipitate-free |
| Comparative Example L | — | Slight haze, precipitate-free |
| Comparative Example M | — | Slight haze, precipitate-free |
| Comparative Example N | — | Precipitate |
| Comparative Example O | — | Slight haze, precipitate-free |

All publications and patent applications mentioned in this specification are herein incorporated by reference to the same extent as if each individual publication or patent application was specifically and individually indicated to be incorporated by reference.

As used herein, budesonide means budesonide or a pharmaceutically acceptable salt thereof. A specified weight percentage or concentration of budesonide or a pharmaceutically acceptable salt thereof in a composition means the weight percentage or concentration based on the molecular weight of budesonide (not the molecular weight of the pharmaceutically acceptable salt if such a salt is employed).

As used herein, citric acid means citric acid or a hydrate thereof. Unless otherwise specified, a specified weight percentage or concentration of citric acid or a hydrate thereof in a solution means the weight percentage or concentration based on the molecular weight of anhydrous citric acid (not the molecular weight of a hydrate of citric acid if such a hydrate is used). A specified weight percentage or concentration referring specifically to a hydrate of citric acid means the weight percentage or concentration based on the molecular weight of the specified hydrate.

As used herein, sodium citrate means sodium citrate or a hydrate thereof. Unless otherwise specified, a specified weight percentage or concentration of sodium citrate or a hydrate thereof in a solution means the weight percentage or concentration based on the molecular weight of sodium citrate dihydrate (not the molecular weight of a anhydrous citric acid if such a hydrate is used). A specified weight percentage or concentration referring specifically to a hydrate of sodium citrate means the weight percentage or concentration based on the molecular weight of the specified hydrate.

As used herein, ethylenediaminetetraacetic acid (EDTA) refers to ethylenediaminetetraacetic acid or a salt thereof (for example disodium edetate). Unless otherwise specified, a specified weight percentage or concentration of EDTA means the weight percentage or concentration based on the molecular weight of EDTA (not the molecular weight of the salt if such a salt is employed). A specified weight percentage or concentration referring specifically to a salt of EDTA means the weight percentage or concentration based on the molecular weight of the specified salt.

Unless specified otherwise, a weight percentage of a component of a composition means the weight percentage, on an as-added basis, relative to the total weight of the composition. For example, "a composition comprising 1 wt. % budesonide" means 1 wt. % of budesonide was added (regardless of whether or not the budesonide undergoes a chemical transformation once present in the composition) relative to the total weight of the composition or as otherwise specified.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A stable, homogeneous budesonide composition comprising:
   i) 0.0125-0.15 wt. % budesonide;
   ii) a polyvinyl caprolactam-polyvinyl acetate-polyethylene glycol graft copolymer, present at a weight ratio of less than 3:1, relative to the weight of budesonide in the composition; and
   iii) at least 90 wt. % water.

2. The composition of claim 1, further comprising: polysorbate 80 present at a weight ratio of less than 3:1, relative to the budesonide concentration.

3. The composition of claim 1, wherein the composition is benzalkonium chloride-free.

4. The composition of claim 1, wherein the composition is stable following storage in a polyethylene container for 24 months at a temperature of 25° C.

5. The composition of claim 1, wherein the composition is a dispersion.

6. The composition of claim 1, wherein the composition is a nanodispersion.

7. A drug product, comprising: a sterile volume of the composition of claim 1 in a single dose, blow-fill-seal container.

8. An aseptic process to form a drug product composition, comprising:
   i) injecting a volume of the composition of claim 1 into a sterile blow-fill-seal container; and
   ii) sealing the sterile blow-fill-seal container.

9. The process of claim 8, further comprising: sterilizing the volume of the composition of claim 1 prior to the injecting.

10. The process of claim 8, wherein the aseptic process is exclusive of sterilization following the sealing.

11. A method of treating, preventing, or ameliorating one or more symptoms of a bronchoconstriction-related disease or disorder, comprising:

nebulizing, by a nebulizer, a unit dose of the composition of claim 1.

12. A homogeneous, pharmaceutical composition comprising:
   i) at least 0.01 wt. % budesonide;
   ii) less than 0.05 wt. % polyvinyl caprolactam-polyvinyl acetate-polyethylene glycol graft copolymer;
   iii) less than 1 wt. % polysorbate 80;
   iv) less than 0.01 wt. % ethylenediaminetetraacetic acid;
   v) citric acid;
   vi) sodium citrate; and
   vii) sodium chloride,
the pharmaceutical composition exclusive of preservatives.

13. A method to prepare a precipitate-free composition, comprising:
   i) forming a budesonide-containing first liquid, comprising: dispersing a quantity of budesonide micronized powder in a volume of first liquid;
   ii) forming a second liquid, comprising: dissolving a quantity of polyvinyl caprolactam-polyvinyl acetate-polyethylene glycol graft copolymer in a volume of water; and
   iii) mixing at least a portion of the budesonide-containing first liquid with a volume of the second liquid for at least 30 minutes to form the precipitate-free composition, the precipitate-free composition comprising at least 90 wt. % water, wherein the method is exclusive of high shear mixing; and wherein the precipitate-free composition comprises the composition of claim 1.

14. The method of claim 13, wherein the precipitate-free composition is a dispersion.

15. The method of claim 13, wherein the precipitate-free composition is a nanodispersion.

16. The method of claim 13, wherein the concentration of budesonide is in the range of 125-1500 mcg budesonide per 2 mL of the precipitate-free composition.

17. The method of claim 13, wherein the first liquid comprises propylene glycol and/or ethanol.

18. The method of claim 13, wherein the second liquid comprises polysorbate 80.

\* \* \* \* \*